US010337037B2

(12) United States Patent
Ozaki et al.

(10) Patent No.: US 10,337,037 B2
(45) Date of Patent: Jul. 2, 2019

(54) METHOD OF PRODUCING LIPID

(71) Applicant: KAO CORPORATION, Chuo-ku, Tokyo (JP)

(72) Inventors: Tatsuro Ozaki, Wakayama (JP); Shinji Sugihara, Wakayama (JP)

(73) Assignee: Kao Corporation, Tokyo (JP)

( * ) Notice: Subject to any disclaimer, the term of this patent is extended or adjusted under 35 U.S.C. 154(b) by 24 days.

(21) Appl. No.: 15/747,936

(22) PCT Filed: Aug. 2, 2016

(86) PCT No.: PCT/JP2016/072606
§ 371 (c)(1),
(2) Date: Jan. 26, 2018

(87) PCT Pub. No.: WO2017/022740
PCT Pub. Date: Feb. 9, 2017

(65) Prior Publication Data

US 2019/0010525 A1 Jan. 10, 2019

(30) Foreign Application Priority Data

Aug. 5, 2015 (JP) ................................ 2015-154771

(51) Int. Cl.

| | |
|---|---|
| ***C12P 7/64*** | (2006.01) |
| ***C12N 5/10*** | (2006.01) |
| ***C12N 15/09*** | (2006.01) |
| ***C12N 1/12*** | (2006.01) |
| ***C12N 9/10*** | (2006.01) |
| ***C12N 15/52*** | (2006.01) |
| ***C12N 15/70*** | (2006.01) |
| ***C12N 15/82*** | (2006.01) |

(52) U.S. Cl.
CPC .................. *C12P 7/64* (2013.01); *C12N 1/12* (2013.01); *C12N 5/10* (2013.01); *C12N 9/1029* (2013.01); *C12N 15/09* (2013.01); *C12N 15/52* (2013.01); *C12N 15/70* (2013.01); *C12N 15/8247* (2013.01); *C12P 7/6472* (2013.01); *C12Y 203/01041* (2013.01)

(58) Field of Classification Search
CPC .................................... C12N 5/10; C12P 7/64
See application file for complete search history.

(56) References Cited

U.S. PATENT DOCUMENTS

| | | | | |
|---|---|---|---|---|
| 2012/0277418 A1 | | 11/2012 | Killian et al. | |
| 2013/0102040 A1* | | 4/2013 | Radakovits ............ | C12N 15/79 435/134 |
| 2017/0044580 A1 | | 2/2017 | Sugihara et al. | |
| 2017/0107545 A1 | | 4/2017 | Tojo et al. | |

FOREIGN PATENT DOCUMENTS

| | | | |
|---|---|---|---|
| JP | 2017-201905 | A | 11/2017 |
| WO | WO 2012/052468 | A2 | 4/2012 |
| WO | WO 2012/149457 | A1 | 11/2012 |
| WO | WO 2015/133305 | A1 | 9/2015 |
| WO | WO 2016/021481 | A1 | 2/2016 |

OTHER PUBLICATIONS

International Search Report (ISR) for PCT/JP2016/072606; I.A. fd Aug. 2, 2016, dated Sep. 20, 2016 from the Japan Patent Office, Tokyo, Japan.
International Preliminary Report on Patentability (IPRP), Chapter I of the Patent Cooperation Treaty, including the Written Opinion for PCT/JP2016/072606; I.A. fd Aug. 2, 2016, dated Feb. 6, 2018, by the International Bureau of WIPO, Geneva, Switzerland.
TSA: Nannochloropsis gaditana CCMP526 NGA_Contig29928 mRNA, Database Genbank [online], Accession No. JU980979.1, May 16, 2012 [retrieved on Aug. 25, 2016], Retrieved from the Internet, URL: <http://www.ncbi.nlm.nih.gov/nuccore/JU980979>.
Chaturvedi, R et al., "Isolation of enhanced eicosapentaenoic acid producing mutants of *Nannochloropsis oculata* ST-6 using ethyl methane sulfonate induced mutagenesis techniques and their characterization at mRNA transcript level," Phycological Research 54(3): 208-219 (Sep. 2006); doi 10.1111/j.1440-1835.2006.00428.x, Japanese Society of Phycology, Tokyo, Japan.
Lei, A et al, "Expression of fatty acid synthesis genes and fatty acid accumulation in *haematococcus pluvialis* under different stressors," Biotechnol Biofuels. Mar. 26, 2012;5(1):18. doi: 10.1186/1754-6834-5-18, 11 pages, BioMed Central, London, England.
Hauvermale, A et al., "Fatty acid production in *Schizochytrium* sp.: Involvement of a polyunsaturated fatty acid synthase and a type I fatty acid synthase," Lipids. Aug. 2006;41(8):739-47, American Oil Chemists' Society, Chicago, IL.

* cited by examiner

*Primary Examiner* — Tekchand Saidha
(74) *Attorney, Agent, or Firm* — Sterne, Kessler, Goldstein & Fox P.L.L.C.

(57) ABSTRACT

A method of producing lipids, containing the steps of:

culturing a transformant in which the expression of a gene encoding the following protein (A) or (B) is enhanced, and producing long-chain fatty acids or the lipids containing these fatty acids as components, wherein:

protein (A) is a protein consisting of the amino acid sequence set forth in SEQ ID NO: 1; and protein (B) is a protein consisting of an amino acid sequence having 70% or more identity with the amino acid sequence of the protein (A), and having β-ketoacyl-ACP synthase activity.

16 Claims, No Drawings

Specification includes a Sequence Listing.

SEQUENCE LISTING

```
<160> NUMBER OF SEQ ID NOS: 60

<210> SEQ ID NO 1
<211> LENGTH: 475
<212> TYPE: PRT
<213> ORGANISM: Nannochloropsis oculata

<400> SEQUENCE: 1

Met Met Glu Lys Leu Thr Leu Ala Val Val Gly Ser Leu Ala Leu Thr
1               5                   10                  15

Ser Ala Phe Gln Pro Ser Ser Phe Phe Leu Arg Gln Thr Ser Ser Val
            20                  25                  30

Ser Ser Ser Ser Ser Ser Ser Arg Thr Val Arg Arg Ala Ser Gly Glu
        35                  40                  45

Val Ser Met Ala Asp Leu Pro Pro Leu Val Arg Lys Arg Val Val Ile
    50                  55                  60

Thr Gly Val Gly Ala Val Ser Pro Leu Gly Trp Gly Asp Asp Phe Trp
65                  70                  75                  80

Asn Gly Leu Val Glu Gly Arg Ser Gly Ile Val Arg Leu Pro Ser Trp
                85                  90                  95

Ala Asp Glu Tyr Pro Ala Arg Ile Gly Gly Leu Val Pro Asp His Phe
            100                 105                 110

Lys Pro Ser Asp Tyr Met Asn Ala Lys Glu Val Lys Arg Gln Ala Arg
```

```
        115                 120                 125

Phe Thr His Phe Ala Met Ala Ala Ala Arg Met Ala Val Glu Asp Ala
    130                 135                 140

Lys Leu Asp Leu Glu Lys Val Asp Arg Ser Arg Ala Gly Cys Met Ile
145                 150                 155                 160

Gly Ser Gly Ile Gly Gly Val Glu Ile Phe Glu Lys Asn Cys Gly Glu
                165                 170                 175

Phe Asp Lys Lys Gly Gly Gly Leu Pro Gly Leu Lys Ala Val Ser Pro
            180                 185                 190

Phe Leu Ile Pro Ala Leu Ile Ala Asn Thr Ala Ala Gly Thr Val Ala
        195                 200                 205

Ile Glu Leu Gly Leu Lys Gly Pro Asn Tyr Cys Ser Val Ser Ala Cys
    210                 215                 220

Ala Ser Gly Thr His Thr Ile Gly Asp Ala Phe Phe Phe Leu Gln Asn
225                 230                 235                 240

Gly Met Ala Asp Val Cys Val Thr Gly Gly Thr Glu Ala Ala Ile Thr
                245                 250                 255

Pro Leu Cys Phe Ala Gly Phe Val Ala Ile Arg Ala Leu Thr Thr Ser
            260                 265                 270

Gly Asn Asp Asp Pro Thr Lys Ala Ser Lys Pro Phe Asp Lys Asn Arg
        275                 280                 285

Ala Gly Phe Val Met Ala Glu Gly Ala Gly Met Leu Val Leu Glu Thr
    290                 295                 300

Glu Glu His Ala Lys Ala Arg Gly Ala Thr Ile Tyr Ala Glu Leu Ala
305                 310                 315                 320

Gly Tyr Gly Ala Ser Cys Asp Ala His His Ile Thr Ala Pro His Pro
                325                 330                 335

Glu Gly Glu Gly Leu Ala Asn Ala Met Asn Met Ala Leu Thr Ser Ala
            340                 345                 350

Gly Leu Lys Pro Thr Asp Val Asp Tyr Ile Asn Ala His Gly Thr Ser
        355                 360                 365

Thr Ala Tyr Asn Asp Lys Phe Glu Thr Leu Ala Ile His Arg Val Phe
    370                 375                 380

Gly Glu His Ala Lys Lys Leu Lys Val Ser Ser Ile Lys Ser Met Thr
385                 390                 395                 400

Gly His Ser Leu Gly Ala Ala Gly Ala Phe Glu Ala Val Ala Cys Ala
                405                 410                 415

Lys Ala Ile Lys Glu Gly Ile Ile Pro Pro Thr Ile Asn Tyr Glu Thr
            420                 425                 430

Pro Asp Pro Asp Cys Asp Leu Asp Tyr Val Pro Asn Lys Ala Ile Lys
        435                 440                 445

His Asp Val Asn Val Ala Ile Ser Asp Asn Leu Gly Phe Gly Gly His
    450                 455                 460

Asn Ala Ala Leu Val Phe Lys Lys Tyr Val Ala
465                 470                 475


<210> SEQ ID NO 2
<211> LENGTH: 1428
<212> TYPE: DNA
<213> ORGANISM: Nannochloropsis oculata

<400> SEQUENCE: 2

atgatggaga agctgaccct cgcagtggtg ggctcccttg ccctgacttc ggccttccag      60

ccctcgtcct tcttcctccg gcagacttcc tccgtcagca gcagcagcag cagcagcagg     120
```

actgtgcgtc gtgcatcagg ggaagtgagc atggcggact tgccccgct tgtccgcaag 180 agggtggtga tcacgggtgt cggcgccgtg tctcctctcg ggtggggaga cgacttctgg 240
aacggtctcg tggagggaag gagcggcatt gtccgcctcc cttcgtgggc ggacgagtac 300
cccgcgcgaa tcggaggctt ggtcccggat cactttaagc cgagcgacta catgaatgcc 360
aaggaggtga aacgacaggc ccgcttcacc cattttgcca tggcagctgc ccgtatggcc 420
gtggaagacg ccaagctcga cctggagaag gtggaccgct cgcgtgccgg gtgcatgata 480
ggatccggca ttggtggtgt agaaatcttc gagaaaaact gtggggaatt cgacaagaag 540
ggcggagggc tccctggcct caaggctgtc tccccttcc tgattccggc cctcatcgcc 600
aacaccgcag ccgggacagt ggctattgaa ctcggcttga agggcccgaa ctactgctct 660
gtctccgcct gcgcctcggg cacgcatacc atcggtgatg ccttcttctt cctccaaaac 720
ggcatggcgg acgtttgtgt aacgggcggg acggaagccg ccatcacccc cctctgtttt 780
gcgggatttg tcgccattcg cgcccttacc accagtggca acgacgaccc caccaaggcc 840
tccaagccgt tcgacaagaa ccgagccggt ttcgttatgg ccgagggagc ggggatgctc 900
gtccttgaga cggaggaaca cgcgaaggcc cgaggtgcca ccatctatgc cgagcttgct 960
ggctacggcg catcctgcga cgcccaccac atcaccgccc cccatcccga aggcgagggg 1020
ctggcgaacg cgatgaatat ggctctgacg tccgccggcc tcaagcctac ggacgtggac 1080
tacattaatg cccatggaac cagcacggcc tacaacgaca aattcgagac gctggccatt 1140
caccgcgtct ttggcgagca cgccaagaag ctgaaggttt cttccatcaa gtcaatgact 1200
ggtcactccc tcggggccgc cggtgccttc gaggccgtgg cgtgcgcgaa ggcaatcaag 1260
gagggcatca tcccgcccac catcaactac gagactcccg atccagactg cgacttggac 1320
tatgttccca acaaggcgat caagcacgac gtgaatgtgg ccatctccga taacctgggc 1380
ttcggcgggc acaacgcggc tttggtcttc aagaagtatg ttgcctag 1428

<210> SEQ ID NO 3
<211> LENGTH: 375
<212> TYPE: DNA
<213> ORGANISM: Artificial Sequence
<220> FEATURE:
<223> OTHER INFORMATION: Zeocin resistance gene

<400> SEQUENCE: 3
atggccaagc tgaccagcgc cgttccggtg ctcaccgcgc gcgacgtcgc cggagcggtc 60
gagttctgga ccgaccggct cgggttctcc cgggacttcg tggaggacga cttcgccggt 120
gtggtccggg acgacgtgac cctgttcatc agcgcggtcc aggaccaggt ggtgccggac 180
aacaccctgg cctgggtgtg ggtgcgcggc ctggacgagc tgtacgccga gtggtcggag 240
gtcgtgtcca cgaacttccg ggacgcctcc gggccggcca tgaccgagat cggcgagcag 300
ccgtgggggc gggagttcgc cctgcgcgac ccggccggca actgcgtgca cttcgtggcc 360
gaggagcagg actaa 375

<210> SEQ ID NO 4
<211> LENGTH: 500
<212> TYPE: DNA
<213> ORGANISM: Artificial Sequence
<220> FEATURE:
<223> OTHER INFORMATION: Tubulin promoter

<400> SEQUENCE: 4

```
actgcgcatg gattgaccga cggccggttg ccaacttttg gggtcggccc ccccttttcta     60

gcccttgccc gtccagcaat taaaaattat caacggcata ccggcactgg aagcttcggg    120

tttacaattt tggcttgcct tcctaatact gtaccgcgga gaacgtatga tattacagaa    180

aaatgccttg cacagttagc gcaaagggaa aacgtttctc cgccattgta ctttttggaa    240

gagggaaagc gattgtaaaa tatggctctc cgctacgaga gtttgggctg ttgatacatg    300

tgaaaataag tgtggacgac tttgaatgac ttgatcaggc tgtttgcaca tataaccagc    360

gcgcatgcac ttctgacatg tcaatgacga aatttcacac ttcaccaata aattgtatcc    420

ttacgttttg tctttctcac acgcacatat atgatcatag ataaaagcca atatcaagaa    480

gctgtctttt ttgtgaagca                                                500


<210> SEQ ID NO 5
<211> LENGTH: 1000
<212> TYPE: DNA
<213> ORGANISM: Nannochloropsis oculata

<400> SEQUENCE: 5

tcgggatggg ggaaaaaaac ctctgtgtgg gctgtcagtt gatactatta gaggtctttt     60

gttttgtttg tggctgcgtg tgtgtgtttg catgagaaat agacttgaga atatcggaag    120

gaactttgac atggtaaacg aggaaaagaa aatcttcaaa aaggaataat gggtaaaaac    180

aaggagcacc gggtctcttt agaaatgctt ctcggcggaa aaccagaaaa aaaggtagaa    240

tatgtcgact ttttcgctta tcattataga atgaaagatc gaatggccaa gggatttata    300

aattctttct ttatgttgtc gtagaactta ctttccatcc cgagggaggt gtatgcaggc    360

caaaccctct gacatgggcg caatatctct atgaaaggtt gttggaatac attgtccgac    420

ctccttcgag gcggagccgc atagttgaag tataggtgct tgcttcatcc atctcatgac    480

gctttgccag tgactcactc atgcatgtga cacatttagt tctgctcgct caagcctggc    540

ccctcctgac atgcacacat tgcacttgta ggtgggccac gtttagtata gacgccaccc    600

ctgtcgcacc atcggtccca gagcaggagc acgcttccct actcctgtac gctccccctg    660

cttccccccc tgctcgtcaa cgatggcgac gccagcggct gcgaattaca gtgacggcgc    720

ggccgctcag gatgacagct cctctccttc aacatctccc aatcttccac ccccgcccat    780

gtcgtcgttc gtacggccta tgctgaccga tatgtaccaa attacaatgg tcttcgcgta    840

ctggaagcaa aagcggcacc aggacagggc catctttgag ctctttttcc ggaagacacc    900

ctttaaggga gagtttgcca ttatggccgg cattgacgaa gtactcaagt acttggccca    960

ctttcgcttc tccgaggagg agctgattta tttacgaaag                         1000


<210> SEQ ID NO 6
<211> LENGTH: 800
<212> TYPE: DNA
<213> ORGANISM: Nannochloropsis oculata

<400> SEQUENCE: 6

ttcttccgct tgttgctgcc gatggcggcc atggtctcta agatggagtg gatggaggag     60

gaggcgagcg tagcagcaag cgtgagttat acagccaggc acatgtcgca atccttcggt    120

ctcgggctta aaatccacgc actaatcacg ctgggccatg caaagagcaa tgccgaggcc    180

caccacacaa aacgctgtgt cgcgcgttgc ggcctgaagc ttcatacttc ttagtcgccg    240

ccaaaagggc tcgagagacg agacccgttg gcatgaccga tgttgttcga cgcggtttgc    300

ttcgtcacag tcgacgtgat tcaggaatct ggagcctgca gatcattttt ttcagcctga    360
```

```
tatcgttctt ttccactgag aaccatcaga ccacctttc ttccattgtg tgaaggagta    420

ggagttgccg tgctgctttg tgggagacat ctgcgatggt gaccagcctc ccgtcgtctg    480

gtcgacgtga cgagcctctt cactgttctt cgacggagag acgcaagcga gacggctcta    540

gaccttttgg acacgcattc tgtgtgtgaa ctagtggaca gtgataccac gtctgaaagc    600

tcaccactgc ccatggtgca gctacttgtc acaaagtttt gactccgtcg gtatcaccat    660

tcgcgctcgt gtgcctggtt gttccgccac gccggcctgc cccggggcgg ggcaatattc    720

taaaatctca cgcaaaacac cgcacttacc cctcacacat attcgtgata gaccaccacc    780

aatctcagcc cgcatcaaca                                               800
```

<210> SEQ ID NO 7
<211> LENGTH: 613
<212> TYPE: DNA
<213> ORGANISM: Nannochloropsis oculata

<400> SEQUENCE: 7

```
gcttctgtgg aagagccagt ggtagtagca gtagcagcag cagtagcagc cgcagcactc     60

agtgttggcg cgagagattg tccatccctt cttaacctac cggaagagaa ataaggcctt    120

tctcccgtag ctgtcttcgt ttgtttgtgc tgattgcttg atatgagagt gttgaattcc    180

tgcatcatgt ttttctctgt agtcctttcc tacccccgtc attttctttt ctccctggtt    240

cttcttttgt caccctattt ttacataaaa ttttctttgt ttatagtgag aggaaggtag    300

agaggggaaa acaagaacaa cgaacgcaag cgtgtgaaag gagggcgagt agaagagaaa    360

cagatctgtt gagcattgag agtggagccg gggaaaggc ttgtgtgttg tctttgaaaa    420

agttgtttaa atcacgaatc cgttagttct catgtgtacc tctttcacta catgtgatgg    480

agaaaacaaa agtgtgagga ttaattgaag aaaaagaaga gttcgacacg tcaaaccgcc    540

caaaagacgt cacaaagaga acttgattct ctttgccgtg ttgatcctgt cttttccccc    600

agcttttctt gcc                                                      613
```

<210> SEQ ID NO 8
<211> LENGTH: 37
<212> TYPE: DNA
<213> ORGANISM: Artificial Sequence
<220> FEATURE:
<223> OTHER INFORMATION: PCR primer No. 8

<400> SEQUENCE: 8

```
ctttttgtg aagcaatggc caagttgacc agtgccg                              37
```

<210> SEQ ID NO 9
<211> LENGTH: 36
<212> TYPE: DNA
<213> ORGANISM: Artificial Sequence
<220> FEATURE:
<223> OTHER INFORMATION: PCR primer No. 9

<400> SEQUENCE: 9

```
tttcccccat cccgattagt cctgctcctc ggccac                              36
```

<210> SEQ ID NO 10
<211> LENGTH: 35
<212> TYPE: DNA
<213> ORGANISM: Artificial Sequence
<220> FEATURE:
<223> OTHER INFORMATION: PCR primer No. 10

<400> SEQUENCE: 10
cgagctcggt acccgactgc gcatggattg accga 35

<210> SEQ ID NO 11
<211> LENGTH: 28
<212> TYPE: DNA
<213> ORGANISM: Artificial Sequence
<220> FEATURE:
<223> OTHER INFORMATION: PCR primer No. 11

<400> SEQUENCE: 11
tgcttcacaa aaaagacagc ttcttgat 28

<210> SEQ ID NO 12
<211> LENGTH: 25
<212> TYPE: DNA
<213> ORGANISM: Artificial Sequence
<220> FEATURE:
<223> OTHER INFORMATION: PCR primer No. 12

<400> SEQUENCE: 12
tcgggatggg ggaaaaaaac ctctg 25

<210> SEQ ID NO 13
<211> LENGTH: 36
<212> TYPE: DNA
<213> ORGANISM: Artificial Sequence
<220> FEATURE:
<223> OTHER INFORMATION: PCR primer No. 13

<400> SEQUENCE: 13
actctagagg atcccctttc gtaaataaat cagctc 36

<210> SEQ ID NO 14
<211> LENGTH: 20
<212> TYPE: DNA
<213> ORGANISM: Artificial Sequence
<220> FEATURE:
<223> OTHER INFORMATION: PCR primer No. 14

<400> SEQUENCE: 14
gggatcctct agagtcgacc 20

<210> SEQ ID NO 15
<211> LENGTH: 20
<212> TYPE: DNA
<213> ORGANISM: Artificial Sequence
<220> FEATURE:
<223> OTHER INFORMATION: PCR primer No. 15

<400> SEQUENCE: 15
cgggtaccga gctcgaattc 20

<210> SEQ ID NO 16
<211> LENGTH: 36
<212> TYPE: DNA
<213> ORGANISM: Artificial Sequence
<220> FEATURE:
<223> OTHER INFORMATION: PCR primer No. 16

<400> SEQUENCE: 16
cagcccgcat caacaatgat ggagaagctg accctc 36

<210> SEQ ID NO 17
<211> LENGTH: 37

```
<212> TYPE: DNA
<213> ORGANISM: Artificial Sequence
<220> FEATURE:
<223> OTHER INFORMATION: PCR primer No. 17

<400> SEQUENCE: 17

ctcttccaca gaagcctagg caacatactt cttgaag                              37


<210> SEQ ID NO 18
<211> LENGTH: 35
<212> TYPE: DNA
<213> ORGANISM: Artificial Sequence
<220> FEATURE:
<223> OTHER INFORMATION: PCR primer No. 18

<400> SEQUENCE: 18

cgagctcggt acccgttctt ccgcttgttg ctgcc                                35


<210> SEQ ID NO 19
<211> LENGTH: 25
<212> TYPE: DNA
<213> ORGANISM: Artificial Sequence
<220> FEATURE:
<223> OTHER INFORMATION: PCR primer No. 19

<400> SEQUENCE: 19

tgttgatgcg ggctgagatt ggtgg                                           25


<210> SEQ ID NO 20
<211> LENGTH: 21
<212> TYPE: DNA
<213> ORGANISM: Artificial Sequence
<220> FEATURE:
<223> OTHER INFORMATION: PCR primer No. 20

<400> SEQUENCE: 20

gcttctgtgg aagagccagt g                                               21


<210> SEQ ID NO 21
<211> LENGTH: 28
<212> TYPE: DNA
<213> ORGANISM: Artificial Sequence
<220> FEATURE:
<223> OTHER INFORMATION: PCR primer No. 21

<400> SEQUENCE: 21

ggcaagaaaa gctgggggaa aagacagg                                        28


<210> SEQ ID NO 22
<211> LENGTH: 35
<212> TYPE: DNA
<213> ORGANISM: Artificial Sequence
<220> FEATURE:
<223> OTHER INFORMATION: PCR primer No. 22

<400> SEQUENCE: 22

ccagcttttc ttgccactgc gcatggattg accga                                35


<210> SEQ ID NO 23
<211> LENGTH: 966
<212> TYPE: DNA
<213> ORGANISM: Nannochloropsis oculata

<400> SEQUENCE: 23

aggggaaaga agggagggag ggaagcaagg ggaggcaagg cttgctactg ctcctcctaa     60
```

```
actctcgctc tctttcttct cggtctcacg ccttggcgcg tacacacacc ccaggatcag    120

gaggggacac ggcagaagga ggacctgaaa taatgttgcg gtagaaggaa ggtgggggaa    180

atgaggatgg ttgtatatat gctagagagt gggtattgcg atttcgctgc ctgtttgctg    240

ccggaggctc gccgccgccg catcgtcttg acctatatgc cttcatcgac atggcgagga    300

gggaagtaag acaaacaatg aggccgaggg tttggcatgg aaaaagaaac aggaaccaga    360

ctcatctccg tgtcgtatct ctacaattgc acctcgtgtt ctttcccaag tatcaagttg    420

tcaatgactt cgtcttgaga ctgagacgga cctcctcgct gagcggaaag caagcaaagg    480

aaagatcact cggatgatgc cctgttcttc ccaccacacg tcgacacaaa acccgagccc    540

acgcaccccc aaaccccaag cagcgattgc tgcctggctg cgtcttcgtt cttttttttct    600

gatacgaagc cactttgtct gccgacggcc tggtgtattc tgattctgta ctgtgtgtgt    660

gatgcacgga cgcactacaa acgtgtgcgg gtctcgacca tgtctagtcc cgtcacggcc    720

tttggccttc ggataccgca acagaaagcg aaggaagcat gcagcaaccg acccaacaga    780

cagccaagca gggcaaacca tacctcgtcg ttggcgacga caactctacg cccaggaaga    840

ggaggtgtgg acgcaggcac gcgggtgtct gtgcactttc ctcatgttgt tctcaccctc    900

accaatctct ctcgatttgt cctcacgctt cccctcgccc ctttttcacg cagatcatcg    960

gtcacc                                                                966


<210> SEQ ID NO 24
<211> LENGTH: 362
<212> TYPE: PRT
<213> ORGANISM: Arabidopsis thaliana

<400> SEQUENCE: 24

Met Leu Lys Leu Ser Cys Asn Val Thr Asp Ser Lys Leu Gln Arg Ser
1               5                   10                  15

Leu Leu Phe Phe Ser His Ser Tyr Arg Ser Asp Pro Val Asn Phe Ile
            20                  25                  30

Arg Arg Arg Ile Val Ser Cys Ser Gln Thr Lys Lys Thr Gly Leu Val
        35                  40                  45

Pro Leu Arg Ala Val Val Ser Ala Asp Gln Gly Ser Val Val Gln Gly
    50                  55                  60

Leu Ala Thr Leu Ala Asp Gln Leu Arg Leu Gly Ser Leu Thr Glu Asp
65                  70                  75                  80

Gly Leu Ser Tyr Lys Glu Lys Phe Val Val Arg Ser Tyr Glu Val Gly
                85                  90                  95

Ser Asn Lys Thr Ala Thr Val Glu Thr Ile Ala Asn Leu Leu Gln Glu
            100                 105                 110

Val Gly Cys Asn His Ala Gln Ser Val Gly Phe Ser Thr Asp Gly Phe
        115                 120                 125

Ala Thr Thr Thr Thr Met Arg Lys Leu His Leu Ile Trp Val Thr Ala
    130                 135                 140

Arg Met His Ile Glu Ile Tyr Lys Tyr Pro Ala Trp Gly Asp Val Val
145                 150                 155                 160

Glu Ile Glu Thr Trp Cys Gln Ser Glu Gly Arg Ile Gly Thr Arg Arg
                165                 170                 175

Asp Trp Ile Leu Lys Asp Ser Val Thr Gly Glu Val Thr Gly Arg Ala
            180                 185                 190

Thr Ser Lys Trp Val Met Met Asn Gln Asp Thr Arg Arg Leu Gln Lys
        195                 200                 205
```

```
Val Ser Asp Asp Val Arg Asp Glu Tyr Leu Val Phe Cys Pro Gln Glu
    210                 215                 220

Pro Arg Leu Ala Phe Pro Glu Glu Asn Asn Arg Ser Leu Lys Lys Ile
225                 230                 235                 240

Pro Lys Leu Glu Asp Pro Ala Gln Tyr Ser Met Ile Gly Leu Lys Pro
                245                 250                 255

Arg Arg Ala Asp Leu Asp Met Asn Gln His Val Asn Asn Val Thr Tyr
            260                 265                 270

Ile Gly Trp Val Leu Glu Ser Ile Pro Gln Glu Ile Val Asp Thr His
        275                 280                 285

Glu Leu Gln Val Ile Thr Leu Asp Tyr Arg Arg Glu Cys Gln Gln Asp
    290                 295                 300

Asp Val Val Asp Ser Leu Thr Thr Thr Thr Ser Glu Ile Gly Gly Thr
305                 310                 315                 320

Asn Gly Ser Ala Thr Ser Gly Thr Gln Gly His Asn Asp Ser Gln Phe
                325                 330                 335

Leu His Leu Leu Arg Leu Ser Gly Asp Gly Gln Glu Ile Asn Arg Gly
            340                 345                 350

Thr Thr Leu Trp Arg Lys Lys Pro Ser Ser
        355                 360


<210> SEQ ID NO 25
<211> LENGTH: 412
<212> TYPE: PRT
<213> ORGANISM: Arabidopsis thaliana

<400> SEQUENCE: 25

Met Val Ala Thr Ser Ala Thr Ser Ser Phe Phe Pro Val Pro Ser Ser
1               5                   10                  15

Ser Leu Asp Pro Asn Gly Lys Gly Asn Lys Ile Gly Ser Thr Asn Leu
            20                  25                  30

Ala Gly Leu Asn Ser Ala Pro Asn Ser Gly Arg Met Lys Val Lys Pro
        35                  40                  45

Asn Ala Gln Ala Pro Pro Lys Ile Asn Gly Lys Lys Val Gly Leu Pro
    50                  55                  60

Gly Ser Val Asp Ile Val Arg Thr Asp Thr Glu Thr Ser Ser His Pro
65                  70                  75                  80

Ala Pro Arg Thr Phe Ile Asn Gln Leu Pro Asp Trp Ser Met Leu Leu
                85                  90                  95

Ala Ala Ile Thr Thr Ile Phe Leu Ala Ala Glu Lys Gln Trp Met Met
            100                 105                 110

Leu Asp Trp Lys Pro Arg Arg Ser Asp Met Leu Val Asp Pro Phe Gly
        115                 120                 125

Ile Gly Arg Ile Val Gln Asp Gly Leu Val Phe Arg Gln Asn Phe Ser
    130                 135                 140

Ile Arg Ser Tyr Glu Ile Gly Ala Asp Arg Ser Ala Ser Ile Glu Thr
145                 150                 155                 160

Val Met Asn His Leu Gln Glu Thr Ala Leu Asn His Val Lys Thr Ala
                165                 170                 175

Gly Leu Leu Gly Asp Gly Phe Gly Ser Thr Pro Glu Met Phe Lys Lys
            180                 185                 190

Asn Leu Ile Trp Val Val Thr Arg Met Gln Val Val Val Asp Lys Tyr
        195                 200                 205

Pro Thr Trp Gly Asp Val Val Glu Val Asp Thr Trp Val Ser Gln Ser
    210                 215                 220
```

```
Gly Lys Asn Gly Met Arg Arg Asp Trp Leu Val Arg Asp Cys Asn Thr
225                 230                 235                 240

Gly Glu Thr Leu Thr Arg Ala Ser Ser Val Trp Val Met Met Asn Lys
                245                 250                 255

Leu Thr Arg Arg Leu Ser Lys Ile Pro Glu Glu Val Arg Gly Glu Ile
            260                 265                 270

Glu Pro Tyr Phe Val Asn Ser Asp Pro Val Leu Ala Glu Asp Ser Arg
        275                 280                 285

Lys Leu Thr Lys Ile Asp Asp Lys Thr Ala Asp Tyr Val Arg Ser Gly
    290                 295                 300

Leu Thr Pro Arg Trp Ser Asp Leu Asp Val Asn Gln His Val Asn Asn
305                 310                 315                 320

Val Lys Tyr Ile Gly Trp Ile Leu Glu Ser Ala Pro Val Gly Ile Met
                325                 330                 335

Glu Arg Gln Lys Leu Lys Ser Met Thr Leu Glu Tyr Arg Arg Glu Cys
            340                 345                 350

Gly Arg Asp Ser Val Leu Gln Ser Leu Thr Ala Val Thr Gly Cys Asp
        355                 360                 365

Ile Gly Asn Leu Ala Thr Ala Gly Asp Val Glu Cys Gln His Leu Leu
    370                 375                 380

Arg Leu Gln Asp Gly Ala Glu Val Val Arg Gly Arg Thr Glu Trp Ser
385                 390                 395                 400

Ser Lys Thr Pro Thr Thr Thr Trp Gly Thr Ala Pro
                405                 410


<210> SEQ ID NO 26
<211> LENGTH: 352
<212> TYPE: PRT
<213> ORGANISM: Garcinia mangostana

<400> SEQUENCE: 26

Met Leu Lys Leu Ser Ser Ser Arg Ser Pro Leu Ala Arg Ile Pro Thr
1               5                   10                  15

Arg Pro Arg Pro Asn Ser Ile Pro Pro Arg Ile Ile Val Val Ser Ser
            20                  25                  30

Ser Ser Ser Lys Val Asn Pro Leu Lys Thr Glu Ala Val Val Ser Ser
        35                  40                  45

Gly Leu Ala Asp Arg Leu Arg Leu Gly Ser Leu Thr Glu Asp Gly Leu
    50                  55                  60

Ser Tyr Lys Glu Lys Phe Ile Val Arg Cys Tyr Glu Val Gly Ile Asn
65                  70                  75                  80

Lys Thr Ala Thr Val Glu Thr Ile Ala Asn Leu Leu Gln Glu Val Gly
                85                  90                  95

Cys Asn His Ala Gln Ser Val Gly Tyr Ser Thr Gly Gly Phe Ser Thr
            100                 105                 110

Thr Pro Thr Met Arg Lys Leu Arg Leu Ile Trp Val Thr Ala Arg Met
        115                 120                 125

His Ile Glu Ile Tyr Lys Tyr Pro Ala Trp Ser Asp Val Val Glu Ile
    130                 135                 140

Glu Ser Trp Gly Gln Gly Glu Gly Lys Ile Gly Thr Arg Arg Asp Trp
145                 150                 155                 160

Ile Leu Arg Asp Tyr Ala Thr Gly Gln Val Ile Gly Arg Ala Thr Ser
                165                 170                 175

Lys Trp Val Met Met Asn Gln Asp Thr Arg Arg Leu Gln Lys Val Asp
```

```
            180                 185                 190

Val Asp Val Arg Asp Glu Tyr Leu Val His Cys Pro Arg Glu Leu Arg
        195                 200                 205

Leu Ala Phe Pro Glu Glu Asn Asn Ser Ser Leu Lys Lys Ile Ser Lys
    210                 215                 220

Leu Glu Asp Pro Ser Gln Tyr Ser Lys Leu Gly Leu Val Pro Arg Arg
225                 230                 235                 240

Ala Asp Leu Asp Met Asn Gln His Val Asn Asn Val Thr Tyr Ile Gly
                245                 250                 255

Trp Val Leu Glu Ser Met Pro Gln Glu Ile Ile Asp Thr His Glu Leu
            260                 265                 270

Gln Thr Ile Thr Leu Asp Tyr Arg Arg Glu Cys Gln His Asp Asp Val
        275                 280                 285

Val Asp Ser Leu Thr Ser Pro Glu Pro Ser Glu Asp Ala Glu Ala Val
    290                 295                 300

Phe Asn His Asn Gly Thr Asn Gly Ser Ala Asn Val Ser Ala Asn Asp
305                 310                 315                 320

His Gly Cys Arg Asn Phe Leu His Leu Leu Arg Leu Ser Gly Asn Gly
                325                 330                 335

Leu Glu Ile Asn Arg Gly Arg Thr Glu Trp Arg Lys Lys Pro Thr Arg
            340                 345                 350


<210> SEQ ID NO 27
<211> LENGTH: 274
<212> TYPE: PRT
<213> ORGANISM: Nannochloropsis gaditana

<400> SEQUENCE: 27

Met Leu Cys Cys Ala Cys Lys Ser Val His Ala Thr Ile Ser Val Ala
1               5                   10                  15

Phe Ile Gly Thr Arg Lys Pro His Arg Leu Pro Ala Leu Phe Pro Leu
            20                  25                  30

Phe Leu Ala Pro Ala Arg Ala Leu Ser His Gln Glu Pro Asn Pro Ala
        35                  40                  45

Thr Cys Gly Thr Gln Asn Ser Ser Phe Ser Ile Leu Leu Lys Thr Val
    50                  55                  60

Val Ala Gly Ser Phe Val Gly Ala Ala Phe Ile Ala Gly His Thr Ala
65                  70                  75                  80

Gly Ala Ser Cys Asp Glu Val Lys Ser Pro Gln Glu Val Asn Asn Val
                85                  90                  95

Gly Gly Gly Ala Pro Val Thr Ala Pro Tyr Thr Val Thr Phe Ala Ser
            100                 105                 110

Asn Tyr His Asp Arg Val Asp Thr Lys Leu His Arg Ala Tyr Pro Glu
        115                 120                 125

Phe Leu Gln Tyr His Leu Ile His Glu Thr Leu Arg Gly Lys Glu Lys
    130                 135                 140

Ile Glu Gly Tyr Glu Val Tyr Lys Asp Arg Arg Asp Asp Ser Ile Val
145                 150                 155                 160

Ala Phe Ala Arg Leu Gly Lys Leu Leu Ser Gly His Pro Asp Ile Ile
                165                 170                 175

His Gly Gly Ser Ile Ala Ala Leu Leu Asp Asn Thr Met Gly Val Ala
            180                 185                 190

Phe Phe Ala Ala Asn Lys Gly Asn Gly Phe Thr Ala Asn Leu Thr Ile
        195                 200                 205
```

```
Asn Tyr Lys Arg Pro Ile Ile Cys Gly Thr Glu Ile Lys Val Leu Ala
    210                 215                 220

Arg Val Glu Arg Phe Glu Gly Arg Lys Val Phe Leu Arg Ala Glu Ile
225                 230                 235                 240

Arg Asp Ala Lys Asp Glu Ala Val Leu Tyr Thr Glu Ala Thr Ser Leu
                245                 250                 255

Phe Ile Thr Ser Gln Ser Pro Leu Leu Thr Gly Pro Lys Lys Val Asp
            260                 265                 270

Ile Ser


<210> SEQ ID NO 28
<211> LENGTH: 287
<212> TYPE: PRT
<213> ORGANISM: Nannochloropsis oculata

<400> SEQUENCE: 28

Met Thr Pro Leu Ala Phe Thr Val Leu Gly Lys Leu Gly Gly Thr Leu
1               5                   10                  15

Thr Phe Ala Cys Val Arg Arg Arg Leu Tyr His Leu Leu Arg Arg Ala
            20                  25                  30

Thr Leu Ser Ser His Tyr Gln Val Thr Arg Pro Tyr Gly His Ser Asn
        35                  40                  45

Ser Gly Cys Ser His Ser Thr Thr Thr Leu Arg Thr Ser Phe Pro Val
    50                  55                  60

Leu Phe Ala Gln Leu Ala Ala Ala Thr Ala Ala Val Val Ala Ala Ile
65                  70                  75                  80

Ser Leu Pro Ser Pro Ser Leu Cys Glu Thr Ala His Ala Gly Thr Glu
                85                  90                  95

Glu Arg Arg Gly Glu Arg Lys Ala Met Arg Glu Asp Gly Gly Lys Gly
            100                 105                 110

Glu Ala Thr Ser Ser Ala Thr Cys Asn Pro Ser Leu Phe Glu His His
        115                 120                 125

Asp Arg Val Asp Thr Lys Leu His Arg Ala Tyr Pro Glu Phe Leu Lys
    130                 135                 140

Phe His Leu Ile His Glu Thr Leu Arg Gly Lys Glu Lys Ile Asp Gly
145                 150                 155                 160

Tyr Glu Val Tyr Lys Asp Arg Arg Asp Asp Ser Ile Val Ala Tyr Ala
                165                 170                 175

Arg Leu Gly Lys Leu Leu Ser Gly His Pro Asp Ile Ile His Gly Gly
            180                 185                 190

Ser Ile Ala Ala Leu Leu Asp Asn Thr Met Gly Val Ala Phe Phe Ala
        195                 200                 205

Ala Lys Arg Gly Asn Gly Phe Thr Ala Asn Leu Thr Ile Asn Tyr Lys
    210                 215                 220

Arg Pro Ile Thr Cys Gly Thr Glu Val Lys Val Leu Ala Arg Val Glu
225                 230                 235                 240

Lys Val Glu Gly Arg Lys Val Phe Leu Arg Ala Glu Ile Arg Asp Ala
                245                 250                 255

Lys Asp Glu Ala Ile Leu Tyr Thr Glu Ala Lys Ser Leu Phe Ile Thr
            260                 265                 270

Ser Gln Ser Pro Leu Leu Lys Gly Pro Lys Lys Ile Asp Ile Ser
        275                 280                 285


<210> SEQ ID NO 29
<211> LENGTH: 285
```

```
<212> TYPE: PRT
<213> ORGANISM: Nannochloropsis granulata

<400> SEQUENCE: 29

Met Thr Pro Leu Ala Phe Thr Ala Leu Gly Glu Val Gly Gly Met Leu
1               5                   10                  15

Ala Ala Ala Cys Val Arg Arg Lys Leu His His Leu Leu Arg Arg Ala
            20                  25                  30

Ala Ser Ser Ser Gln Val Thr Arg Pro Tyr Ser His Ser Thr Ala Asn
        35                  40                  45

Ser Thr His Ser Thr Thr Thr Leu Ser Asn Ser Phe Pro Val Leu Phe
    50                  55                  60

Ala Gln Leu Ala Ala Ala Ala Ala Ala Val Met Ala Ala Thr Ser Leu
65                  70                  75                  80

Ser Ser Pro Ser Leu Cys Glu Thr Ala His Thr Asn Thr Glu Glu Arg
                85                  90                  95

Gly Gly Glu Gly Glu Ala Met Arg Glu Lys Gly Gly Glu Gly Glu Ala
            100                 105                 110

Thr Ser Ser Ala Thr Cys Ala Pro Ser Phe Phe Glu His His Asp Arg
        115                 120                 125

Val Asp Thr Lys Leu His Arg Ala Tyr Pro Glu Phe Leu Lys Phe His
    130                 135                 140

Leu Ile His Glu Thr Leu Arg Gly Lys Glu Lys Ile Asp Gly Tyr Glu
145                 150                 155                 160

Val Tyr Lys Asn Arg Arg Asp Asp Ser Val Val Ala Tyr Ala Arg Leu
                165                 170                 175

Gly Lys Leu Leu Ser Gly His Pro Asp Ile Ile His Gly Gly Ser Ile
            180                 185                 190

Ala Ala Leu Leu Asp Asn Thr Met Gly Val Ala Phe Phe Ala Ala Lys
        195                 200                 205

Arg Gly Asn Gly Phe Thr Ala Asn Leu Thr Ile Asn Tyr Lys Arg Pro
    210                 215                 220

Ile Thr Cys Gly Thr Glu Val Lys Val Leu Ala Arg Val Glu Lys Val
225                 230                 235                 240

Glu Gly Arg Lys Val Phe Leu Arg Ala Glu Ile Arg Asp Ala Lys Asp
                245                 250                 255

Glu Ala Ile Leu Tyr Thr Glu Ala Asn Ser Leu Phe Ile Thr Ser Gln
            260                 265                 270

Ser Pro Leu Leu Lys Gly Pro Lys Lys Ile Asp Ile Ser
        275                 280                 285


<210> SEQ ID NO 30
<211> LENGTH: 348
<212> TYPE: PRT
<213> ORGANISM: Nannochloropsis oculata

<400> SEQUENCE: 30

Met Arg Ile Pro Ser Leu Ile Leu Cys Phe Ala Phe Leu Ala Ser Ala
1               5                   10                  15

Pro Ala Val Ala Phe Leu Leu Pro Pro Leu Pro Cys Phe Ser Ser Ser
            20                  25                  30

Leu Gln Thr Val Thr Asn Thr Ile Thr Thr Ser Ser Arg Phe Ser Ser
        35                  40                  45

Ser Ser Ser Ser Ser Ser Ser Ser Ser Ser Ser Ser Ser Arg Pro Arg
    50                  55                  60
```

```
Cys Ser Pro Leu Leu Ser Val Thr Thr Ala Ala Thr Ala Ser Ser Ala
65                  70                  75                  80

Thr Glu Glu Ala Glu Asn Pro Ser Leu Thr Gln Gly Val Phe Ile Glu
                85                  90                  95

His Thr Asp Arg Tyr Gly Met Val Tyr His Ser Asn Tyr Leu Leu Phe
            100                 105                 110

Leu Cys Arg Ala Leu His Leu Thr Leu Gly Arg His Val Val Thr Arg
        115                 120                 125

Leu Asp Asn Phe Arg Phe Lys Ala Ser Ala Arg Leu Gly His Asp Ile
    130                 135                 140

Ala Ile Asp Val Arg Pro Lys Ala Gly Lys Asp Asn Thr Phe Val Thr
145                 150                 155                 160

Ser Ile Lys Glu Ser Glu Thr Pro His Thr Thr Phe Ile Thr Ala Asp
                165                 170                 175

Val Ser Ala Phe Pro Leu Pro Glu Arg Gly Arg Glu Gly Gly Arg Glu
            180                 185                 190

Asp Trp Ala Ala Tyr Thr Ile Ser Glu Glu Glu Ala Leu Arg Lys Val
        195                 200                 205

Val Ala Ser Pro Asp Lys Val Met Glu Ala Val Leu Trp Thr Asp Glu
    210                 215                 220

Leu Gly Val His Gly Leu Leu Thr Pro His Ala Val Leu Ser Leu Phe
225                 230                 235                 240

Glu Arg Gly Arg Ser Asp Ser Leu Gly Gly Pro Asp Arg Leu Glu Glu
                245                 250                 255

Leu Met Asp Asp Gly Tyr Met Phe Val Val Ala Arg Ile Asp Gly Tyr
            260                 265                 270

Arg Phe Asp Pro Ser Leu Arg Leu Glu Glu Gly Glu Ala Leu Gln Val
        275                 280                 285

Leu Gly Arg Phe Lys Pro Lys Ser Asp Ala Ile Val Val Cys Glu Gln
    290                 295                 300

Val Leu Ile Val Lys Ala Thr Gln Gln Ile Val Ala Gln Ala Leu Val
305                 310                 315                 320

Thr Leu Ala Cys Ile Gly Ala Val Asp Gly Lys Leu Arg Gly Val Pro
                325                 330                 335

Ser Lys Ala Leu Glu Ser Met Asn Met Gly Thr Thr
            340                 345


<210> SEQ ID NO 31
<211> LENGTH: 208
<212> TYPE: PRT
<213> ORGANISM: Escherichia coli

<400> SEQUENCE: 31

Met Met Asn Phe Asn Asn Val Phe Arg Trp His Leu Pro Phe Leu Phe
1               5                   10                  15

Leu Val Leu Leu Thr Phe Arg Ala Ala Ala Ala Asp Thr Leu Leu Ile
            20                  25                  30

Leu Gly Asp Ser Leu Ser Ala Gly Tyr Arg Met Ser Ala Ser Ala Ala
        35                  40                  45

Trp Pro Ala Leu Leu Asn Asp Lys Trp Gln Ser Lys Thr Ser Val Val
    50                  55                  60

Asn Ala Ser Ile Ser Gly Asp Thr Ser Gln Gln Gly Leu Ala Arg Leu
65                  70                  75                  80

Pro Ala Leu Leu Lys Gln His Gln Pro Arg Trp Val Leu Val Glu Leu
                85                  90                  95
```

```
Gly Gly Asn Asp Gly Leu Arg Gly Phe Gln Pro Gln Gln Thr Glu Gln
            100                 105                 110

Thr Leu Arg Gln Ile Leu Gln Asp Val Lys Ala Ala Asn Ala Glu Pro
        115                 120                 125

Leu Leu Met Gln Ile Arg Leu Pro Ala Asn Tyr Gly Arg Arg Tyr Asn
    130                 135                 140

Glu Ala Phe Ser Ala Ile Tyr Pro Lys Leu Ala Lys Glu Phe Asp Val
145                 150                 155                 160

Pro Leu Leu Pro Phe Phe Met Glu Glu Val Tyr Leu Lys Pro Gln Trp
                165                 170                 175

Met Gln Asp Asp Gly Ile His Pro Asn Arg Asp Ala Gln Pro Phe Ile
            180                 185                 190

Ala Asp Trp Met Ala Lys Gln Leu Gln Pro Leu Val Asn His Asp Ser
        195                 200                 205


<210> SEQ ID NO 32
<211> LENGTH: 438
<212> TYPE: PRT
<213> ORGANISM: Nannochloropsis oculata

<400> SEQUENCE: 32

Met Gly Arg Gly Gly Glu Lys Thr Val Thr Pro Leu Arg Lys Lys Thr
1               5                   10                  15

Leu Leu Asp Ala Ala Ser Thr Ile Ser Gly Thr Val Arg Pro Ser Lys
            20                  25                  30

Ala Val Glu Ala Leu Pro Thr Glu Glu Leu Arg Lys Lys Ala Ala Gln
        35                  40                  45

Tyr Gly Ile Asn Thr Ser Val Asp Arg Glu Thr Leu Leu Arg Glu Leu
    50                  55                  60

Ala Pro Tyr Gly Asp Ile Leu Leu Arg Asn Asp Ala Pro Lys Ser Leu
65                  70                  75                  80

Pro Leu Ala Pro Pro Pro Phe Thr Leu Ser Asp Ile Lys Asn Ala Val
                85                  90                  95

Pro Arg His Cys Phe Glu Arg Ser Leu Ser Thr Ser Leu Phe His Leu
            100                 105                 110

Thr Ile Asp Leu Ile Gln Val Ala Val Leu Gly Tyr Leu Ala Ser Leu
        115                 120                 125

Leu Gly His Ser Asp Val Pro Pro Met Ser Arg Tyr Ile Leu Trp Pro
    130                 135                 140

Leu Tyr Trp Tyr Ala Gln Gly Ser Val Leu Thr Gly Val Trp Val Ile
145                 150                 155                 160

Ala His Glu Cys Gly His Gln Ser Phe Ser Pro Tyr Glu Ser Val Asn
                165                 170                 175

Asn Phe Phe Gly Trp Leu Leu His Ser Ala Leu Leu Val Pro Tyr His
            180                 185                 190

Ser Trp Arg Ile Ser His Gly Lys His His Asn Asn Thr Gly Ser Cys
        195                 200                 205

Glu Asn Asp Glu Val Phe Ala Pro Pro Ile Lys Glu Glu Leu Met Asp
    210                 215                 220

Glu Ile Leu Leu His Ser Pro Leu Ala Asn Leu Val Gln Ile Ile Ile
225                 230                 235                 240

Met Leu Thr Ile Gly Trp Met Pro Gly Tyr Leu Leu Leu Asn Ala Thr
                245                 250                 255

Gly Pro Arg Lys Tyr Lys Gly Leu Ser Asn Ser His Phe Asn Pro Asn
```

```
            260                 265                 270

Ser Ala Leu Phe Ser Pro Lys Asp Arg Leu Asp Ile Ile Trp Ser Asp
        275                 280                 285

Ile Gly Phe Phe Val Ala Leu Ala Cys Val Val Tyr Ala Cys Val Gln
    290                 295                 300

Phe Gly Phe Gln Thr Val Gly Lys Tyr Tyr Leu Leu Pro Tyr Met Val
305                 310                 315                 320

Val Asn Tyr His Leu Val Leu Ile Thr Tyr Leu Gln His Thr Asp Val
                325                 330                 335

Phe Ile Pro His Phe Arg Gly Ser Glu Trp Thr Trp Phe Arg Gly Ala
            340                 345                 350

Leu Cys Thr Val Asp Arg Ser Phe Gly Trp Leu Leu Asp His Thr Phe
        355                 360                 365

His His Ile Ser Asp Thr His Val Cys His His Ile Phe Ser Lys Met
    370                 375                 380

Pro Phe Tyr His Ala Gln Glu Ala Ser Glu His Ile Arg Lys Ala Leu
385                 390                 395                 400

Gly Asp Tyr Tyr Leu Lys Asp Asp Thr Pro Ile Trp Lys Ala Leu Trp
                405                 410                 415

Arg Ser Tyr Thr Leu Cys Lys Tyr Val Asp Ser Glu Glu Thr Thr Val
            420                 425                 430

Phe Tyr Lys Gln Arg Ala
        435


<210> SEQ ID NO 33
<211> LENGTH: 1317
<212> TYPE: DNA
<213> ORGANISM: Nannochloropsis oculata

<400> SEQUENCE: 33

atgggacgcg gcggtgagaa gacggtgacc cctcttcgca aaaaaaccct cctggatgcc      60

gcttccacga tcagcggcac agtcagacca agcaaggcag tagaggccct gcccacggag     120

gagctgcgta agaaggccgc acaatacggt atcaacactt cggtcgaccg cgaaacactg     180

ctgagggagc tggctcccta cggcgatatc ctcctccgca atgacgcccc taaatccctg     240

ccccttgccc ctcctccttt caccctctcc gacatcaaga acgctgttcc ccgtcactgc     300

tttgagcgtt ccctctccac ctccctcttc cacttgacca tcgacttgat ccaagtcgct     360

gtcctcgggt accttgcctc attactgggc cactccgacg tcccgcccat gtctcgttat     420

attctatggc cgttgtactg gtacgcgcaa ggctctgtgc tgacgggagt gtgggtcatt     480

gcccacgagt gcgggcacca atcgttttcg ccttacgaga gcgtgaacaa cttctttggg     540

tggctcttgc actcggcctt gcttgtgccc tatcactctt ggaggatttc ccatggaaag     600

caccacaaca acacggggag ctgcgagaat gacgaggtct ttgcgccgcc tattaaggag     660

gaactgatgg acgagatttt gcttcactcc cctttggcga atctggtgca gataatcata     720

atgttgacca tcggatggat gccggggtac ctgctcctga acgctacggg gcctaggaaa     780

tacaagggac tgagcaatag ccactttaac ccaaattcgg cgttgttttc tccgaaggac     840

cgtctggaca ttatttggtc cgacattggg tttttcgtgg ccttggcctg cgtggtatat     900

gcctgtgtgc agtttggatt tcaaacggtg ggaaagtatt acctgctgcc gtacatggtg     960

gtcaattatc acctggtcct catcacgtac ctgcagcaca cggacgtctt catccccac     1020

tttcgggga gcgagtggac gtggtttagg ggcgcccttt gcacggtcga ccgatccttc     1080
```

```
ggctggcttt tggaccatac gtttcaccat atcagtgaca ctcatgtgtg ccaccacatc   1140

ttcagcaaga tgccgttcta ccacgcgcag gaggcgagtg agcacattcg caaggcgttg   1200

ggcgactatt atttgaagga tgataccccg atttggaagg cattgtggcg aagttatacc   1260

ctgtgcaagt acgtggactc ggaggagacg acggtattct acaagcagcg ggcatag      1317
```

<210> SEQ ID NO 34
<211> LENGTH: 452
<212> TYPE: PRT
<213> ORGANISM: Nannochloropsis gaditana

<400> SEQUENCE: 34

```
Met Gly Arg Gly Gly Glu Lys Thr Val Thr Pro Pro Ser Lys Ser Phe
1               5                   10                  15

His Ala His Gly His Ser Leu Thr Ala Ser Asp Leu Ser Arg Ala Asp
            20                  25                  30

Ala Ala Ser Thr Ile Ser Ser Ser Val Arg Pro Ser Lys Ser Leu Glu
        35                  40                  45

Ala Met Pro Thr Glu Glu Leu Arg Lys Lys Ala Leu Gln Tyr Gly His
    50                  55                  60

Asp Ala Ser Ala Asp Arg Ala Ser Leu Leu Gln Ile Leu Ala Pro Tyr
65                  70                  75                  80

Gly Asp Ile Leu Leu Arg Thr Asp Ala Pro Pro Ser Leu Pro Leu Ala
                85                  90                  95

Pro Pro Pro Phe Thr Leu Ala Asp Ile Lys Ala Ala Val Pro Arg His
            100                 105                 110

Cys Phe Glu Arg Ser Leu Thr Thr Ser Phe Phe His Leu Ala Cys Asp
        115                 120                 125

Leu Val Leu Val Ala Leu Leu Gly Tyr Leu Ala Thr Leu Ile Gly His
    130                 135                 140

Pro Asp Val Pro Thr Met Ser Arg Tyr Leu Leu Trp Pro Leu Tyr Trp
145                 150                 155                 160

Tyr Ala Gln Gly Ser Val Leu Thr Gly Val Trp Val Ile Ala His Glu
                165                 170                 175

Cys Gly His Gln Ser Phe Ser Pro Tyr Glu Arg Val Asn Asn Leu Val
            180                 185                 190

Gly Trp Val Leu His Ser Ala Leu Leu Val Pro Tyr His Ser Trp Arg
        195                 200                 205

Ile Ser His Gly Lys His His Asn Asn Thr Gly Ser Cys Glu Asn Asp
    210                 215                 220

Glu Val Phe Ala Pro Pro Ile Lys Glu Asp Leu Met Asp Glu Ile Leu
225                 230                 235                 240

Leu His Ser Pro Leu Ala Asn Leu Ala Gln Ile Ile Ile Met Leu Thr
                245                 250                 255

Val Gly Trp Met Pro Gly Tyr Leu Leu Met Asn Ala Thr Gly Pro Arg
            260                 265                 270

Lys Tyr Lys Gly Lys Asn Asn Ser His Phe Asp Pro Asn Ser Ala Leu
        275                 280                 285

Phe Ser Pro Lys Asp Arg Leu Asp Ile Ile Trp Ser Asp Ile Gly Phe
    290                 295                 300

Phe Leu Ala Leu Ala Gly Val Val Trp Ala Cys Thr Gln Tyr Gly Phe
305                 310                 315                 320

Ser Thr Val Gly Lys Tyr Tyr Leu Leu Pro Tyr Met Val Val Asn Tyr
                325                 330                 335
```

-continued

```
His Leu Val Leu Ile Thr Tyr Leu Gln His Thr Asp Val Phe Ile Pro
            340                 345                 350

His Phe Arg Gly Ala Glu Trp Ser Trp Phe Arg Gly Ala Leu Cys Thr
        355                 360                 365

Val Asp Arg Ser Phe Gly Trp Leu Leu Asp His Thr Phe His His Ile
    370                 375                 380

Ser Asp Thr His Val Cys His His Ile Phe Ser Lys Met Pro Phe Tyr
385                 390                 395                 400

His Ala Gln Glu Ala Ser Glu His Ile Lys Lys Ala Leu Gly Pro Tyr
                405                 410                 415

Tyr Leu Lys Asp Asp Thr Pro Ile Trp Lys Ala Leu Trp Arg Ser Tyr
            420                 425                 430

Thr Leu Cys Lys Tyr Val Asp Thr Asp Lys Asn Ala Val Phe Tyr Lys
        435                 440                 445

His Arg Ala Ser
    450


<210> SEQ ID NO 35
<211> LENGTH: 1359
<212> TYPE: DNA
<213> ORGANISM: Nannochloropsis gaditana

<400> SEQUENCE: 35

atggggcgtg gcggtgagaa aactgtcaca cctccatcaa aatccttcca tgctcatggc      60

cactctctga ccgccagtga cctttctcga gcggatgccg catccactat ctcgagctcg     120

gttaggccca gtaagtcgtt ggaggcaatg cccacggaag aattgcgaaa gaaggcactg     180

caatacggac acgacgcctc cgcggacagg gcctcgttgc ttcaaatact ggccccatat     240

ggcgacattc ttcttcgtac ggacgcgcct ccctccctcc ccctcgcccc tcctcccttc     300

acccttgcgg atatcaaagc cgccgtaccc aggcattgct tcgaacgctc cttgaccacc     360

tccttcttcc acctcgcttg tgacctcgtc ctggttgctc tgctcggata cttggccacg     420

ctcatcgggc acccggacgt gccgaccatg tcccgctacc tactgtggcc tctctactgg     480

tacgcgcagg gctcggtgct gacaggcgtg tgggtcattg cccatgaatg tgggcatcag     540

tctttttccc cgtacgaacg ggtgaacaac ctggtggggt gggtcctgca ctccgccctc     600

ctcgtcccgt accattcctg gcgcatctcc cacggcaagc accacaacaa cacggggagc     660

tgcgagaacg acgaggtgtt cgcgccgcca atcaaggaag acctgatgga cgagatcctc     720

ctccactccc ccttggccaa cctcgcccaa atcatcatca tgttgaccgt gggatggatg     780

cccggctacc tgttgatgaa tgccacggga cctcgaaagt acaagggcaa gaacaacagc     840

cacttcgatc cgaattcggc gctgttctcc cccaaggacc gcttggatat catctggtcg     900

gacataggct tcttcctcgc tttggccggc gtggtgtggg cctgcaccca gtacgggttc     960

tccacggtgg gcaagtacta cctgctcccc tacatggtgg tgaactatca cctggtgctc    1020

atcacctatc tccagcacac ggacgtcttc atccctcatt tccgcggggc agagtggtca    1080

tggttccggg gggctctttg cactgtcgac cgctccttcg gctggctgct cgaccatacg    1140

ttccaccaca tctcggacac gcacgtctgc catcatatct ttagtaagat gcctttctat    1200

cacgcgcaag aagcgagtga gcacatcaag aaggcgctgg ggccgtacta cctgaaggac    1260

gacaccccga tatggaaagc gttgtggcga agttatacgc tttgcaagta tgtggacacg    1320

gataaaaatg ccgtttttta caagcaccga gcatcatag                             1359
```

```
<210> SEQ ID NO 36
<211> LENGTH: 474
<212> TYPE: PRT
<213> ORGANISM: Nannochloropsis oculata

<400> SEQUENCE: 36

Met Gly Arg Gly Gly Glu Arg Val Glu Thr Thr Glu Ser Leu Ser Phe
1               5                   10                  15

Thr Ala Asp Lys Ala Gly Thr Ile Lys Gln Arg Gly Gly Lys Ile Thr
            20                  25                  30

Trp Asp Glu Val Arg Gln His Lys Thr Pro Gln Asp Ala Trp Leu Val
        35                  40                  45

Tyr Arg Asn Lys Val Tyr Asp Val Ser Gly Trp Gln Asp His Pro Gly
    50                  55                  60

Gly Asn Val Ile Phe Thr His Ala Gly Gly Asp Cys Thr Asp Ile Phe
65                  70                  75                  80

Ala Ala Phe His Pro Leu Gly Ala Thr Ser Tyr Leu Asp Pro Phe Tyr
                85                  90                  95

Ile Gly Glu Leu Glu Pro Gly Ser Asp Lys Lys Pro Ala Ala Gln Ala
            100                 105                 110

Asn Phe Glu Arg Ala Tyr Arg Asp Leu Arg Gly Lys Leu Ile Ala Gly
        115                 120                 125

Gly Phe Phe Lys Ala Asn Pro Leu Tyr Tyr Val Trp Lys Val Val Ser
    130                 135                 140

Thr Val Ala Leu Ala Val Gly Ala Trp Met Leu Val Ala Trp Ser Gln
145                 150                 155                 160

Asn Leu Gly Val Gln Met Leu Ser Ala Phe Leu Val Ala Leu Phe Trp
                165                 170                 175

Gln Gln Cys Gly Trp Leu Ala His Asp Phe Leu His His Gln Val Phe
            180                 185                 190

Lys Asn Arg Ala Leu Gly Asp Leu Ala Gly Ile Val Ile Gly Asn Val
        195                 200                 205

Phe Gln Gly Phe Ser Val Ala Trp Trp Lys Asn Lys His Asn Thr His
    210                 215                 220

His Ala Val Pro Asn Leu Val Glu Ser Ser Pro Asp Ala Gln Asp Gly
225                 230                 235                 240

Asp Pro Asp Ile Asp Thr Met Pro Ile Leu Ala Trp Ser Leu Lys Met
                245                 250                 255

Ala Asp Arg Ala Gln Gln Tyr Ser Trp Gly Pro Phe Phe Val Arg His
            260                 265                 270

Gln Ser Leu Leu Tyr Phe Pro Ile Leu Leu Val Ala Arg Ile Ser Trp
        275                 280                 285

Leu Met Gln Ser Phe Leu Phe Val Phe Asp Ser Val Pro Gly Ala Ser
    290                 295                 300

Leu Trp Ala Thr Lys Gly Ala Thr Ala Glu Arg Gln Ala Ile Lys Asn
305                 310                 315                 320

Val Gly Leu Glu Lys Val Gly Leu Val Ala His Tyr Leu Trp Tyr Gly
                325                 330                 335

Ala Leu Met Leu Cys His Met Ser Leu Ala Arg Ala Leu Leu Tyr Phe
            340                 345                 350

Leu Ala Ser Gln Met Met Cys Gly Phe Leu Leu Ala Leu Val Phe Gly
        355                 360                 365

Leu Gly His Asn Gly Met Ala Val Tyr Asp Ala Asp Ala Arg Pro Asp
    370                 375                 380
```

```
Phe Trp Lys Leu Gln Val Thr Thr Thr Arg Asn Val Thr Gly Ser Trp
385                 390                 395                 400

Leu Val Gln Trp Phe Cys Gly Gly Leu Gly Tyr Gln Val Asp His His
                405                 410                 415

Leu Phe Pro Met Ile Pro Arg His Arg Leu Gly Lys Leu His Gly Leu
            420                 425                 430

Val Glu Gly Phe Cys Lys Asp His Gly Val Lys Tyr His Glu Thr Asn
        435                 440                 445

Met Trp Glu Gly Thr Lys Glu Val Leu Ala His Leu Ser Ser Val Thr
    450                 455                 460

Lys Glu Phe Val Ala Asp Phe Pro Ala Met
465                 470
```

<210> SEQ ID NO 37
<211> LENGTH: 1425
<212> TYPE: DNA
<213> ORGANISM: Nannochloropsis oculata

<400> SEQUENCE: 37

```
atgggacgcg gtggcgagcg ggtcgagacg acggagtctt tgagcttcac ggccgacaag     60

gcggggacca tcaagcagcg tggggggaag atcacatggg atgaggtgcg tcagcacaag    120

acgcctcagg acgcttggct cgtgtatagg aataaggtct acgacgtgtc gggctggcaa    180

gatcaccccg gggggaacgt catcttcact cacgccggcg gggactgcac ggatattttc    240

gcggcgttcc accctcttgg cgccacctct tatcttgatc cattttacat tggcgagctg    300

gagccgggct cggacaagaa gcccgcagcg caggcgaact ttgagcgggc ctacagggat    360

ctcaggggga agcttatcgc gggtgggttt ttcaaggcga atcctttgta ctatgtctgg    420

aaggtagtat cgacagttgc ccttgctgta ggtgcgtgga tgctggtggc ttggtcgcag    480

aacctgggcg tgcagatgct gtctgcgttt ttggtggctc tgttctggca gcaatgtggc    540

tggttggccc atgacttcct gcaccaccag gtatttaaga accgtgcgtt gggtgacctg    600

gccggcatcg ttatcggcaa tgtcttccag ggtttctccg tggcatggtg gaagaacaag    660

cataacactc accacgcggt gcccaacctc gtcgagtcct ctccggacgc gcaagacgga    720

gaccctgaca ttgacaccat gcccatactg gcctggtcgc tcaagatggc cgacagggcg    780

cagcaatact catggggacc cttctttgtc aggcatcagt cgctgctata cttccccatc    840

ctgctcgtgg cgcggatttc atggttgatg cagtcgttct tgtttgtctt tgactccgtc    900

cctggagcga gtctgtgggc aaccaagggc gcgacggctg agagacaggc gatcaagaat    960

gtcgggttgg agaaggtggg gctggttgcg cactacctgt ggtacggtgc gctgatgctg   1020

tgccacatgt ccctggcccg cgccctgctg tacttcctgg cgagccagat gatgtgcggg   1080

ttcttgctcg cgcttgtttt cgggcttggg cacaacggca tggctgttta cgacgcggac   1140

gcccggcccg acttctggaa gctgcaggtg acgacgacga ggaacgtgac gggctcgtgg   1200

ttggtgcagt ggttctgtgg cggcctcggc taccaggtgg accaccacct gttccccatg   1260

atcccgcggc accgcctagg gaagctccac gggctcgtgg agggtttctg caaggatcac   1320

ggggtgaagt accacgagac gaatatgtgg gaggggacca aagaggtgtt ggctcacttg   1380

agcagtgtga cgaaagagtt cgtggccgat ttccccgcca tgtaa                   1425
```

<210> SEQ ID NO 38
<211> LENGTH: 475
<212> TYPE: PRT
<213> ORGANISM: Nannochloropsis gaditana

<400> SEQUENCE: 38

```
Met Gly Arg Gly Gly Glu Arg Val Glu Thr Gln Glu Ser Ile Ala Thr
1               5                   10                  15

Tyr Ser Ala Ser Lys Ser Gly Asp Ile Arg Gln His Gly Gly Lys Ile
            20                  25                  30

Thr Trp Asp Glu Val Arg Gln His Lys Thr Pro Gln Asp Ala Trp Leu
        35                  40                  45

Val Tyr Arg Asn Lys Val Tyr Asp Val Ser Gly Trp Gln Asp His Pro
    50                  55                  60

Gly Gly Asn Val Ile Phe Thr His Ala Gly Gly Asp Cys Thr Asp Ile
65                  70                  75                  80

Phe Ala Ala Phe His Pro Leu Gly Ala Thr Ser Tyr Met Asp Pro Phe
                85                  90                  95

Tyr Ile Gly Glu Leu Val Pro Gly Ser Asp Lys Lys Pro Glu Ala Gln
            100                 105                 110

Ala Ser Phe Glu Arg Ala Tyr Arg Asp Leu Arg Gly Lys Leu Ile Thr
        115                 120                 125

Gly Gly Phe Phe Lys Ala Ser Pro Leu Tyr Tyr Val Trp Lys Val Val
    130                 135                 140

Ser Thr Val Ala Leu Ala Val Gly Ala Trp Met Leu Val Gly Trp Ser
145                 150                 155                 160

Gln Ala Leu Ser Ile Gln Met Leu Ser Ala Phe Ile Leu Ala Leu Phe
                165                 170                 175

Trp Gln Gln Cys Gly Trp Leu Ala His Asp Phe Leu His His Gln Val
            180                 185                 190

Phe Lys Glu Arg Ala Tyr Gly Asp Leu Ala Gly Ile Met Ile Gly Asn
        195                 200                 205

Val Phe Gln Gly Phe Ser Val Ala Trp Trp Lys Asn Lys His Asn Thr
    210                 215                 220

His His Ala Val Pro Asn Leu Val Glu Ser Ser Pro Asp Ala Gln Asp
225                 230                 235                 240

Gly Asp Pro Asp Ile Asp Thr Met Pro Ile Leu Ala Trp Ser Leu Lys
                245                 250                 255

Met Ala Asp Arg Ala Lys Glu Tyr Ser Trp Gly Pro Phe Phe Leu Arg
            260                 265                 270

His Gln Ala Phe Leu Tyr Phe Pro Ile Leu Leu Val Ala Arg Ile Ser
        275                 280                 285

Trp Leu Leu Gln Ser Phe Leu Phe Val Phe Glu His Val Pro Gly Ala
    290                 295                 300

Ser Leu Trp Ala Thr Lys Gly Ala Thr Thr Glu Arg Gln Ala Ile Lys
305                 310                 315                 320

Asn Val Gly Leu Glu Lys Ala Gly Leu Leu Leu Tyr Tyr Leu Trp Tyr
                325                 330                 335

Gly Ala Leu Met Phe Cys Asn Met Ser Leu Thr Arg Val Leu Ile Tyr
            340                 345                 350

Phe Val Ala Ser Gln Met Met Cys Gly Phe Leu Leu Ala Leu Val Phe
        355                 360                 365

Gly Leu Gly His Asn Gly Met Ala Val Tyr Asp Ala Asp Ala Arg Pro
    370                 375                 380

Asp Phe Trp Lys Leu Gln Val Thr Thr Thr Arg Asn Val Thr Gly Gly
385                 390                 395                 400

Trp Leu Ile Gln Trp Phe Cys Gly Gly Leu Gly Tyr Gln Val Asp His
```

```
            405                 410                 415

His Leu Phe Pro Met Ile Pro Arg His Arg Leu Gly Gln Leu His Gly
        420                 425                 430

Leu Val Glu Ser Phe Cys Lys Glu His Gly Val Lys Tyr His Glu Thr
    435                 440                 445

Ser Met Trp Glu Gly Thr Arg Glu Val Leu Ala His Leu Ala Ser Val
    450                 455                 460

Thr Lys Glu Phe Val Thr Asp Phe Pro Ala Met
465                 470                 475


<210> SEQ ID NO 39
<211> LENGTH: 1428
<212> TYPE: DNA
<213> ORGANISM: Nannochloropsis gaditana

<400> SEQUENCE: 39

atgggacgcg gtggtgaaag agtggagacg caagagtcta tagctactta ctcggcaagc     60

aaaagtggtg acatcaggca gcatgggggt aaaattactt gggatgaggt gcgtcaacac    120

aagacccctc aagatgcgtg gctcgtctac cgcaacaaag tctacgacgt gtcaggctgg    180

caagatcatc ctgggggaa tgtcatcttt acgcatgcgg ggggtgactg tactgacatc    240

tttgcagcct tccacccttt gggtgcgaca tcttacatgg atcccttcta cattggcgag    300

ctcgttcccg gctctgacaa aaagcccgag gcgcaagcca gcttcgagcg agcgtatcga    360

gacttgaggg ggaaactcat cacgggcggg ttcttcaagg cgagtccttt gtactatgtg    420

tggaaagtcg tgtccaccgt cgccctggcc gtgggtgcct ggatgctcgt cggctggtcc    480

caagccctgt cgattcagat gctctctgcc ttcatcctcg ccctcttctg gcagcagtgc    540

gggtggctgg cccatgactt cttgcaccat caagttttca aagagcgagc atacggcgat    600

ctcgcgggga tcatgatcgg caatgtattc cagggcttct cggtggcctg gtggaagaac    660

aagcacaaca ctcatcacgc cgtgcccaac cttgtcgagt cctctccaga cgcccaggac    720

ggtgatcccg acattgacac catgcccatc ctggcctggt ccctgaagat ggcggaccgc    780

gcaaaggaat actcgtgggg ccctttcttc ctccggcatc aggctttcct ctactttccc    840

atcctccttg tcgcccgcat ctcctggctc ttgcaatcct tcctttttgt cttcgaacac    900

gtccccggtg caagcttatg ggctacgaaa ggcgcaacga ccgagcgaca ggccataaag    960

aacgtgggac tagagaaagc ggggcttctc ctttactatt tgtggtacgg cgctctcatg   1020

ttctgcaaca tgtctcttac gcgggtcctg atctacttcg tggcttctca gatgatgtgc   1080

ggctttctct tggccctcgt cttcggcctc ggccacaacg gcatggcggt ctacgacgcc   1140

gacgcccgcc cggacttctg gaaactgcaa gtgacgacca cgagaaatgt gacgggggc   1200

tggttgatac aatggttctg tggcggtctt ggctaccaag tagaccacca cctttttcca   1260

atgattccgc gccaccgtct tggtcagtta cacggtttgg tggaatcttt ctgcaaggag   1320

catggggtaa agtatcacga gacaagtatg tgggaaggga cacgggaggt gttggcccac   1380

ttggcgagcg tgacaaaaga attcgtaaca gatttcccag caatgtag                1428


<210> SEQ ID NO 40
<211> LENGTH: 410
<212> TYPE: PRT
<213> ORGANISM: Nannochloropsis oculata

<400> SEQUENCE: 40

Met Val Glu Gln Thr Leu Pro Thr Leu Ser Gln Ile Lys Lys Ala Ile
```

```
1               5                   10                  15

Pro Glu Lys Cys Phe Gln Lys Ser Leu Leu Arg Ser Phe Tyr Tyr Met
            20                  25                  30

Leu Arg Asp Phe Ala Ala Leu Ala Ala Leu Tyr Phe Val Tyr Pro Thr
        35                  40                  45

Val Gln Ala Lys Tyr Gly Leu Pro Gly Leu Phe Val Trp Trp Asn Leu
    50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Leu Asn Asp Ile Cys Gly His
                85                  90                  95

Ile Cys His Ala Pro Leu Met Val Pro Tyr Trp Pro Trp Gln Lys Ser
            100                 105                 110

His Arg Leu His His Met Tyr His Asn His Leu Thr Lys Asp Met Ser
        115                 120                 125

His Pro Trp Met Thr Lys Glu Val Phe Glu Asp Leu Thr Pro Phe Glu
    130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Met Asp Gly Ser His Val Val Pro Phe
                165                 170                 175

Ser Pro Leu Phe Thr Asp Thr Lys Glu Arg Val Gln Cys Ala Val Ser
            180                 185                 190

Thr Leu Gly Met Val Val Ala Gly Ala Leu Val Tyr Ile Gly Leu Glu
        195                 200                 205

Gly Gly Lys Glu Gly Gly Met Ala Arg Ile Gly Ser Ile Tyr Val Val
    210                 215                 220

Pro Leu Leu Val Phe Asn Ala Trp Ile Thr Met Val Thr Tyr Leu Gln
225                 230                 235                 240

His His Asp Glu Asp Thr Lys Val Tyr Ala Glu Gly Glu Trp Asn Tyr
                245                 250                 255

Ile Lys Gly Ala Leu Glu Thr Ile Asp Arg Glu Tyr Gly Met Gly Ile
            260                 265                 270

Asp Asp Leu Ser His Asn Ile Thr Asp Gly His Val Ala His His Leu
        275                 280                 285

Phe Phe Thr Gln Ile Pro His Tyr His Leu Thr Ala Ala Thr Ala Ala
    290                 295                 300

Val Arg Gln Cys Leu Gln Pro Thr Gly Thr Tyr Lys Lys Arg Arg Ser
305                 310                 315                 320

Trp Asn Phe Leu Ala Arg Phe Thr Glu Leu Asn Tyr Arg Leu Lys Tyr
                325                 330                 335

Val Ala Gly Gln Gly Val Leu Ser Tyr Val Asp Trp Glu Val Ala Arg
            340                 345                 350

Lys Thr Pro Ala Ser Ala Val Thr Ser Ser Phe Ser Ser Ser Ser Ser
        355                 360                 365

Ser Ser Leu Pro Ala Glu Ala Ala Val Lys Ala Ala Ala Ala Val Pro
    370                 375                 380

Val Ala Ala Val Ala Ala Pro Val Arg Glu Gly Arg Pro Thr Arg Lys
385                 390                 395                 400

Arg Ser Pro Thr Arg Ser Ser Ser Pro Pro
                405                 410
```

<210> SEQ ID NO 41

```
<211> LENGTH: 1233
<212> TYPE: DNA
<213> ORGANISM: Nannochloropsis oculata

<400> SEQUENCE: 41

atggttgagc aaacgttacc gaccttgtcc cagatcaaga aagccatccc cgagaaatgc      60

ttccagaaat ccctcctccg ctccttttac tacatgctga gggacttcgc ggccttggcg     120

gcactctact ttgtttatcc cacagttcag gccaagtatg gattgcctgg tttgtttgtg     180

tggtggaacc tcgcaggctt tttcatgtgg tgcctcttcg tgataggcca cgattgcggc     240

catggctcct tctccgagta caagtggctc aatgacattt gcggtcacat ttgccacgcc     300

cccttgatgg tgccttactg gccttggcag aagtcccacc gccttcacca catgtaccac     360

aaccacctga ctaaggacat gtcacacccg tggatgacca aggaggtgtt cgaggacttg     420

accccattcg agcaggcgtt gctggagaac ccgctgtccc tcttcatcaa gtacaccttc     480

ctttacctct ttgcgggcaa gatggatggc agccatgtag ttccattctc ccccctcttc     540

accgacacca aggagcgggt gcaatgcgca gtgtcgacgc tgggtatggt cgtcgcaggc     600

gcccttgtgt acatcgggct cgagggcggg aaggagggag ggatggcgag gataggatcc     660

atttatgtgg tgccgttgct ggtgttcaat gcctggatca cgatggtgac atacctgcag     720

caccacgatg aggacaccaa ggtttatgca gagggggagt ggaactacat caagggggcc     780

ctggagacga tcgaccgcga atacggcatg gggattgacg acctctccca caatatcacg     840

gatggccacg tggcgcacca cctcttcttc acgcagatcc cgcactacca cctgacggcg     900

gccacggccg ctgtgagaca atgcctgcaa cctacgggga cctacaagaa gaggaggagc     960

tggaatttc tcgctcgttt cacggagctt aactaccgtt tgaaatacgt cgcgggccag     1020

ggcgtgctct cctatgtgga ttgggaggtc gctcgcaaga cccctgcttc cgccgtcacc    1080

tcctctttct cttcctcctc ctcttcctcc cttccggcag aggctgctgt caaggcggct    1140

gctgccgttc ccgttgctgc tgttgctgct cccgtccgag aaggaagacc aacacgcaag    1200

cgctctccca cccgttcatc ctcccctccg taa                                 1233


<210> SEQ ID NO 42
<211> LENGTH: 407
<212> TYPE: PRT
<213> ORGANISM: Nannochloropsis gaditana

<400> SEQUENCE: 42

Met Val Glu Gln Thr Leu Pro Thr Leu Ser Gln Leu Lys Lys Ala Ile
1               5                   10                  15

Pro Glu Lys Cys Phe Gln Lys Ser Leu Leu Arg Ser Val Tyr Tyr Met
            20                  25                  30

Leu Arg Asp Phe Ala Ala Leu Ala Ala Leu Tyr Ile Ile Tyr Pro Ser
        35                  40                  45

Val Gln Ala Asn Phe Gly Leu Ala Gly Leu Phe Val Trp Trp Asn Leu
    50                  55                  60

Ala Gly Phe Phe Met Trp Cys Leu Phe Val Ile Gly His Asp Cys Gly
65                  70                  75                  80

His Gly Ser Phe Ser Glu Tyr Lys Trp Phe Asn Asp Val Cys Gly His
                85                  90                  95

Ile Cys His Ala Pro Leu Met Val Pro Tyr Trp Pro Trp Gln Lys Ser
            100                 105                 110

His Arg Leu His His Met Tyr His Asn His Leu Thr Lys Asp Met Ser
        115                 120                 125
```

```
His Pro Trp Met Thr Gln Glu Ile Phe Glu Asp Leu Thr Pro Phe Glu
    130                 135                 140

Gln Ala Leu Leu Glu Asn Pro Leu Ser Leu Phe Ile Lys Tyr Thr Phe
145                 150                 155                 160

Leu Tyr Leu Phe Ala Gly Lys Leu Asp Gly Ser His Val Leu Pro Thr
                165                 170                 175

Ser Pro Leu Phe Ser Asp Thr Lys Glu Arg Ile Gln Cys Ala Val Ser
            180                 185                 190

Thr Leu Cys Met Leu Val Ala Gly Val Leu Ile Tyr Val Gly Leu Glu
        195                 200                 205

Gly Gly Ala Glu Gly Gly Leu Ala Arg Ile Gly Ser Met Tyr Leu Ile
    210                 215                 220

Pro Leu Leu Val Phe Asn Ala Trp Ile Thr Met Val Thr Tyr Leu Gln
225                 230                 235                 240

His His Asp Glu Asp Thr Lys Val Tyr Ala Glu Gly Glu Trp Ser Tyr
                245                 250                 255

Ile Lys Gly Ala Leu Glu Thr Ile Asp Arg Glu Tyr Gly Met Gly Ile
            260                 265                 270

Asp Asp Leu Ser His Asn Ile Thr Asp Gly His Val Ala His His Leu
        275                 280                 285

Phe Phe Thr Gln Ile Pro His Tyr His Leu Lys Asp Ala Thr Ala Ala
    290                 295                 300

Val Arg Gln Leu Leu Thr Pro Thr Gly Thr Tyr Lys Lys Lys Gln Ser
305                 310                 315                 320

Trp Asn Phe Leu Gly Lys Phe Thr Glu Leu Asn Tyr Lys Leu Lys Tyr
                325                 330                 335

Val Ala Gly Gln Gly Val Leu Ser Tyr Val Asp Trp Glu Ala Ile Gln
            340                 345                 350

Lys Gly Ala Ser Pro Pro Val Cys Ser Thr Asp Ala Ser Pro Ala Thr
        355                 360                 365

Pro Ala Ala Pro Leu Pro Lys Val Ala Val Thr Cys Ala Thr Glu Pro
    370                 375                 380

Leu Ile Ala Leu Glu Ala Lys Gly Arg Ser Thr Arg Lys Arg Ser Pro
385                 390                 395                 400

Ala Arg Ser Ser Ser Pro Pro
                405
```

```
<210> SEQ ID NO 43
<211> LENGTH: 1224
<212> TYPE: DNA
<213> ORGANISM: Nannochloropsis gaditana

<400> SEQUENCE: 43

atggttgagc aaacgctacc gacactttct caattgaaga aagccattcc cgagaaatgc      60

ttccagaaat cacttctccg ctctgtgtac tacatgctgc gagactttgc cgccctggca     120

gctctgtata ttatataccc cagcgtgcag gctaattttg gccttgccgg actctttgtg     180

tggtggaacc tggcgggatt ttttatgtgg tgtctctttg tgatcggtca cgactgtggt     240

cacggctcct tctcggagta taagtggttc aacgacgtct gtggccatat ttgccacgcc     300

ccgctcatgg tgccctactg gccctggcag aagtcccatc gcctgcacca catgtaccac     360

aaccacctga cgaaagacat gtcacatcca tggatgacgc aagagatctt cgaggaccta     420

acaccgttcg agcaagcctt gctggagaac ccactctccc tcttcatcaa atacacattc     480
```

```
ctctacctct tcgcgggcaa actcgacggc agccacgtcc tgcccacctc cccctcttc     540

agcgatacca aggagcgcat ccagtgcgcc gtctccaccc tctgcatgct cgtggccggg    600

gtcctcattt atgtgggcct tgaaggaggg gcggagggag ggctggctcg gatcggctcc    660

atgtatttga tcccgctgtt ggtgttcaac gcctggatca ccatggtcac gtacctgcag    720

catcacgacg aggacacgaa ggtgtacgcg gagggggagt ggagctacat caagggggcg    780

ctcgagacca tcgatcggga gtatgggatg ggcattgatg acctgtcgca caacatcacg    840

gacggccacg tcgcccacca cctcttcttc acccagatcc cgcactacca cctgaaggac    900

gctacggccg ccgtacggca gctcttgacg cccacgggca cctacaagaa gaagcaatcc    960

tggaattttc tgggaaaatt cactgagttg aactacaagt tgaagtatgt tgcgggacaa   1020

ggggtgctct cctacgtgga ctgggaggct attcagaagg gtgcttcccc cccggtttgt   1080

tccaccgacg cctcccctgc cactcccgca gcgcccctac ctaaggtggc tgtcacctgc   1140

gcgacagaac cgttaatcgc ccttgaagcg aagggaagat caacccgaaa gcgctctccg   1200

gcacgctcct cttcacctcc gtag                                           1224
```

<210> SEQ ID NO 44
<211> LENGTH: 526
<212> TYPE: PRT
<213> ORGANISM: Nannochloropsis oculata

<400> SEQUENCE: 44

```
Met Pro Pro Gln Asn Asp Ala Ala Leu Gly Gly Gly Phe Phe Arg Asn
1               5                   10                  15

Arg Phe Thr Arg Lys Asn Ser Thr Ser Ser Leu Ile Ile Asp Asp Thr
            20                  25                  30

Pro Ala Thr Ser Thr Glu Ser Val Ala Ala Ala Glu Ala Thr Val Ala
        35                  40                  45

Ala Thr Ala Ala Ala Ala Ala Gly Gly Lys Thr Tyr Thr Trp Glu Glu
    50                  55                  60

Val Ala Glu His Asn Thr Glu Lys Ser Leu Trp Val Thr Val Arg Gly
65                  70                  75                  80

Lys Val Tyr Asp Ile Ser Ser Trp Val Asn Asn His Pro Gly Gly Lys
                85                  90                  95

Glu Ile Leu Leu Leu Ala Ala Gly Arg Asp Ile Thr Tyr Ala Phe Asp
            100                 105                 110

Ser Tyr His Pro Phe Thr Glu Lys Pro Thr Gln Val Leu Gly Lys Phe
        115                 120                 125

Glu Ile Gly Thr Val Ser Ser His Glu Phe Pro Gln Tyr Lys Pro Asp
    130                 135                 140

Thr Arg Gly Phe Tyr Lys Thr Leu Cys Thr Arg Val Gly Asp Tyr Phe
145                 150                 155                 160

Lys Gln Glu Lys Leu Asn Pro Lys Asp Pro Phe Pro Gly Ile Trp Arg
                165                 170                 175

Met Leu Leu Val Ala Met Val Ala Val Ala Ser Phe Met Val Cys Asn
            180                 185                 190

Gly Trp Val Gly Leu Glu Gly Gly Val Leu Ala Gly Trp Gly Ala Arg
        195                 200                 205

Phe Val Ala Ala Val Val Phe Gly Val Cys Gln Ala Leu Pro Leu Leu
    210                 215                 220

His Val Met His Asp Ser Ser His Leu Ala Phe Gly Asn Thr Glu Arg
225                 230                 235                 240
```

```
Trp Trp Gln Met Gly Gly Arg Leu Ala Met Asp Phe Phe Ala Gly Ala
                245                 250                 255

Asn Met Thr Ser Trp His Asn Gln His Val Ile Gly His His Ile Tyr
            260                 265                 270

Thr Asn Val Phe Met Ala Asp Pro Asp Leu Pro Asp Lys Ser Ala Gly
        275                 280                 285

Asp Pro Arg Arg Leu Val Lys Lys Gln Ala Trp Glu Gly Met Tyr Lys
    290                 295                 300

Trp Gln His Leu Tyr Leu Pro Pro Leu Tyr Gly Ile Leu Gly Ile Lys
305                 310                 315                 320

Phe Arg Val Gln Asp Val Met Glu Thr Tyr Gly Ser Gly Ser Asn Gly
                325                 330                 335

Pro Val Arg Val Asn Pro Leu Ser Pro Trp Gln Trp Gly Glu Met Ile
            340                 345                 350

Phe Thr Lys Leu Phe Trp Phe Gly Trp Arg Val Val Phe Pro Leu Met
        355                 360                 365

Ser Ala Ser Phe Arg Thr Ser Met Ala Thr Phe Trp Pro Leu Phe Phe
    370                 375                 380

Val Ser Glu Phe Met Thr Gly Tyr Phe Leu Ala Phe Asn Phe Gln Val
385                 390                 395                 400

Ser His Val Ser Ser Glu Cys Asp Tyr Pro Leu Gly Glu Ala Pro Arg
                405                 410                 415

Glu Glu Ala Val Glu Gly Ser Ala Gly Gly Lys Glu Gly Ile Lys Asp
            420                 425                 430

Glu Trp Ala Val Ser Gln Val Lys Ser Ser Val Asp Tyr Ala His Asn
        435                 440                 445

Asn Ala Leu Thr Thr Phe Leu Cys Gly Ala Leu Asn Tyr Gln Val Thr
    450                 455                 460

His His Leu Phe Pro Thr Val Ser Gln Tyr His Tyr Pro Lys Ile Ala
465                 470                 475                 480

Pro Ile Ile Gln Glu Val Cys Lys Glu Phe Asn Val Asp Tyr Lys Val
                485                 490                 495

Leu Pro Asp Phe Val Thr Ala Phe His Ala His Ile Ala His Leu Lys
            500                 505                 510

Ala Leu Gly Glu Arg Gly Glu Ala Ala Glu Val His Met Gly
        515                 520                 525
```

```
<210> SEQ ID NO 45
<211> LENGTH: 1581
<212> TYPE: DNA
<213> ORGANISM: Nannochloropsis oculata

<400> SEQUENCE: 45

atgcctcccc agaacgacgc tgctcttgga ggcggttttt ttcgcaaccg cttcacccga      60

aagaactcca cttcctccct catcatcgat gacacgccgg ccaccagcac tgagtccgtg     120

gcggcagcag aagcaacagt agcagcgaca gcagccgccg ccgccggcgg taagacctac     180

acatgggagg aagtggcgga gcacaacact gagaagagcc tgtgggtgac cgtgcgagga     240

aaggtgtatg acatcagcag ctgggtgaac aaccacccgg gagggaagga gattctgttg     300

ttggcggcgg gcagggatat cacctatgcc ttcgactctt accacccttt cacggagaag     360

ccgacgcagg tcctgggcaa gtttgagatc ggcactgtgt cctcccacga attcccgcag     420

tacaaacccg acacccgggg cttctacaag acgctgtgca cgcgcgtagg tgactacttt     480

aagcaggaga agttgaaccc taaggaccct ttcccaggga tatggcggat gctcctggtg     540
```

```
gcgatggtgg ccgtagcctc ctttatggtg tgcaacgggt gggtggggct ggaaggaggg    600
gtactggcag gatggggagc gaggtttgtg gcggcggtgg tgtttggtgt gtgccaggcg    660
ttgccccttc tgcacgtcat gcacgactca tcccacctgg cgttcgggaa cacggagagg    720
tggtggcaaa tggggggag gctggccatg gatttcttcg cgggggcgaa catgacgagt    780
tggcacaatc agcacgtgat agggcatcac atttatacga atgtgttcat ggctgacccg    840
gacttgcccg ataagagcgc tggggacccg aggcggctgg ttaagaagca ggcatgggag    900
gggatgtaca agtggcagca cctctacttg ccacctttgt acggcatcct gggcatcaag    960
ttccgggtgc aagacgtgat ggagacgtac gggagcgggt cgaatgggcc ggtgagggtt   1020
aacccettga gcccctggca gtggggggag atgatcttca ccaagctctt ctggttcggc   1080
tggcgcgtgg tgttcccgct catgtcggca agctttcgga cgagcatggc cacgttctgg   1140
cccttgttct tcgtgagtga gttcatgacg ggatacttcc tggcgttcaa tttccaggtg   1200
tcacacgtct cgtccgagtg cgattatccg ctgggcgagg cgccgaggga ggaagcggta   1260
gagggctcgg caggagggaa ggaaggtatc aaggacgaat gggccgtgag ccaggtgaag   1320
agtagcgtgg actacgccca caataacgct ttgacgacct tcctgtgcgg ggctttgaac   1380
taccaggtga cgcaccacct gttccccact gtaagtcagt accactaccc caagatcgcg   1440
cccatcatcc aggaggtatg caaggagttt aacgtcgact acaaggtcct gcccgatttt   1500
gtgacggcgt tccatgcgca cattgcgcat ttgaaggcct tgggagagag gggcgaggcg   1560
gcggaggtgc acatgggtta g                                             1581
```

<210> SEQ ID NO 46
<211> LENGTH: 515
<212> TYPE: PRT
<213> ORGANISM: Nannochloropsis gaditana

<400> SEQUENCE: 46

```
Met Pro Pro Gln Asn Asp Ala Ala Leu Gly Ser Gly Leu Phe Arg Asn
1               5                   10                  15

Arg Phe Gly Arg Lys Ser Ser Ala Ser Ser Leu Leu Val Asn Asp Gly
            20                  25                  30

Ser Met Gly Ser Thr Glu Pro Val Leu Ser Thr Ala Ala Val Pro Ala
        35                  40                  45

Thr Glu Pro Ala Gly Lys Ser Tyr Thr Trp Gln Glu Val Ala Glu His
    50                  55                  60

Asn Thr Glu Lys Ser Leu Trp Val Thr Val Arg Gly Lys Val Tyr Asp
65                  70                  75                  80

Ile Ser Ser Trp Val Asp Asn His Pro Gly Gly Lys Glu Ile Leu Leu
                85                  90                  95

Leu Ala Ala Gly Arg Asp Ile Thr Tyr Ala Phe Asp Ser Tyr His Pro
            100                 105                 110

Phe Thr Glu Lys Pro Thr Gln Val Leu Asn Lys Phe Glu Ile Gly Arg
        115                 120                 125

Val Thr Ser Tyr Glu Phe Pro Gln Tyr Lys Ala Asp Thr Arg Gly Phe
    130                 135                 140

Tyr Lys Ala Leu Cys Thr Arg Val Asn Asp Tyr Phe Val Ala His Lys
145                 150                 155                 160

Leu Asn Pro Lys Asp Pro Ile Pro Gly Ile Trp Arg Met Cys Leu Val
                165                 170                 175

Ala Leu Val Ala Leu Ala Ser Phe Val Val Cys Asn Gly Tyr Val Gly
```

```
            180                 185                 190

Val Glu Gly Thr Trp Ala Gly Thr Thr Trp Ala Arg Leu Val Ala Ala
        195                 200                 205

Val Val Phe Gly Ile Cys Gln Ala Leu Pro Leu Leu His Val Met His
    210                 215                 220

Asp Ser Ser His Leu Ala Phe Gly Asn Thr Glu Arg Trp Trp Gln Val
225                 230                 235                 240

Gly Gly Arg Leu Ala Met Asp Phe Phe Ala Gly Ala Asn Met Thr Ser
                245                 250                 255

Trp His Asn Gln His Val Ile Gly His His Ile Tyr Thr Asn Val Phe
            260                 265                 270

Leu Ala Asp Pro Asp Leu Pro Asp Lys Ala Ala Gly Asp Pro Arg Arg
        275                 280                 285

Leu Val Gln Lys Gln Ala Trp Gln Ala Met Tyr Lys Trp Gln His Leu
    290                 295                 300

Tyr Leu Pro Pro Leu Tyr Gly Ile Leu Gly Ile Lys Phe Arg Val Gln
305                 310                 315                 320

Asp Ile Met Glu Thr Phe Gly Ser Gly Thr Asn Gly Pro Val Arg Val
                325                 330                 335

Asn Pro Leu Ser Phe Phe Gln Trp Ala Glu Met Ile Phe Thr Lys Met
            340                 345                 350

Phe Trp Ala Gly Trp Arg Ile Ala Phe Pro Leu Leu Ser Pro Ser Phe
        355                 360                 365

His Thr Gly Trp Ala Ala Phe Ser Ala Leu Phe Leu Val Ser Glu Phe
    370                 375                 380

Met Thr Gly Tyr Phe Leu Ala Phe Asn Phe Gln Val Ser His Val Ser
385                 390                 395                 400

Ser Glu Cys Asp Tyr Pro Leu Gly Glu Ala Pro Arg Glu Gly Glu Asp
                405                 410                 415

Gly Asn Ile Val Asp Glu Trp Ala Val Ser Gln Ile Lys Ser Ser Val
            420                 425                 430

Asp Tyr Ala His Asn Asn Pro Val Thr Thr Phe Leu Cys Gly Ala Leu
        435                 440                 445

Asn Tyr Gln Val Thr His His Leu Phe Pro Thr Val Ser Gln Tyr His
    450                 455                 460

Tyr Pro Ala Ile Ala Pro Ile Ile Gln Asp Val Cys Arg Glu Phe Asn
465                 470                 475                 480

Val Asp Tyr Lys Val Leu Pro Asp Phe Val Thr Ala Phe His Ala His
                485                 490                 495

Ile Ala His Leu Lys Thr Leu Gly Glu Arg Gly Glu Ala Ala Glu Val
            500                 505                 510

His Met Gly
        515
```

<210> SEQ ID NO 47
<211> LENGTH: 1548
<212> TYPE: DNA
<213> ORGANISM: Nannochloropsis gaditana

<400> SEQUENCE: 47

```
atgcctccgc agaacgacgc tgccctcgga agtggtctct ttcggaaccg cttcggtcgc      60

aaaagctccg cttcttccct tcttgtcaat gacggcagta tgggaagcac cgagcctgtc     120

ctttccacgg cggccgtacc ggcaacggag ccggcgggga aatcctacac atggcaagaa     180
```

```
gtagccgagc acaacacaga gaaaagtttg tgggtcactg tgcgagggaa ggtgtacgac    240
atatccagtt gggtggacaa ccatccgggg ggcaaggaga tcctgctgtt ggcggcgggg    300
agggacatca cgtacgcctt cgattcctac cacccgttca cggagaaacc gacgcaggtg    360
ctcaacaagt ttgagatcgg ccgggtcacc tcctacgaat tcccccagta caaggcggac    420
actcgtggtt tctacaaggc cctgtgcacc cgcgtgaatg actactttgt ggcccacaag    480
ctcaacccta aggacccaat ccccggcatc tggcgcatgt gcctcgtcgc cctggtggcc    540
ttggcctctt tcgtggtctg caacggctac gtgggtgtgg aagggacatg ggccgggact    600
acgtgggccc ggctagtggc ggcggtggtg tttgggatct gtcaggccct tcctttgttg    660
cacgtcatgc acgactcctc ccacctggcg tttggcaata cagaacgctg gtggcaggtg    720
ggggggcggc tggcgatgga tttcttcgcc ggggcgaaca tgaccagctg gcacaaccaa    780
cacgtgatcg gccaccatat ctacacgaat gtcttcctcg ccgacccgga tttacccgac    840
aaagccgcgg gagatccgag aagattggtg cagaaacagg cgtggcaagc catgtataaa    900
tggcagcact tgtaccttcc ccctctgtac ggcatcctgg ggatcaaatt tcgagtccaa    960
gatatcatgg agaccttcgg aagtggcacg aacgggcccg tacgggtgaa ccccttgtcc   1020
tttttccaat gggccgagat gattttcacc aaaatgtttt gggcaggatg gaggatcgcg   1080
ttccccttgc tctccccgtc tttccacacc ggctgggctg ctttttccgc cctcttcctg   1140
gtcagcgagt ttatgaccgg gtacttcctc gcctttaatt tccaagtctc ccacgtctcc   1200
tccgaatgcg actacccctt gggcgaagcc ccccgagagg gagaggatgg caacatcgtg   1260
gacgaatggg cggtctccca aataaagagc agtgtggact atgcgcacaa caacccagta   1320
accaccttcc tctgcggcgc cctgaactac caagtcactc accatctgtt ccccactgtg   1380
agtcaatacc actacccagc catcgcgccc atcatccaag acgtgtgtcg ggagttcaat   1440
gtggattaca aggttctgcc ggattttgtg acggctttcc acgcccacat agcgcatctg   1500
aagacgttgg gggagcgggg ggaggcagca gaagttcaca tgggctaa                1548
```

<210> SEQ ID NO 48
<211> LENGTH: 359
<212> TYPE: PRT
<213> ORGANISM: Nannochloropsis oculata

<400> SEQUENCE: 48

```
Met Val Phe Gln Leu Ala Arg Asp Ser Val Ser Ala Leu Val Tyr His
1               5                   10                  15

Phe Lys Glu Gly Asn Leu Asn Trp Pro Met Ile Ile Tyr Leu Val Leu
            20                  25                  30

Val His Leu Ala Gly Tyr Ile Gly Leu Thr Thr Ile Leu Ala Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Asn
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
```

```
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Ser Arg Phe Trp Gly Glu Ala
            180                 185                 190

Phe Trp Asn Ala Phe Trp Val Ala Gly Ala Leu Arg Tyr Met Leu Val
        195                 200                 205

Leu His Phe Thr Trp Met Val Asn Ser Ala Ala His Leu Tyr Gly Asp
    210                 215                 220

His Pro Tyr Asp Pro Thr Met Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Gln Gln Phe Asn Pro
            260                 265                 270

Thr Lys Ala Phe Ile Asp Phe Phe Ala Ala Ile Gly Met Val Thr Asn
        275                 280                 285

Arg Lys Arg Ala Thr Gly Ala Trp Ala Lys Leu Lys Glu Ser Arg Ala
    290                 295                 300

Arg Asp Ala Ala Asn Gly Lys Ser Met Lys Asp Phe Lys Gly Arg Gly
305                 310                 315                 320

Ser Gly Ser Asp Tyr Gly Thr Thr Asn Thr Asn Tyr Ala Val Ser Asn
                325                 330                 335

Lys Thr Val Val Thr Asp Lys Gly Ala Gln Gln Pro Gly Trp Glu Glu
            340                 345                 350

Ser Asn His Pro Lys Tyr Asn
        355


<210> SEQ ID NO 49
<211> LENGTH: 1080
<212> TYPE: DNA
<213> ORGANISM: Nannochloropsis oculata

<400> SEQUENCE: 49

atggtcttcc agctcgcccg agactctgtc tcggccctgg tctatcattt caaagaagga      60

aaccttaact ggcctatgat tatctacctc gtccttgtcc acttggcggg ctacatcggt     120

ctgactacca ttctggcttg caaatggcaa actctcctcg aagcgttcat cctatggccc     180

atcaccgggc tggggattac tgccggcgta caccgacttt gggcacaccg ttcgtacaat     240

gccacgttgc cttatcgcat cctgttgatg ttgttcaact caattgcgaa ccaaggcagc     300

atctaccact ggtcccggga ccaccgcgtg caccacaagt actccgagac tgatgctgac     360

ccacataacg ccacccgtgg cttcttcttc gcgcacatgg gctggctcat tgttaagaag     420

caccccaagg tcgtcgaagg ggggaagcaa ctcgatttct ccgatttggc tgccgatccc     480

gtggtgcgat tccagcgtga ttgggatccg tggttcgccc agtttatgtg ctttgtcatg     540

ccggcgcttg ttgcatcgag gttctggggt gaggcgttct ggaacgcctt ttgggtggcg     600

ggggctttga ggtatatgtt ggtgctgcac ttcacctgga tggttaacag tgcggcgcac     660

ttgtatggcg accacccgta cgaccctacc atgtggccgg cggagaaccc gttggtatcg     720

gtagtggcga tcggagaagg ctggcataac tggcaccatc gttacccccta cgactacgcg     780

gcttccgagt ttgggatttc gcagcagttc aacccgacca aggcgttcat tgattttttt     840
```

```
gcggccatag ggatggtgac gaaccgaaaa cgtgcgacgg gggcttgggc aaagctcaag     900

gaatccaggg caagggatgc ggcgaatggg aagagcatga aagatttcaa gggaagaggc     960

tcggggtcag actatggtac gacaaacacc aattacgcgg tgtcgaacaa gacagtggtg    1020

accgacaagg gggcgcaaca accagggtgg gaggagagca atcaccccaa gtacaactaa    1080


<210> SEQ ID NO 50
<211> LENGTH: 340
<212> TYPE: PRT
<213> ORGANISM: Nannochloropsis gaditana

<400> SEQUENCE: 50

Met Val Phe Gln Leu Ala Arg Asp Ala Leu Ser Ala Leu Val Tyr His
1               5                   10                  15

Tyr Lys Glu Gly Asn Leu Asn Trp Pro Met Ile Ile Tyr Leu Val Leu
            20                  25                  30

Ala His Leu Ala Ala Tyr Met Gly Leu Val Ser Ile Pro Ser Cys Lys
        35                  40                  45

Trp Gln Thr Leu Leu Glu Ala Phe Ile Leu Trp Pro Ile Thr Gly Leu
    50                  55                  60

Gly Ile Thr Ala Gly Val His Arg Leu Trp Ala His Arg Ser Tyr Thr
65                  70                  75                  80

Ala Thr Leu Pro Tyr Arg Ile Leu Leu Met Leu Phe Asn Ser Ile Ala
                85                  90                  95

Asn Gln Gly Ser Ile Tyr His Trp Ser Arg Asp His Arg Val His His
            100                 105                 110

Lys Tyr Ser Glu Thr Asp Ala Asp Pro His Asn Ala Thr Arg Gly Phe
        115                 120                 125

Phe Phe Ala His Met Gly Trp Leu Ile Val Lys Lys His Pro Lys Val
    130                 135                 140

Val Glu Gly Gly Lys Gln Leu Asp Phe Ser Asp Leu Ala Ala Asp Pro
145                 150                 155                 160

Val Val Arg Phe Gln Arg Asp Trp Asp Pro Trp Phe Ala Gln Phe Met
                165                 170                 175

Cys Phe Val Met Pro Ala Leu Val Ala Arg Tyr Phe Trp Gly Glu Ala
            180                 185                 190

Phe Trp Asn Ala Phe Trp Val Ala Gly Gly Leu Arg Tyr Cys Leu Val
        195                 200                 205

Leu His Phe Thr Trp Met Val Asn Ser Ala Ala His Leu Tyr Gly Asp
    210                 215                 220

His Pro Tyr Asp Pro Thr Ile Trp Pro Ala Glu Asn Pro Leu Val Ser
225                 230                 235                 240

Val Val Ala Ile Gly Glu Gly Trp His Asn Trp His His Arg Tyr Pro
                245                 250                 255

Tyr Asp Tyr Ala Ala Ser Glu Phe Gly Ile Ser Arg Gln Phe Asn Pro
            260                 265                 270

Thr Lys Ala Phe Ile Asp Phe Phe Ala Ala Ile Gly Met Val Ser Asn
        275                 280                 285

Arg Lys Arg Ala Thr Gly Ala Trp Ala Lys Leu Arg Glu Ser Arg Ala
    290                 295                 300

Lys Asp Glu Ala Asn Gly Lys Ser Ile Lys Asp Phe Arg Gly Arg Gly
305                 310                 315                 320

Val Val Gln Gly Thr Ala Gln Pro Pro Gly Trp Glu Gln Ser Ala His
                325                 330                 335
```

Pro Lys Tyr Asn
340

<210> SEQ ID NO 51
<211> LENGTH: 1023
<212> TYPE: DNA
<213> ORGANISM: Nannochloropsis gaditana

<400> SEQUENCE: 51
atggtcttcc agttggctcg cgatgccttg tcggcgcttg tctaccacta caaagagggc 60
aacctgaatt ggcccatgat catctaccta gtcctcgcgc accttgccgc ctacatgggg 120
ctggtctcca tcccttcatg caagtggcag acccttctgg aggccttcat cctgtggccc 180
atcaccgggt tgggcatcac ggccggcgtc catcgtctgt gggcgcatcg ctcctacact 240
gccaccttgc cgtaccgcat cctcctcatg ctcttcaatt cgattgcgaa tcaaggcagc 300
atctaccact ggtcccggga tcatcgcgtt caccacaagt actcggagac agatgcggat 360
cctcacaatg ccacccgtgg cttcttcttc gcgcacatgg ggtggcttat cgttaagaaa 420
cacccgaagg tagtagaagg cggcaaacag ttggatttct ctgatcttgc tgcggacccg 480
gtggtccgtt tccagcgtga ctgggacccg tggttcgcgc aattcatgtg cttcgtcatg 540
ccggcgctgg tcgccagata tttctggggt gaggcctttt ggaacgcatt ttgggttgca 600
gggggcctcc gctactgtct ggtcctgcat ttcacctgga tggtgaactc cgccgcccac 660
ttatacggcg atcaccccta cgaccccacc atctggcccg ccgagaaccc gctagtatcg 720
gtggtggcca tcggggaggg atggcacaat tggcatcacc ggtatcccta cgactatgcg 780
gcatctgagt tcgggatctc ccgacaattt aaccctacga aggctttcat tgacttcttt 840
gctgccatcg gtatggtctc gaatcgaaag cgggcgacag gggcctgggc caagctcagg 900
gagtcacggg cgaaggacga ggcgaacggg aagagcatca aagattttcg aggacgagga 960
gttgtccaag gcaccgcaca gccaccggga tgggaacaaa gcgcgcaccc caagtacaac 1020
tga 1023

<210> SEQ ID NO 52
<211> LENGTH: 35
<212> TYPE: DNA
<213> ORGANISM: Artificial Sequence
<220> FEATURE:
<223> OTHER INFORMATION: primer No. 52

<400> SEQUENCE: 52
cagcccgcat caacaatggg acgcggcggt gagaa 35

<210> SEQ ID NO 53
<211> LENGTH: 35
<212> TYPE: DNA
<213> ORGANISM: Artificial Sequence
<220> FEATURE:
<223> OTHER INFORMATION: primer No. 53

<400> SEQUENCE: 53
ctcttccaca gaagcctatg cccgctgctt gtaga 35

<210> SEQ ID NO 54
<211> LENGTH: 35
<212> TYPE: DNA
<213> ORGANISM: Artificial Sequence
<220> FEATURE:
<223> OTHER INFORMATION: primer No. 54

<400> SEQUENCE: 54
cagcccgcat caacaatggt tgagcaaacg ttacc 35

<210> SEQ ID NO 55
<211> LENGTH: 35
<212> TYPE: DNA
<213> ORGANISM: Artificial Sequence
<220> FEATURE:
<223> OTHER INFORMATION: primer No. 55

<400> SEQUENCE: 55
ctcttccaca gaagcttacg gaggggagga tgaac 35

<210> SEQ ID NO 56
<211> LENGTH: 822
<212> TYPE: DNA
<213> ORGANISM: Artificial Sequence
<220> FEATURE:
<223> OTHER INFORMATION: Paromomycin resistance gene

<400> SEQUENCE: 56
atggtcgaga ttcgaagcat ggacgatgcg ttgcgtgcac tgcggggtcg gtatcccggt 60
tgtgagtggg ttgttgtgga ggatggggcc tcgggggctg gtgtttatcg gcttcggggt 120
ggtgggcggg agttgtttgt caaggtggca gctctggggg ccggggtggg cttgttgggt 180
gaggctgaac ggctggtgtg gttggcggag gtggggattc ccgtacctcg tgttgtggag 240
ggtggtgggg acgagagggt cgcctggttg gtcaccgaag cggttccggg gcgtccggcc 300
agtgcgcggt ggccgcggga gcagcggctg gacgtggcgg tggcgctcgc ggggctcgct 360
cgttcgctgc acgcgctgga ctgggagcgg tgtccgttcg atcgcagtct cgcggtgacg 420
gtgccgcagg cggcccgtgc tgtcgctgaa gggagcgtcg acttggagga tctggacgag 480
gagcggaagg ggtggtcggg ggagcggctt ctcgccgagc tggagcggac tcggcctgcg 540
gacgaggatc tggcggtttg ccacggtgac ctgtgcccgg acaacgtgct gctcgaccct 600
cgtacctgcg aggtgaccgg gctgatcgac gtggggcggg tcggccgtgc ggaccggcac 660
tccgatctcg cgctggtgct gcgcgagctg gcccacgagg aggacccgtg gttcgggccg 720
gagtgttccg cggcgttcct gcgggagtac gggcgcgggt gggatggggc ggtatcggag 780
gaaaagctgg cgttttaccg gctgttggac gagttcttct ga 822

<210> SEQ ID NO 57
<211> LENGTH: 35
<212> TYPE: DNA
<213> ORGANISM: Artificial Sequence
<220> FEATURE:
<223> OTHER INFORMATION: primer No. 57

<400> SEQUENCE: 57 ctttttgtg aagcaatggt cgagattcga agcat 35

<210> SEQ ID NO 58
<211> LENGTH: 35
<212> TYPE: DNA
<213> ORGANISM: Artificial Sequence
<220> FEATURE:
<223> OTHER INFORMATION: primer No. 58

<400> SEQUENCE: 58
tttcccccat cccgatcaga agaactcgtc caaca 35

```
<210> SEQ ID NO 59
<211> LENGTH: 28
<212> TYPE: DNA
<213> ORGANISM: Artificial Sequence
<220> FEATURE:
<223> OTHER INFORMATION: primer No. 59

<400> SEQUENCE: 59

tgcttcacaa aaaagacagc ttcttgat                                          28


<210> SEQ ID NO 60
<211> LENGTH: 25
<212> TYPE: DNA
<213> ORGANISM: Artificial Sequence
<220> FEATURE:
<223> OTHER INFORMATION: primer No. 60

<400> SEQUENCE: 60

tcgggatggg ggaaaaaaac ctctg                                             25
```

METHOD OF PRODUCING LIPID

TECHNICAL FIELD

The present invention relates to a method of producing lipids. Further, the present invention also relates to a β-ketoacyl-ACP synthase, a gene encoding the same, and a transformant wherein the expression of the gene is enhanced, for use in this method.

BACKGROUND ART

Fatty acids are one of the principal components of lipids. In vivo, fatty acids are bonded to glycerin via an ester bond to form lipids (fats and oils) such as triacylglycerol. Further, many animals and plants also store and utilize fatty acids as an energy source. These fatty acids and lipids stored in animals and plants are widely utilized for food or industrial use.

For example, higher alcohol derivatives that are obtained by reducing higher fatty acids having approximately 12 to 18 carbon atoms are used as surfactants. Alkyl sulfuric acid ester salts, alkyl benzene sulfonic acid salts and the like are utilized as anionic surfactants. Further, polyoxyalkylene alkyl ethers, alkyl polyglycosides and the like are utilized as nonionic surfactants. These surfactants are used for detergents, disinfectants, or the like. Cationic surfactants such as alkylamine salts and mono- or dialkyl-quaternary amine salts, as other higher alcohol derivatives, are commonly used for fiber treatment agents, hair conditioning agents, disinfectants, or the like. Further, benzalkonium type quaternary ammonium salts are commonly used for disinfectants, antiseptics, or the like. Furthermore, vegetable fats and oils are also used as raw materials of biodiesel fuels.

Further, most of long-chain fatty acids having 18 or more carbon atoms, particularly long-chain polyunsaturated fatty acids into which a plurality of unsaturated bonds are introduced (hereinafter, also referred to as "PUFA") are known to be essential fatty acids which are unable to be synthesized in vivo in animals. Accordingly, such PUFA is particularly useful in nutritional use and utilized as physiologically functional food and the like.

A fatty acid synthetic pathway of plants is localized in the chloroplast. In the chloroplast, an elongation reaction of the carbon chain is repeated starting from an acetyl-ACP (acyl-carrier-protein), and finally an acyl-ACP (a composite consisting of an acyl group being a fatty acid residue and an ACP) having 16 or 18 carbon atoms is synthesized. A β-ketoacyl-ACP synthase (hereinafter, also referred to as "KAS") is an enzyme involved in control of chain length of the acyl group, among enzymes involved in the fatty acid synthetic pathway. In plants, four kinds of KASs having different function respectively, namely KAS I, KAS II, KAS III and KAS IV are known to exist. Among these, KAS III functions in a stage of starting a chain length elongation reaction to elongate the acetyl-ACP (or acetyl-CoA) having 2 carbon atoms to the β-ketoacyl-ACP having 4 carbon atoms. In the subsequent elongation reaction, KAS I, KAS II and KAS IV are involved. KAS I is mainly involved in the elongation reaction to the palmitoyl-ACP having 16 carbon atoms, and KAS II is mainly involved in the elongation reaction to the stearoyl-ACP having 18 carbon atoms. On the other hand, it is believed that KAS IV is involved in the elongation reaction to medium-chain acyl-ACP having 6 to 14 carbon atoms.

Furthermore, the long-chain fatty acids having 18 or more carbon atoms, particularly PUFA is reputedly synthesized by a number of desaturase or elongase outside the chloroplasts.

As mentioned above, fatty acids are widely used in various applications. Therefore, attempts have been made on improving productivity of the fatty acids or the lipids in vivo by using hosts such as plants. Furthermore, applications and usefulness of the fatty acids depend on the number of carbon atoms (chain length) or unsaturated bonds (degree of unsaturation) thereof. Therefore attempts have been made also on controlling the number of carbon atoms or unsaturated bonds of the fatty acids.

In general, enhancement of desaturase or elongase is considered to be effective in improving the productivity of PUFA, and these enzyme groups have been identified from various organisms (see Patent Literature 1). For example, desaturase or elongase derived from algae, being one kind of microalgae, belonged to the genus *Nannochloropsis*, on which attention is focused as a next-generation production source for fats and oils is known to be usable for synthesis of the long-chain fatty acids (see Patent Literature 2 and 3).

Thus, a method of effectively producing the lipids rich in desired long-chain fatty acids (particularly PUFA) in oleaginous organisms is in demand in the technical field.

CITATION LIST

Patent Literatures

Patent Literature 1: WO 2012/052468
Patent Literature 2: WO 2012/149457
Patent Literature 3: US 2012/0277418

SUMMARY OF INVENTION

The present invention relates to a method of producing lipids, containing the steps of:

culturing a transformant wherein the expression of a gene encoding the following protein (A) or (B) is enhanced, and producing fatty acids or lipids containing these fatty acids as components, wherein:

protein (A) is a protein consisting of the amino acid sequence set forth in SEQ ID NO: 1; and protein (B) is a protein consisting of an amino acid sequence having 70% or more identity with the amino acid sequence of the protein (A), and having β-ketoacyl-ACP synthase activity (hereinafter, also referred to as "KAS activity").

The present invention relates to the protein (A) or (B).

Further, the present invention relates to a gene encoding the protein (A) or (B).

Furthermore, the present invention relates to a transformant, wherein the expression of a gene encoding the protein (A) or (B) is enhanced.

MODE FOR CARRYING OUT THE INVENTION

The present invention relates to a method of producing lipids, which improves productivity of long-chain fatty acids or the lipids containing these fatty acids as components.

Further, the present invention relates to a transformant in which the productivity of long-chain fatty acids or the lipids containing these fatty acids as components is improved.

The present inventors newly identified, as an enzyme involved in a long-chain fatty acid synthesis, a KAS of algae of the genus *Nannochloropsis*, being one kind of algae. Then, the present inventors promoted expression of the KAS in microorganisms, and as the result, found that the productivity of long-chain fatty acids or the lipids containing these fatty acids as components to be produced, is significantly improved.

The present invention was completed based on these findings.

According to the method of producing the lipids of the present invention, the productivity of long-chain fatty acids or the lipids containing these fatty acids as components can be improved.

Moreover, the transformant of the present invention is excellent in the productivity of long-chain fatty acids or the lipids containing these fatty acids as components.

Other and further features and advantages of the invention will appear more fully from the following description.

The term "lipid(s)" in the present specification, covers simple lipid such as a neutral lipid (triacylglycerol, or the like), wax, and a ceramide; a complex lipid such as a phospholipid, a glycolipid, and a sulfolipid; and a derived lipid obtained from the lipid such as a fatty acid, alcohols, and hydrocarbons.

In the present specification, the description of "Cx:y" for the fatty acid or the acyl group constituting the fatty acid means that the number of carbon atoms is "x" and the number of double bonds is "y". The description of "Cx" means a fatty acid or an acyl group having "x" as the number of carbon atoms.

In the present specification, the identity of the nucleotide sequence and the amino acid sequence is calculated through the Lipman-Pearson method (Science, 1985, vol. 227, p. 1435-1441). Specifically, the identity can be determined through use of a homology analysis (search homology) program of genetic information processing software Genetyx-Win with Unit size to compare (ktup) being set to 2.

It should be note that, in this description, the "stringent conditions" includes, for example, the method described in Molecular Cloning—A LABORATORY MANUAL THIRD EDITION [Joseph Sambrook, David W. Russell, Cold Spring Harbor Laboratory Press], and examples thereof include conditions where hybridization is performed by incubating a solution containing 6×SSC (composition of 1×SSC: 0.15 M sodium chloride, 0.015 M sodium citrate, pH7.0), 0.5% SDS, 5×Denhardt and 100 mg/mL herring sperm DNA together with a probe at 65° C. for 8 to 16 hours.

Furthermore, in the present specification, the term "upstream" of a gene means a region subsequent to a 5' side of a targeted gene or region, and not a position from a translational initiation site. On the other hand, the term "downstream" of the gene means a region subsequent to a 3' side of the targeted gene or region.

The above-described protein (A) or (B) (hereinafter, also referred to as "NoKASII") is one of the KAS, and the protein involved in a long-chain fatty acid synthesis. The protein consisting of the amino acid sequence set forth in SEQ ID NO: 1 is one of the KAS derived from *Nannochloropsis oculata* NIES-2145 being algae belonged to the genus *Nannochloropsis*.

The KAS is an enzyme involved in control of chain length of an acyl group in the fatty acid synthetic pathway. The fatty acid synthetic pathway of plants is generally localized in the chloroplast. In the chloroplast, the elongation reaction of the carbon chain is repeated starting from an acetyl-ACP (or acetyl-CoA), and finally an acyl-ACP having 16 or 18 carbon atoms is synthesized. Then, an acyl-ACP thioesterase (hereinafter, also merely referred to as "TE") hydrolyzes the thioester bond of the acyl-ACP to form a free fatty acid.

In the first stage of the fatty acid synthesis, an acetoacetyl-ACP is formed by a condensation reaction between the acetyl-ACP (or acetyl-CoA) and a malonyl-ACP. The KAS catalyzes this reaction. Then, the keto group of the acetoacetyl-ACP is reduced by a β-ketoacyl-ACP reductase, to produce a hydroxybutyryl-ACP. Subsequently, the hydroxybutyryl-ACP is dehydrated by a β-hydroxyacyl-ACP dehydrase, to produce a crotonyl-ACP. Finally, the crotonyl-ACP is reduced by an enoyl-ACP reductase, to produce a butyryl-ACP. The butyryl-ACP in which two carbon atoms are added to the carbon chain of the acyl group of the acetyl-ACP is produced by a series of these reactions. Hereinafter, the similar reactions are repeated to cause elongation of the carbon chain of the acyl-ACP, and an acyl-ACP having 16 or 18 carbon atoms is finally synthesized.

Both proteins (A) and (B) described above have the β-ketoacyl-ACP synthase activity (hereinafter, also referred to as "KAS activity"). In the present specification, the term "KAS activity" means the activity to catalyze the condensation reaction of the acetyl-ACP (or acetyl-CoA) or the acyl-ACP with the malonyl-ACP.

The KAS activity of the protein can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or in the cultured liquid by an ordinary technique. Alternatively, the KAS activity can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction which uses acyl-ACPs, as substrates.

KAS is categorized into KAS I, KAS II, KAS III and KAS IV according to their substrate specificity. KAS III uses an acetyl-ACP (or acetyl-CoA) having 2 carbon atoms as the substrate to catalyze the elongation reaction that the number of carbon atoms is increased from 2 to 4. KAS I mainly catalyzes the elongation reaction that the number of carbon atoms is increased from 4 to 16, to synthesize the palmitoyl-ACP having 16 carbon atoms. KAS II mainly catalyzes the elongation reaction to the long-chain acyl group having 18 carbon atoms or more, to synthesize a long-chain acyl-ACP. KAS IV mainly catalyzes the elongation reaction that the acyl-ACP having 6 carbon atoms is converted to the acyl-ACP having 14 carbon atoms, to synthesize a medium-chain acyl-ACP.

As shown in Examples mentioned later, the productivity of long-chain fatty acids having 18 or 20 carbon atoms is improved in the transformant, wherein the expression of the gene encoding the protein (A) is enhanced. Therefore, the protein (A) or (B) is considered to be a KAS of the type II KAS, having the synthetic activity of long-chain β-ketoacyl-ACP which contains 18 or more carbon atoms. Further, according to localization prediction based on ChloroP (http://www.cbs.dtu.dk/services/ChloroP/), the above-described protein (A) is considered to be the KAS of a chloroplast-localized type and an N-terminal 33 amino acid residue is considered to be a chloroplast transit signal sequence. In addition, in the present specification, the term "long-chain β-ketoacyl-ACP synthetic activity" means catalytic activity of an elongation reaction of synthesis of a long-chain β-ketoacyl-ACP having 18 or more carbon atoms by applying an acyl-ACP having mainly 16 or more carbon atoms as a substrate. Moreover, in the present specification, the term "long-chain" means that the number of carbon atoms of the acyl group is 18 or more, and preferably 18 or 20.

The synthetic activity of the KAS to the long-chain β-ketoacyl-ACP can be confirmed by, for example, introducing a DNA produced by linking a gene encoding the protein to the downstream of a promoter which functions in a host cell, into a host cell which lacks a fatty acid degradation system, culturing the thus-obtained cell under the conditions suitable for the expression of the introduced gene, and analyzing any change caused thereby in the fatty acid composition of the host cell or the cultured liquid by an ordinary technique. Alternatively, the synthetic activity to the long-chain β-ketoacyl-ACP can be confirmed by allowing, in the above-described system, coexpression of TE mentioned later, and being compared with fatty acid composition in the case of allowing merely single expression of TE. Alternatively, the synthetic activity to the long-chain β-ketoacyl-ACP can be confirmed by introducing a DNA produced by linking a gene encoding the protein to the downstream of a promoter which functions in a host cell, into a host cell, culturing the thus-obtained cell under the conditions suitable for the expression of the introduced gene, and subjecting a disruption liquid of the cell to a chain length elongation reaction.

In the protein (B), the identity with the amino acid sequence of the protein (A) is preferably 75% or more, more preferably 80% or more, further preferably 85% or more, further preferably 90% or more, further preferably 92% or more, further preferably 95% or more, further preferably 98% or more, and furthermore preferably 99% or more, in view of KAS activity. Further, specific examples of the protein (B) include a protein in which 1 or several (for example 1 or more and 142 or less, preferably 1 or more and 118 or less, more preferably 1 or more and 95 or less, further preferably 1 or more and 71 or less, furthermore preferably 1 or more and 47 or less, furthermore preferably 1 or more and 38 or less, furthermore preferably 1 or more and 23 or less, furthermore preferably 1 or more and 9 or less, and furthermore preferably 1 or more and 4 or less) amino acids are deleted, substituted, inserted or added to the amino acid sequence of the protein (A).

A method of introducing the mutation into an amino acid sequence includes a method of, for example, introducing a mutation into a nucleotide sequence encoding the amino acid sequence. A method of introducing the mutation includes a method of introducing a site-specific mutation. Specific examples of the method of introducing the site-specific mutation include a method of utilizing the SOE-PCR reaction, the ODA method, and the Kunkel method. Further, commercially available kits such as Site-Directed Mutagenesis System Mutan-Super Express Km kit (Takara Bio), Transformer TM Site-Directed Mutagenesis kit (Clontech Laboratories), and KOD-Plus-Mutagenesis Kit (TOYOBO) can also be utilized. Furthermore, a gene containing a desired mutation can also be obtained by introducing a genetic mutation at random, and then performing an evaluation of the enzyme activities and a gene analysis thereof by an appropriate method.

The proteins (A) and (B) can be obtained by chemical techniques, genetic engineering techniques or the like that are ordinarily carried out. For example, a natural product-derived protein can be obtained through isolation, purification and the like from *Nannochloropsis oculata*. In addition, the proteins (A) and (B) can be obtained by artificial chemical synthesis based on the amino acid sequence set forth in SEQ ID NO: 1. Alternatively, as recombinant proteins, proteins (A) and (B) may also be produced by gene recombination technologies. In the case of producing a recombinant protein, the β-ketoacyl-ACP synthase gene described below can be used.

Note that the algae such as *Nannochloropsis oculata* can be obtained from culture collection such as private or public research institutes or the like. For example, *Nannochloropsis oculata* NIES-2145 can be obtained from National Institute for Environmental Studies (NIES).

An example of the gene encoding the protein (A) or (B) (hereinafter, also referred to as "KAS gene") includes a gene consisting of the following DNA (a) or (b) (hereinafter, also referred to as "NoKASII gene").

(a) a DNA consisting of the nucleotide sequence set forth in SEQ ID NO: 2; and (b) a DNA consisting of a nucleotide sequence having 70% or more identity with the nucleotide sequence of the DNA (a), and encoding the protein (A) or (B) having β-ketoacyl-ACP synthase activity.

The nucleotide sequence set forth in SEQ ID NO: 2 is a nucleotide sequence of a gene encoding a protein (KAS derived from *Nannochloropsis oculata* NIES-2145) consisting of the amino acid sequence set forth in SEQ ID NO: 1.

In the DNA (b), the identity with the nucleotide sequence of the DNA (a) is preferably 75% or more, more preferably 80% or more, further preferably 85% or more, further preferably 90% or more, further preferably 92% or more, further preferably 95% or more, further preferably 98% or more, and furthermore preferably 99% or more, in view of KAS activity.

Further, the DNA (b) is also preferably a DNA in which 1 or several (for example 1 or more and 428 or less, preferably 1 or more and 357 or less, more preferably 1 or more and 285 or less, further preferably 1 or more and 214 or less, furthermore preferably 1 or more and 142 or less, furthermore preferably 1 or more and 114 or less, furthermore preferably 1 or more and 71 or less, furthermore preferably 1 or more and 28 or less, and furthermore preferably 1 or more and 14 or less) nucleotides are deleted, substituted, inserted or added to the nucleotide sequence set forth in SEQ ID NO: 2, and encoding a protein having KAS activity.

Furthermore, the DNA (b) is also preferably a DNA capable of hybridizing with a DNA consisting of the nucleotide sequence complementary with the DNA (a) under a stringent condition, and encoding the protein having KAS activity.

A method of promoting the expression of the KAS gene can be appropriately selected from an ordinarily method. For example, a method of introducing the KAS gene into a host, and a method of modifying expression regulation regions of the gene (promoter, terminator, or the like) in a host having the KAS gene on a genome, can be selected.

Hereinafter, in the present specification, a cell in which expression of a gene encoding a target protein herein is promoted is also referred to as the "transformant", and a cell in which the expression of the gene encoding the target protein is not promoted is also referred to as the "host" or "wild type strain".

In the transformant used in the present invention, the ability to produce long-chain fatty acids or lipids containing these long-chain fatty acids as components (a production amount of long-chain fatty acids or lipids containing these long-chain fatty acids as components, or a ratio (proportion) of long-chain fatty acids or lipids containing these long-chain fatty acids as components in the total fatty acids or lipids to be produced) is significantly improved, in comparison with a host. Moreover, as a result, in the transformant, the fatty acid composition in the lipid is modified. Therefore, the present invention using the transformant can be preferably applied to production of lipids having specific number of carbon atoms, particularly long-chain fatty acids or lipids containing these long-chain fatty acids as components, preferably fatty acids having 18 or more carbon atoms or lipids containing these fatty acids as components, more preferably fatty acids having 18 to 22 carbon atoms or lipids containing these fatty acids as components, further preferably fatty acids having 18 to 20 carbon atoms or lipids containing these fatty acids as components, further preferably fatty acids having 18 or 20 carbon atoms or lipids containing these fatty acids as components, further preferably unsaturated fatty acids having 18 or 20 carbon atoms or lipids containing these fatty acids as components, furthermore preferably C18:1, C18:2, C18:3, C20:4 or C20:5 fatty acids or lipids containing these fatty acids as components, further preferably PUFA having 18 or 20 carbon atoms or lipids containing these fatty acids as components, further preferably PUFA having 20 carbon atoms or lipids containing these fatty acids, furthermore preferably C20:4 or C20:5 fatty acids or lipids containing these fatty acids, and still further preferably eicosapentaenoic acid (hereinafter, also referred to as "EPA") or lipids containing the EPA as components.

Moreover, in the transformant of the present invention, the ratio of the amount of long-chain fatty acids or the amount of ester compound thereof, in the total amount of all fatty acids or fatty acid ester consisting of the ester compound thereof is improved. The long-chain fatty acids are preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4 or C20:5 fatty acids, more preferably PUFA having 18 or 20 carbon atoms, more preferably PUFA having 20 carbon atoms, more preferably 020:4 or C20:5 fatty acids, and more preferably EPA.

The ability to produce fatty acids and lipids of the host and the transformant can be measured by the method used in Examples described below.

The method of introducing the KAS gene into a host and promoting the expression of the gene is described.

The KAS gene can be obtained by genetic engineering techniques that are ordinarily carried out. For example, the KAS gene can be artificially synthesized based on the amino acid sequence set forth in SEQ ID NO: 1 or the nucleotide sequence set forth in SEQ ID NO: 2. The synthesis of the KAS gene can be achieved by utilizing, for example, the services of Invitrogen. Further, the gene can also be obtained by cloning from *Nannochloropsis oculata*. The cloning can be carried out by, for example, the methods described in Molecular Cloning: A LABORATORY MANUAL THIRD EDITION [Joseph Sambrook, David W. Russell, Cold Spring Harbor Laboratory Press (2001)]. Furthermore, *Nannochloropsis oculata* NIES-2145 used in Examples can be obtained from National Institute for Environmental Studies (NIES).

The transformant that can be preferably used in the present invention is obtained by introducing the KAS gene into a host according to an ordinarily method. Specifically, the transformant can be produced by preparing a recombinant vector or a gene expression cassette which is capable of expressing the KAS gene in a host cell, introducing this vector or cassette into host cell, and thereby transforming the host cell.

The host for the transformant can be appropriately selected from ordinarily used hosts. For example, microorganisms (including algae and microalgae), plants or animals can be used as the host in the present invention. Among these, microorganisms or plants are preferable, microorganisms are more preferable, and microalgae are further preferable as a host, from the viewpoints of production efficiency and the usability of lipids to be obtained.

As the microorganisms, prokaryotes and eukaryotes can be used. Prokaryotes include microorganisms belonging to the genus *Escherichia*, microorganisms belonging to the genus *Bacillus*, microorganisms belonging to the genus *Synechocystis*, microorganisms belonging to the genus *Synechococcus*, or the like. Eukaryotes include eukaryotic microorganisms belonging to yeast, filamentous fungi or the like. Among these, from a viewpoint of the productivity of lipids, *Escherichia coli, Bacillus subtilis, Rhodosporidium toruloides*, or *Mortierella* sp., is preferable, and *Escherichia coli* is more preferable.

As the algae or microalgae, from a viewpoint of establishment of a gene recombination technique, algae belonging to the genus *Chlamydomonas*, algae belonging to the genus *Chlorella*, algae belonging to the genus *Phaeodactylum*, or algae belonging to the genus *Nannochloropsis* are preferable, and algae belonging to the genus *Nannochloropsis* are more preferable. Specific examples of the algae belonging to the genus *Nannochloropsis* include *Nannochloropsis oculata, Nannochloropsis qaditana, Nannochloropsis salina, Nannochloropsis oceanica, Nannochloropsis atomus, Nannochloropsis maculata, Nannochloropsis granulata*, and *Nannochloropsis* sp. Among these, from a viewpoint of the productivity of lipids, *Nannochloropsis oculata* or *Nannochloropsis* qaditana is preferable, and *Nannochloropsis oculata* is more preferable.

As the plants, from a viewpoint of a high lipid content of seeds, *Arabidopsis thaliana, Brassica napus, Brassica raga, Cocos nucifera, Elaeis guineensis, cuphea, Glycine max, Zea mays, Oryza sativa, Helianthus annuus, Cinnamomum camphora*, or *Jatropha curcas* is preferable, and *Arabidopsis thaliana* is more preferable.

A vector for use as the plasmid vector for gene expression or a vector containing the gene expression cassette (plasmid) may be any vector capable of introducing the gene encoding the target protein into a host, and expressing the gene in the host cell. For example, a vector which has expression regulation regions such as a promoter and a terminator in accordance with the type of the host to be introduced, and has a replication initiation point, a selection marker or the like, can be used. Furthermore, the vector may also be a vector such as a plasmid capable of self-proliferation and self-replication outside the chromosome, or may also be a vector which is incorporated into the chromosome.

Specific examples of the vector that can be used preferably in the present invention include, in the case of using a microorganism as the host, pBluescript (pBS) II SK(−) (manufactured by Stratagene), a pSTV-based vector (manufactured by Takara Bio), a pUC-based vector (manufactured by Takara Shuzo), a pET-based vector (manufactured by Takara Bio), a pGEX-based vector (manufactured by GE Healthcare), a pCold-based vector (manufactured by Takara Bio), pHY300PLK (manufactured by Takara Bio), pUB110 (McKenzie, T. et al., 1986, Plasmid 15(2), p. 93-103), pBR322 (manufactured by Takara Bio), pRS403 (manufactured by Stratagene), and pMW218/219 (manufactured by Nippon Gene). In particular, in the case of using *Escherichia coli* as the host, pBluescript II SK(−) or pMW218/219 is preferably used.

When the algae or the microalgae are used as the host, specific examples of the vector include pUC19 (manufactured by Takara Bio), P66 (*Chlamydomonas* Center), P-322 (*Chlamydomonas* Center), pPha-T1 (see Yangmin Gong, et al., Journal of Basic Microbiology, 2011, vol. 51, p. 666-672) and pJET1 (manufactured by COSMO BIO). In particular, in the case of using the algae belonging to the genus *Nannochloropsis* as the host, pUC19, pPha-T1 or pJET1 is preferably used. Moreover, when the host is the algae belonging to the genus *Nannochloropsis*, the host can be transformed, with referring to the method described in Oliver Kilian, et al., Proceedings of the National Academy of Sciences of the United States of America, 2011, vol. 108(52), by using the DNA fragment consisting of the target gene of the present invention, a promoter and a terminator (gene expression cassette). Specific examples of this DNA fragment include a PCR-amplified DNA fragment and a restriction enzyme-cut DNA fragment.

In the case of using a plant cell as the host, examples of the vector include a pRI-based vector (manufactured by Takara Bio), a pBI-based vector (manufactured by Clontech), and an IN3-based vector (manufactured by Inplanta Innovations). In particular, in the case of using *Arabidopsis thaliana* as the host, a pRI-based vector or a pBI-based vector is preferably used.

Moreover, a kind of promoter regulating the expression of the gene encoding a target protein, which is introduced into the expression vector, can also be appropriately selected according to a kind of the host to be used. Specific examples of the promoter that can be preferably used in the present invention include lac promoter, trp promoter, tac promoter, trc promoter, T7 promoter, SpoVG promoter, a promoter that relates to a substance that can be induced by addition of isopropyl β-D-1-thiogalactopyranoside (IPTG), Rubisco operon (rbc), PSI reaction center protein (psaAB), D1 protein of PSII (psbA), cauliflower mosaic virus 35S RNA promoter, promoters for housekeeping genes (e.g., tubulin promoter, actin promoter and ubiquitin promoter), *Brassica napus* or *Brassica rapa*-derived Napin gene promoter, plant-derived Rubisco promoter, a promoter of a violaxanthin/(chlorophyll a)-binding protein gene derived from the genus *Nannochloropsis* (VCP1 promoter, VCP2 promoter) (Oliver Kilian, et al., Proceedings of the National Academy of Sciences of the United States of America, 2011, vol. 108 (52)), and a promoter of an oleosin-like protein LDSP (lipid droplet surface protein) gene derived from the genus *Nannochloropsis* (Astrid Vieler, et al., PLOS Genetics, 2012, vol. 8(11): e1003064. DOI: 10.1371). In the case of using *Nannochloropsis* as the host in the present invention, the promoter of violaxanthin/(chlorophyll a)-binding protein gene, or the promoter of an oleosin-like protein LDSP gene derived from the genus *Nannochloropsis* can be preferably used.

Moreover, a kind of selection marker for confirming introduction of the gene encoding a target protein can also be appropriately selected according to a kind of the host to be used. Examples of the selection marker that can be preferably used in the present invention include drug resistance genes such as an ampicillin resistance gene, a chloramphenicol resistance gene, an erythromycin resistance gene, a neomycin resistance gene, a kanamycin resistance gene, a spectinomycin resistance gene, a tetracycline resistance gene, a blasticidin S resistance gene, a bialaphos resistance gene, a zeocin resistance gene, a paromomycin resistance gene, and a hygromycin resistance gene. Further, it is also possible to use a deletion of an auxotrophy-related gene or the like as the selection marker gene.

Introduction of the gene encoding a target protein to the vector can be conducted by an ordinary technique such as restriction enzyme treatment and ligation.

Furthermore, the method for transformation can be appropriately selected from ordinary techniques according to a kind of the host to be used. For example, a transformation method of using calcium ion, a general competent cell transformation method, a protoplast transformation method, an electroporation method, an LP transformation method, a method of using *Agrobacterium*, a particle gun method, or the like can be used. When the algae belonging to the genus *Nannochloropsis* are used as the host, transformation can also be performed by using the electroporation method described in Randor Radakovits, et al., Nature Communications, DOI: 10.1038/ncomms1688, 2012, or the like.

The selection of a transformant having a target gene fragment introduced therein can be carried out by utilizing the selection marker or the like. For example, the selection can be carried out by using an indicator whether a transformant acquires the drug resistance as a result of introducing a drug resistance gene into a host cell together with a target DNA fragment upon the transformation. Further, the introduction of a target DNA fragment can also be confirmed by PCR using a genome as a template or the like.

In a host having the KAS gene on a genome, a method of modifying expression regulation regions of the gene and promoting the expression of the gene is described.

The "expression regulation region" indicates the promoter or the terminator, in which these sequences are generally involved in regulation of the expression amount (transcription amount, translation amount) of the gene adjacent thereto. In a host having the above-described KAS gene on a genome, productivity of long-chain fatty acids or lipids containing these long-chain fatty acids as components can be improved by modifying expression regulation regions of the gene and promoting the expression of the KAS gene.

Specific examples of the method of modifying the expression regulation regions include interchange of promoters. In the host having the above-mentioned KAS gene on the genome, the expression of the above-described KAS gene can be enhanced by interchanging the promoter of the gene (hereinafter, also referred to as "KAS promoter") with a promoter having higher transcriptional activity. For example, in *Nannochloropsis oculata* NIES-2145 strain being one of the hosts having the KAS genes on the genome, the NoKASII gene exists at the downstream of a DNA sequence consisting of the nucleotide sequence set forth in SEQ ID NO: 23, and a promoter region exists in the DNA sequence consisting of the nucleotide sequence set forth in SEQ ID NO: 23. The expression of the above-described KAS gene can be enhanced by partially or wholly interchanging the DNA sequences consisting of the nucleotide sequence set forth in SEQ ID NO: 23 with the promoter having higher transcriptional activity.

The promoter used for interchanging the KAS promoter is not particularly limited, and can be appropriately selected from the promoters that are higher in the transcriptional activity than the KAS promoter and suitable for production of the long-chain fatty acids or the lipids containing these fatty acids as components.

When the host is *Nannochloropsis*, a tubulin promoter, a heat shock protein promoter, the above-described promoter of a violaxanthin/(chlorophyll a)-binding protein gene (VCP1 promoter, VCP2 promoter), and a promoter of an oleosin-like protein LDSP gene derived from the genus *Nannochloropsis* (SEQ ID NO: 6), can be preferably used. From a viewpoint of improvement in the productivity of long-chain fatty acids or lipids containing these long-chain fatty acids as components, the promoter of a violaxanthin/(chlorophyll a)-binding protein gene and the promoter of LDSP gene are more preferable, and the promoter of LDSP gene is furthermore preferable.

The above-described modification of a promoter can employ according to an ordinarily method such as homologous recombination. Specifically, a linear DNA fragment containing an upstream and downstream regions of a target promoter and containing other promoter instead of the target promoter is constructed, and the resultant DNA fragment is incorporated into a host cell to cause double crossover homologous recombination on the side upstream and downstream of the target promoter of the host genome. Then the target promoter on the genome is substituted with other promoter fragment, and the promoter can be modified.

The method of modifying a target promoter according to such homologous recombination can be conducted with, for example, reference to literature such as Besher et al., Methods in molecular biology, 1995, vol. 47, p. 291-302. In particular, when the host is the algae belonging to the genus *Nannochloropsis*, specific region in a genome can be modified, with referring to literature such as Oliver Kilian, et al., Proceedings of the National Academy of Sciences of the United States of America, 2011, vol. 108(52), by homologous recombination method.

The transformant of the present invention preferably has enhancing expression of a gene encoding a TE (hereinafter, also referred to as "TE gene"), in addition to the gene encoding the protein (A) or (B)

As described above, TE is an enzyme that hydrolyzes the thioester bond of the acyl-ACP synthesized by a fatty acid synthase such as the KAS to produce a free fatty acid. The function of the TE terminates the fatty acid synthesis on the ACP, and then the thus-hydrolyzed fatty acid is supplied to the synthesis of PUFA or triacylglycerol (hereinafter, also referred to as "TAG") or the like. Therefore, lipid productivity, particularly productivity of fatty acids of the transformant to be used for the lipid production, can be further improved by enhancing the expression of the TE gene, in addition to the KAS gene.

The TE that can be used in the present invention merely needs to be the protein having acyl-ACP thioesterase activity (hereinafter, also referred to as "TE activity"). Herein, the term "TE activity" means an activity of hydrolyzing the thioester bond of the acyl-ACP.

To date, several TEs having different reaction specificities depending on the number of carbon atoms and the number of unsaturated bonds of the acyl group (fatty acid residue) constituting the acyl-ACP substrate are identified. Therefore, TE, as similar to KAS, is considered to be an important factor in determining the fatty acid composition of an organism. In particular, when a host originally having no genes encoding a TE is used in the transformation, introduction of genes encoding a TE, preferably genes encoding a TE having substrate specificity to the long-chain acyl-ACP is effective. The productivity of long-chain fatty acids is further improved by introducing such a gene.

The TE that can be used in the present invention can be appropriately selected from ordinary TEs and proteins functionally equivalent to the TEs, according to a kind of host or the like. Specific examples thereof that can be used include FatA derived from *Arabidopsis thaliana* (SEQ ID NO: 24), FatB derived from *Arabidopsis thaliana* (SEQ ID NO: 25), FatA derived from *Garcinia mangostana* (SEQ ID NO: 26), TE derived from *Nannochloropsis qaditana* (SEQ ID NO: 27), TE derived from *Nannochloropsis oculata* (SEQ ID NO: 28 or 30), TE derived from *Nannochloropsis qranulata* (SEQ ID NO: 29), tesA derived from *Escherichia coli* (SEQ ID NO: 31), or the like. From a viewpoint of the substrate specificity for long-chain acyl-ACP, FatA derived from *Arabidopsis thaliana* or FatA derived from *Garcinia mangostana* is more preferable.

Further, the transformants in which expression of the gene TE is promoted can be prepared by an ordinary method. For example, the transformants can be prepared by a method similar to the above-mentioned method for promoting expression of the KAS gene, such as a method of introducing a TE gene into a host, and a method of modifying expression regulation regions of a gene in a host having the TE gene on a genome.

Furthermore, in the transformant of the present invention, the expression of at least one kind of gene selected from the group consisting of a gene encoding a desaturase (hereinafter, also referred to as "desaturase gene") and a gene encoding an elongase (hereinafter, also referred to as "elongase gene"), in addition to the above-described gene encoding the protein (A) or (B), is also preferably promoted.

As mentioned above, the long-chain fatty acid having 18 or more carbon atoms, particularly PUFA is reputedly synthesized by a number of desaturase or elongase outside the chloroplasts. Therefore, the productivity of the long-chain fatty acid, particularly PUFA can be further improved by promoting the expression of the gene encoding a desaturase or elongase, in addition to the KAS gene.

The desaturase or elongase, which can be used in the present invention, can be appropriately selected from the normal desaturase or elongase, or proteins functionally equivalent to the desaturase or elongase, according to a kind of host or the like. Specific examples thereof include a desaturase or elongase derived from *Nannochloropsis oculata*, described in Patent Literature 1 to 3.

Examples of the desaturase which can be used in the present invention include a Δ12-desaturase (hereinafter, also referred to as "Δ12-DES"), a Δ6-desaturase (hereinafter, also referred to as "Δ6-DES"), a ω3-desaturase (hereinafter, also referred to as "ω3-DES"), a Δ5-desaturase (hereinafter, also referred to as "Δ5-DES"), and a Δ9-desaturase (hereinafter, also referred to as "Δ9-DES").

In addition, in the present invention, the desaturase may be used alone or in combination with 2 or more kinds thereof.

In the present specification, the term "Δ12-DES" means a protein (enzyme) that catalyzes a reaction of introducing an unsaturated bond into a Δ12-position of oleic acid to form linoleic acid. Then, in the present specification, the term "Δ12-desaturase activity" (hereinafter, also referred to as "Δ12-DES activity") means activity for introducing the unsaturated bond into the Δ12-position of oleic acid. It can be confirmed that the protein has the Δ12-DES activity by a system using a Δ12-DES gene deletion strain, for example. Alternatively, it can also be confirmed by examining formation of linoleic acid by introducing the DNA of which a gene encoding the above-described protein was ligated downstream of a promoter functioning inside a host cell, into the Δ12-DES gene deletion strain. Alternatively, it can also be confirmed by measuring a decrease of oleic acid amount or an increase of linoleic acid amount according to an ordinary method by preparing the Δ12-DES or cell lysate containing the same to react the resultant material with the reaction solution containing oleic acid, oleoyl-CoA, or the like.

The Δ12-DES, which can be preferably used in the present invention, can be appropriately selected from the normal Δ12-DES or proteins functionally equivalent to the Δ12-DES, according to a kind of host or the like. Specific examples thereof include a Δ12-DES derived from *Nannochloropsis oculata* (hereinafter, also referred to as "NoΔ12-DES") (SEQ ID NO: 32), and a Δ12-DES derived from *Nannochloropsis gaditana* (hereinafter, also referred to as "NgΔ12-DES") (SEQ ID NO: 34). Moreover, as the proteins functionally equivalent to the Δ12-DES, a protein consisting of an amino acid sequence having 60% or more (preferably 70% or more, more preferably 80% or more, and further preferably 90% or more) identity with the amino acid sequence of NoΔ12-DES or NgΔ12-DES, and having Δ12-DES activity, can be also used. Examples of the gene encoding the NoΔ12-DES include a gene consisting of a DNA consisting of the nucleotide sequence set forth in SEQ ID NO: 33; and a gene consisting of a DNA consisting of a nucleotide sequence having 60% or more (preferably 70% or more, more preferably 80% or more, and further preferably 90% or more) identity with the nucleotide sequence set forth in SEQ ID NO: 33, and encoding a protein having Δ12-DES activity. Examples of the gene encoding the NgΔ12-DES include a gene consisting of a DNA consisting of the nucleotide sequence set forth in SEQ ID NO: 35; and a gene consisting of a DNA consisting of a nucleotide sequence having 60% or more (preferably 70% or more, more preferably 80% or more, and further preferably 90% or more) identity with the nucleotide sequence set forth in SEQ ID NO: 35, and encoding a protein having Δ12-DES activity.

In the present specification, the term "Δ6-DES" means a protein (enzyme) that catalyzes a reaction of introducing an unsaturated bond into a Δ6-position of linoleic acid to form γ-linolenic acid. Then, in the present specification, the term "Δ6-desaturase activity" (hereinafter, also referred to as "Δ6-DES activity") means activity for introducing the unsaturated bond into the Δ6-position of linoleic acid. It can be confirmed that the protein has the Δ6-DES activity by a system using a Δ6-DES gene deletion strain, for example. Alternatively, it can also be confirmed by examining formation of γ-linolenic acid by introducing the DNA of which a gene encoding the above-described protein was ligated downstream of a promoter functioning inside a host cell, into the Δ6-DES gene deletion strain. Alternatively, it can also be confirmed by measuring a decrease of linoleic acid amount or an increase of γ-linolenic acid amount according to an ordinary method by preparing the Δ6-DES or cell lysate containing the same to react the resultant material with the reaction solution containing linoleic acid, linoleoyl-CoA, or the like.

The Δ6-DES, which can be preferably used in the present invention, can be appropriately selected from the normal Δ6-DES or proteins functionally equivalent to the Δ6-DES, according to a kind of host or the like. Specific examples thereof include a Δ6-DES derived from *Nannochloropsis oculata* (hereinafter, also referred to as "NoΔ6-DES") (SEQ ID NO: 36), and a Δ6-DES derived from *Nannochloropsis qaditana* (hereinafter, also referred to as "NgΔ6-DES") (SEQ ID NO: 38). Moreover, as the proteins functionally equivalent to the Δ6-DES, a protein consisting of an amino acid sequence having 60% or more (preferably 70% or more, more preferably 80% or more, and further preferably 90% or more) identity with the amino acid sequence of NoΔ6-DES or NgΔ6-DES, and having Δ6-DES activity, can be also used. Examples of the gene encoding the NoΔ6-DES include a gene consisting of a DNA consisting of the nucleotide sequence set forth in SEQ ID NO: 37; and a gene consisting of a DNA consisting of a nucleotide sequence having 60% or more (preferably 70% or more, more preferably 80% or more, and further preferably 90% or more) identity with the nucleotide sequence set forth in SEQ ID NO: 37, and encoding a protein having Δ6-DES activity. Examples of the gene encoding the NgΔ6-DES include a gene consisting of a DNA consisting of the nucleotide sequence set forth in SEQ ID NO: 39; and a gene consisting of a DNA consisting of a nucleotide sequence having 60% or more (preferably 70% or more, more preferably 80% or more, and further preferably 90% or more) identity with the nucleotide sequence set forth in SEQ ID NO: 39, and encoding a protein having Δ6-DES activity.

In the present specification, the term "ω3-DES" means a protein (enzyme) that catalyzes a reaction of introducing an unsaturated bond into a ω3-position of arachidonic acid to form EPA. Then, in the present specification, the term "ω3-desaturase activity" (hereinafter, also referred to as "ω3-DES activity") means activity for introducing the unsaturated bond into the ω3-position of arachidonic acid. It can be confirmed that the protein has the ω3-DES activity by a system using a ω3-DES gene deletion strain, for example. Alternatively, it can also be confirmed by examining formation of EPA by introducing the DNA of which a gene encoding the above-described protein was ligated downstream of a promoter functioning inside a host cell, into the ω3-DES gene deletion strain. Alternatively, it can also be confirmed by measuring a decrease of arachidonic acid amount or an increase of EPA amount according to an ordinary method by preparing the ω3-DES or cell lysate containing the same to react the resultant material with the reaction solution containing arachidonic acid derivatives (the thioester compound with CoA, the ester compound with glycerol, or the like).

The ω3-DES, which can be preferably used in the present invention, can be appropriately selected from the normal ω3-DES or proteins functionally equivalent to the ω3-DES, according to a kind of host or the like. Specific examples thereof include a ω3-DES derived from *Nannochloropsis oculata* (hereinafter, also referred to as "Noω3-DES") (SEQ ID NO: 40), and a ω3-DES derived from *Nannochloropsis gaditana* (hereinafter, also referred to as "Ngω3-DES") (SEQ ID NO: 42). Moreover, as the proteins functionally equivalent to the ω3-DES, a protein consisting of an amino acid sequence having 60% or more (preferably 70% or more, more preferably 80% or more, and further preferably 90% or more) identity with the amino acid sequence of Noω3-DES or Ngω3-DES, and having ω3-DES activity, can be also used. Examples of the gene encoding the Noω3-DES include a gene consisting of a DNA consisting of the nucleotide sequence set forth in SEQ ID NO: 41; and a gene consisting of a DNA consisting of a nucleotide sequence having 60% or more (preferably 70% or more, more preferably 80% or more, and further preferably 90% or more) identity with the nucleotide sequence set forth in SEQ ID NO: 41, and encoding a protein having ω3-DES activity. Examples of the gene encoding the Ngω3-DES include a gene consisting of a DNA consisting of the nucleotide sequence set forth in SEQ ID NO: 43; and a gene consisting of a DNA consisting of a nucleotide sequence having 60% or more (preferably 70% or more, more preferably 80% or more, and further preferably 90% or more) identity with the nucleotide sequence set forth in SEQ ID NO: 43, and encoding a protein having ω3-DES activity.

In the present specification, the term "Δ5-DES" means a protein (enzyme) that catalyzes a reaction of introducing an unsaturated bond into a Δ5-position of dihomo-γ-linolenic acid to form arachidonic acid. Then, in the present specification, the term "Δ5-desaturase activity" (hereinafter, also referred to as "Δ5-DES activity") means activity for introducing the unsaturated bond into the Δ5-position of dihomo-γ-linolenic acid. It can be confirmed that the protein has the Δ5-DES activity by a system using a Δ5-DES gene deletion strain, for example. Alternatively, it can also be confirmed by examining formation of arachidonic acid by introducing the DNA of which a gene encoding the above-described protein was ligated downstream of a promoter functioning inside a host cell, into the Δ5-DES gene deletion strain. Alternatively, it can also be confirmed by measuring a decrease of dihomo-γ-linolenic acid amount or an increase of arachidonic acid amount according to an ordinary method by preparing the Δ5-DES or cell lysate containing the same to react the resultant material with the reaction solution containing dihomo-γ-linolenic acid derivatives (the thioester compound with CoA, the ester compound with glycerol, or the like).

The Δ5-DES, which can be preferably used in the present invention, can be appropriately selected from the normal Δ5-DES or proteins functionally equivalent to the Δ5-DES, according to a kind of host or the like. Specific examples thereof include a Δ5-DES derived from *Nannochloropsis oculata* (hereinafter, also referred to as "NoΔ5-DES") (SEQ ID NO: 44), and a Δ5-DES derived from *Nannochloropsis gaditana* (hereinafter, also referred to as "NgΔ5-DES") (SEQ ID NO: 46). Moreover, as the proteins functionally equivalent to the Δ5-DES, a protein consisting of an amino acid sequence having 60% or more (preferably 70% or more, more preferably 80% or more, and further preferably 90% or more) identity with the amino acid sequence of NoΔ5-DES or NgΔ5-DES, and having Δ5-DES activity, can be also used. Examples of the gene encoding the NoΔ5-DES include a gene consisting of a DNA consisting of the nucleotide sequence set forth in SEQ ID NO: 45; and a gene consisting of a DNA consisting of a nucleotide sequence having 60% or more (preferably 70% or more, more preferably 80% or more, and further preferably 90% or more) identity with the nucleotide sequence set forth in SEQ ID NO: 45, and encoding a protein having Δ5-DES activity. Examples of the gene encoding the NgΔ5-DES include a gene consisting of a DNA consisting of the nucleotide sequence set forth in SEQ ID NO: 47; and a gene consisting of a DNA consisting of a nucleotide sequence having 60% or more (preferably 70% or more, more preferably 80% or more, and further preferably 90% or more) identity with the nucleotide sequence set forth in SEQ ID NO: 47, and encoding a protein having Δ5-DES activity.

In the present specification, the term "Δ9-DES" means a protein (enzyme) that catalyzes a reaction of introducing an unsaturated bond into a Δ9-position of stearic acid (hereinafter, also referred to as "018:0") to form oleic acid. Then, in the present specification, the term "Δ9-desaturase activity" (hereinafter, also referred to as "Δ9-DES activity") means activity for introducing the unsaturated bond into the Δ9-position of stearic acid. It can be confirmed that the protein has the Δ9-DES activity by a system using a Δ9-DES gene deletion strain, for example. Alternatively, it can also be confirmed by examining formation of oleic acid by introducing the DNA of which a gene encoding the above-described protein was ligated downstream of a promoter functioning inside a host cell, into the Δ9-DES gene deletion strain. Alternatively, it can also be confirmed by measuring a decrease of stearic acid amount or an increase of oleic acid amount according to an ordinary method by preparing the Δ9-DES or cell lysate containing the same to react the resultant material with the reaction solution containing stearic acid, stearoyl-CoA, or the like.

The Δ9-DES, which can be preferably used in the present invention, can be appropriately selected from the normal Δ9-DES or proteins functionally equivalent to the Δ9-DES, according to a kind of host or the like. Specific examples thereof include a Δ9-DES derived from *Nannochloropsis oculata* (hereinafter, also referred to as "NoΔ9-DES") (SEQ ID NO: 48), and a Δ9-DES derived from *Nannochloropsis qaditana* (hereinafter, also referred to as "NgΔ9-DES") (SEQ ID NO: 50). Moreover, as the proteins functionally equivalent to the Δ9-DES, a protein consisting of an amino acid sequence having 60% or more (preferably 70% or more, more preferably 80% or more, and further preferably 90% or more) identity with the amino acid sequence of NoΔ9-DES or NgΔ9-DES, and having Δ9-DES activity, can be also used. Examples of the gene encoding the NoΔ9-DES include a gene consisting of a DNA consisting of the nucleotide sequence set forth in SEQ ID NO: 49; and a gene consisting of a DNA consisting of a nucleotide sequence having 60% or more (preferably 70% or more, more preferably 80% or more, and further preferably 90% or more) identity with the nucleotide sequence set forth in SEQ ID NO: 49, and encoding a protein having Δ9-DES activity. Examples of the gene encoding the NgΔ9-DES include a gene consisting of a DNA consisting of the nucleotide sequence set forth in SEQ ID NO: 51; and a gene consisting of a DNA consisting of a nucleotide sequence having 60% or more (preferably 70% or more, more preferably 80% or more, and further preferably 90% or more) identity with the nucleotide sequence set forth in SEQ ID NO: 51, and encoding a protein having Δ9-DES activity.

Further, the transformants in which the expression of the desaturase gene or the elongase gene is promoted can be prepared by an ordinary method. For example, the transformants can be prepared by a method similar to the above-described method for promoting the expression of the KAS gene, such as a method for introducing a gene encoding the desaturase or the elongase into a host, a method for modifying expression regulation regions of a gene in the host having the gene encoding the desaturase or the elongase on a genome, or the like.

In the transformant of the present invention, productivity of the long-chain fatty acids or the lipids containing these fatty acids as components is improved in comparison with the host in which the expression of the gene encoding the protein (A) or (B) is not enhanced. Accordingly, if the transformant of the present invention is cultured under suitable conditions and then the long-chain fatty acids or the lipids containing these fatty acids as components are collected from an obtained cultured product or an obtained growth product, the long-chain fatty acids or the lipids containing these fatty acids as components can be efficiently produced. Herein, the term "cultured product" means liquid medium and a transformant subjected to cultivation, and the term "growth product" means a transformant subjected to growth.

The culture condition of the transformant of the present invention can be appropriately selected in accordance with the type of the host, and any ordinary used culture condition for the host can be employed. Further, from a viewpoint of the production efficiency of lipids, precursor substances involved in the fatty acid biosynthesis system, such as glycerol, acetic acid or glucose, may be added to the medium.

For example, in the case of using *Escherichia coli* as the host, culturing *Escherichia coli* may be carried out in LB medium or Overnight Express Instant TB Medium (Novagen) at 30° C. to 37° C. for half a day to 1 day.

In the case of using *Arabidopsis thaliana* as the host, for example, growth of *Arabidopsis thaliana* may be carried out at soil under the temperature conditions of 20° C. to 25° C., by continuously irradiating white light or under light illumination conditions of a light period of 16 hours and a dark period of 8 hours, for one to two months.

In the case of using algae as the host, medium based on natural seawater or artificial seawater may be used. Alternatively, commercially available culture medium may also be used. Specific examples of the culture medium include f/2 medium, ESM medium, Daigo's IMK medium, L1 medium and MNK medium. Above all, from viewpoints of an improvement in the productivity of lipids and a nutritional ingredient concentration, f/2 medium, ESM medium or Daigo's IMK medium is preferred; f/2 medium or Daigo's IMK medium is more preferred; and f/2 medium is further preferred. For growth promotion of the algae and an improvement in productivity of fatty acids, a nitrogen source, a phosphorus source, metal salts, vitamins, trace metals or the like can be appropriately added to the culture medium.

An amount of the transformant to be seeded to the culture medium is appropriately selected. In view of viability, the amount is preferably 1 to 50% (vol/vol), and more preferably 1 to 10% (vol/vol), per culture medium. Culture temperature is not particularly limited within the range in which the temperature does not adversely affect growth of the algae, and is ordinarily in the range of 5 to 40° C. From viewpoints of the growth promotion of the algae, the improvement in productivity of fatty acids, and reduction of production cost, the temperature is preferably 10 to 35° C., and more preferably 15 to 30° C.

Moreover, the algae are preferably cultured under irradiation with light so that photosynthesis can be made. The light irradiation only needs to be made under conditions in which the photosynthesis can be made, and artificial light or sunlight may be applied. From viewpoints of the growth promotion of the algae and the improvement in the productivity of fatty acids, irradiance during the light irradiation is preferably in the range of 100 to 50,000 lx, more preferably in the range of 300 to 10,000 lx, and further preferably 1,000 to 6,000 lx. Moreover, an interval of the light irradiation is not particularly limited. From the viewpoints in a manner similar to the viewpoints described above, the irradiation is preferably performed under a light and dark cycle. In 24 hours, a light period is preferably from 8 to 24 hours, more preferably from 10 to 18 hours, and further preferably 12 hours.

Moreover, the algae are preferably cultured in the presence of a carbon dioxide-containing gas or in a culture medium containing carbonate such as sodium hydrogen carbonate so that the photosynthesis can be made. A concentration of carbon dioxide in the gas is not particularly limited. From viewpoints of the growth promotion and the improvement in the productivity of fatty acids, the concentration is preferably from 0.03 (which is the same degree as the concentration under atmospheric conditions) to 10%, more preferably from 0.05 to 5%, further preferably from 0.1 to 3%, and furthermore preferably from 0.3 to 1%. A concentration of the carbonate is not particularly limited. When the sodium hydrogen carbonate is used, for example, from viewpoints of the growth promotion and the improvement in the productivity of fatty acids, the concentration is preferably from 0.01 to 5% by mass, more preferably from 0.05 to 2% by mass, and further preferably from 0.1 to 1% by mass.

A culture time is not particularly limited, and the culture may be performed for a long time (for example, about 150 days) so that an alga body in which the lipids are accumulated at a high concentration can grow at a high concentration. From viewpoints of the growth promotion of the algae, the improvement in the productivity of fatty acids, and the reduction of production cost, the culture time is preferably from 3 to 90 days, more preferably from 3 to 30 days, and further preferably from 7 to 30 days. The culture may be performed in any of aerated and agitated culture, shaking culture or static culture. From a viewpoint of improving air-permeability, aerated and agitated culture, or shaking culture is preferred, and aerated and agitated culture is more preferred.

A method of collecting the lipids from the cultured product or growth product is appropriately selected from an ordinary method. For example, lipid components can be isolated and collected from the above-described cultured product or growth product by means of filtration, centrifugation, cell disruption, gel filtration chromatography, ion exchange chromatography, chloroform/methanol extraction, hexane extraction, ethanol extraction, or the like. In the case of carrying out the larger scales culturing, lipids can be obtained by collecting oil components from the cultured product or growth product through pressing or extraction, and then performing general purification processes such as degumming, deacidification, decoloration, dewaxing, and deodorization. After lipid components are isolated as such, the isolated lipids are hydrolyzed, and thereby fatty acids can be obtained. Specific examples of the method of isolating fatty acids from lipid components include a method of treating the lipid components at a high temperature of about 70° C. in an alkaline solution, a method of performing a lipase treatment, and a method of degrading the lipid components using high-pressure hot water.

The lipids produced in the production method of the present invention preferably contain fatty acids or fatty acid compounds, and more preferably contain fatty acids or fatty acid ester compounds thereof, in view of usability thereof.

In view of usability for a surfactant or the like, and from a nutritional viewpoint, the fatty acid or the ester compound thereof contained in the lipid is preferably a long-chain fatty acid or an ester compound thereof, more preferably a fatty acid having 18 or more carbon atoms or an ester compound thereof, more preferably a fatty acid having 18 to 22 carbon atoms or an ester compound thereof, more preferably a fatty acid having 18 to 20 carbon atoms or an ester compound thereof, more preferably a fatty acid having 18 or 20 carbon atoms or an ester compound thereof, more preferably an unsaturated fatty acid having 18 or 20 carbon atoms or an ester compound thereof, more preferably a C18:1, C18:2, C18:3, C20:4 or C20:5 fatty acid or an ester compound thereof, more preferably a PUFA having 18 to 20 carbon atoms or an ester compound thereof, more preferably a PUFA having 20 carbon atoms or an ester compound thereof, more preferably a C20:4 or C20:5 fatty acid or an ester compound thereof, and furthermore preferably an EPA or an ester thereof.

From a viewpoint of the productivity, the fatty acid ester compound is preferably a simple lipid or a complex lipid, more preferably a simple lipid, and further preferably a triacylglycerol.

The lipid obtained by the production method of the present invention can be utilized for food, as well as a plasticizer, an emulsifier incorporated into cosmetic products or the like, a cleansing agent such as a soap or a detergent, a fiber treatment agent, a hair conditioning agent, a disinfectant or an antiseptic.

With regard to the embodiments described above, the present invention also discloses methods of producing lipids, methods of improving productivity of lipids, methods of altering composition of fatty acids to be produced, proteins, genes, recombinant vectors, organisms, transformants, and methods of preparing transformants, described below.

<1> A method of producing lipids, containing the steps of:

culturing a transformant in which the expression of a gene encoding the following protein (A) or (B) is enhanced, and producing fatty acids, preferably long-chain fatty acids, more preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, more preferably EPA, or the lipids containing these fatty acids as components, wherein:

protein (A) is a protein consisting of the amino acid sequence set forth in SEQ ID NO: 1; and protein (B) is a protein consisting of an amino acid sequence having 70% or more, preferably 75% or more, more preferably 80% or more, further preferably 85% or more, furthermore preferably 90% or more, furthermore preferably 92% or more, furthermore preferably 95% or more, furthermore preferably 98% or more, and furthermore preferably 99% or more identity with the amino acid sequence of the protein (A), and having KAS activity.

<2> A method of improving lipid productivity, containing the steps of:

enhancing the expression of a gene encoding the protein (A) or (B) in a transformant, and improving the productivity of long-chain fatty acids, preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably 018:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, more preferably EPA, or the lipids containing these fatty acids as components, produced in a cell of the transformant.

<3> A method of modifying the composition of lipids, containing the steps of:

enhancing the gene expression of a gene encoding the protein (A) or (B) in a transformant, and improving the productivity of long-chain fatty acids, preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, more preferably EPA, or the lipids containing these fatty acids as components produced in a cell of the transformant, to modify the composition of fatty acids or lipids in all fatty acids or all lipids to be produced.

<4> A method containing the steps of:

culturing a transformant in which the expression of a gene encoding the protein (A) or (B) is enhanced, and improving the ratio of the amount of long-chain fatty acids (preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, and more preferably EPA) or the amount of ester compounds thereof, in the total amount of all fatty acids, or the total amount of fatty acid esters consisting of the ester compounds thereof.

<5> The method described in any one of the above items <1> to <4>, containing the steps of introducing the gene encoding the protein (A) or (B) into a host, and enhancing the expression of the gene.

<6> A method of producing lipids, containing the steps of:

culturing a transformant into which a gene encoding the protein (A) or (B) is introduced, and producing fatty acids, preferably long-chain fatty acids, more preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, more preferably EPA, or the lipids containing these fatty acids as components <7> A method of enhancing productivity of lipids, containing the steps of:

introducing a gene encoding the proteins (A) or (B) into a host, and thereby preparing a transformant, and improving productivity of long-chain fatty acids, more preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, more preferably EPA, or the lipids containing these fatty acids as components produced in a cell of the transformant.

<8> A method of modifying the composition of lipids, containing the steps of:

introducing a gene encoding the proteins (A) or (B) into a host, and thereby preparing a transformant, and enhancing productivity of long-chain fatty acids, more preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C18:2, C18:3, C20:4, or C20:5 fatty acids, more preferably PUFA having 18 or 20 carbon atoms, more preferably PUFA having 20 carbon atoms, more preferably C20:4 or C20:5 fatty acids, more preferably EPA, or the lipids containing these fatty acids as components produced in a cell of the transformant, to modify the composition of fatty acids or lipids in all fatty acids or all lipids to be produced.

<9> A method containing the steps of:

culturing a transformant into which a gene encoding the protein (A) or (B) is introduced, and enhancing the ratio of the amount of long-chain fatty acids (preferably fatty acids having 18 or more carbon atoms, more preferably fatty acids having 18 to 22 carbon atoms, more preferably fatty acids having 18 to 20 carbon atoms, more preferably fatty acids having 18 or 20 carbon atoms, more preferably unsaturated fatty acids having 18 or 20 carbon atoms, more preferably C18:1, C182, C18:3, C20:4, or C20:5 fatty acids, more preferably PUFA having 18 or 20 carbon atoms, more preferably PUFA having 20 carbon atoms, more preferably C20:4 or C20:5 fatty acids, and more preferably EPA) and the amount of ester compounds thereof, in the total amount of all fatty acids, or the total amount of fatty acid esters consisting of the ester compounds thereof.

<10> The method described in any one of the above items <1> to <9>, wherein the protein (B) consists of an amino acid sequence in which 1 or several amino acids, preferably 1 or more and 142 or less amino acids, more preferably 1 or more and 118 or less amino acids, further preferably 1 or more and 95 or less amino acids, furthermore preferably 1 or more and 71 or less amino acids, furthermore preferably 1 or more and 47 or less amino acids, furthermore preferably 1 or more and 38 or less amino acids, furthermore preferably 1 or more and 23 or less amino acids, furthermore preferably 1 or more and 9 or less amino acids, and furthermore preferably 1 or more and 4 or less amino acids, are deleted, substituted, inserted or added to the amino acid sequence of the protein (A).

<11> The method described in any one of the above items <1> to <10>, wherein the identity of the protein (B) with the amino acid sequence of the protein (A) is 92% or more, and the protein (B) has KAS activity.

<12> The method described in any one of the above items <1> to <11>, wherein a gene encoding the protein (A) or (B) is a gene consisting of the following DNA (a) or (b), wherein:

DNA (a) is a DNA consisting of the nucleotide sequence set forth in SEQ ID NO: 2; and DNA (b) is a DNA consisting of a nucleotide sequence having 70% or more, preferably 75% or more, more preferably 80% or more, further preferably 85% or more, furthermore preferably 90% or more, furthermore preferably 92% or more, furthermore preferably 95% or more, furthermore preferably 98% or more, and furthermore preferably 99% or more, identity with the nucleotide sequence of the DNA (a), and encoding the protein (A) or (B) having KAS activity.

<13> The method described in any one of the above items <1> to <12>, wherein the DNA (b) is a DNA consisting of a nucleotide sequence in which 1 or several nucleotides, preferably 1 or more and 428 or less nucleotides, more preferably 1 or more and 357 or less nucleotides, further preferably 1 or more and 285 or less nucleotides, furthermore preferably 1 or more and 214 or less nucleotides, furthermore preferably 1 or more and 142 or less nucleotides, furthermore preferably 1 or more and 114 or less nucleotides, furthermore preferably 1 or more and 71 or less nucleotides, furthermore preferably 1 or more and 28 or less nucleotides, and furthermore preferably 1 or more and 14 or less nucleotides, are deleted, substituted, inserted or added to the nucleotide sequence of the DNA (a), and encoding the protein (A) or (B) having KAS activity, or a DNA capable of hybridizing with a DNA consisting of a nucleotide sequence complementary with the DNA (a) under a stringent condition, and encoding the protein (A) or (B) having KAS activity.

<14> The method described in any one of the above items <1> to <13>, wherein the protein (A) or (B) is a KAS having the synthetic activity of long-chain β-ketoacyl-ACP.

<15> The method described in any one of the above items <1> to <14>, wherein expression of a gene encoding a TE is enhanced in the transformant.

<16> The method described in any one of the above items <1> to <15>, wherein expression of a gene encoding a desaturase is enhanced in the transformant.

<17> The method described in any one of the above items <1> to <16>, wherein the gene encoding a desaturase is introduced into the transformant.

<18> The method described in the above item <16> or <17>, wherein the desaturase is at least one of the desaturase selected from the group consisting of Δ12-DES, Δ6-DES, ω3-DES, Δ5-DES, and Δ9-DES.

<19> The method described in the above item <18>, wherein the Δ12-DES is a protein consisting of the amino acid sequence set forth SEQ ID NO: 32 or 34, or a protein having the identity of 60% or more, preferably 70% or more, more preferably 80% or more, or more preferably 90% or more, with a protein consisting of the amino acid sequence set forth SEQ ID NO: 32 or 34, and having the Δ12-DES activity.

<20> The method described in the above item <18> or <19>, wherein the gene encoding the Δ12-DES is a gene consisting of a DNA of the nucleotide sequence set forth SEQ ID NO: 33 or 35, or a gene having the identity of 60% or more, preferably 70% or more, more preferably 80% or more, or more preferably 90% or more, with a gene consisting of the nucleotide sequence set forth SEQ ID NO: 33 or 35, and encoding the protein having the Δ12-DES activity.

<21> The method described in any one of the above items <18> to <20>, wherein the Δ6-DES is a protein consisting of the amino acid sequence set forth SEQ ID NO: 36 or 38, or a protein having the identity of 60% or more, preferably 70% or more, more preferably 80% or more, or more preferably 90% or more, with a protein consisting of the amino acid sequence set forth SEQ ID NO: 36 or 38, and having the Δ6-DES activity.

<22> The method described in any one of the above items <18> to <21>, wherein the gene encoding the Δ6-DES is a gene consisting of a DNA of the nucleotide sequence set forth SEQ ID NO: 37 or 39, or a gene having the identity of 60% or more, preferably 70% or more, more preferably 80% or more, or more preferably 90% or more, with a gene consisting of the nucleotide sequence set forth SEQ ID NO: 37 or 39, and encoding the protein having the Δ6-DES activity.

<23> The method described in any one of the above items <18> to <22>, wherein the ω3-DES is a protein consisting of the amino acid sequence set forth SEQ ID NO: 40 or 42, or a protein having the identity of 60% or more, preferably 70% or more, more preferably 80% or more, or more preferably 90% or more, with a protein consisting of the amino acid sequence set forth SEQ ID NO: 40 or 42, and having the ω3-DES activity.

<24> The method described in any one of the above items <18> to <23>, wherein the gene encoding the ω3-DES is a gene consisting of a DNA of the nucleotide sequence set forth SEQ ID NO: 41 or 43, or a gene having the identity of 60% or more, preferably 70% or more, more preferably 80% or more, or more preferably 90% or more, with a gene consisting of the nucleotide sequence set forth SEQ ID NO: 41 or 43, and encoding the protein having the ω3-DES activity.

<25> The method described in any one of the above items <18> to <24>, wherein the Δ5-DES is a protein consisting of the amino acid sequence set forth SEQ ID NO: 44 or 46, or a protein having the identity of 60% or more, preferably 70% or more, more preferably 80% or more, or more preferably 90% or more, with a protein consisting of the amino acid sequence set forth SEQ ID NO: 44 or 46, and having the Δ5-DES activity.

<26> The method described in any one of the above items <18> to <25>, wherein the gene encoding the Δ5-DES is a gene consisting of a DNA of the nucleotide sequence set forth SEQ ID NO: 45 or 47, or a gene having the identity of 60% or more, preferably 70% or more, more preferably 80% or more, or more preferably 90% or more, with a gene consisting of the nucleotide sequence set forth SEQ ID NO: 45 or 47, and encoding the protein having the Δ5-DES activity.

<27> The method described in any one of the above items <18> to <26>, wherein the Δ9-DES is a protein consisting of the amino acid sequence set forth SEQ ID NO: 48 or 50, or a protein having the identity of 60% or more, preferably 70% or more, more preferably 80% or more, or more preferably 90% or more, with a protein consisting of the amino acid sequence set forth SEQ ID NO: 48 or 50, and having the Δ9-DES activity.

<28> The method described in any one of the above items <18> to <27>, wherein the gene encoding the Δ9-DES is a gene consisting of a DNA of the nucleotide sequence set forth SEQ ID NO: 49 or 51, or a gene having the identity of 60% or more, preferably 70% or more, more preferably 80% or more, or more preferably 90% or more, with a gene consisting of the nucleotide sequence set forth SEQ ID NO: 49 or 51, and encoding the protein having the Δ9-DES activity.

<29> The method described in any one of the above items <1> to <28>, wherein expression of a gene encoding an elongase is enhanced in the transformant.

<30> The method described in any one of the above items <1> to <29>, wherein the transformant is a microorganism or a plant.

<31> The method described in the above item <30>, wherein the microorganism is a microalga, preferably an alga belonging to the genus *Nannochloropsis*, more preferably *Nannochloropsis oculata.*

<32> The method described in the above item <30>, wherein the microorganism is *Escherichia coli.*

<33> The method described in the above item <30>, wherein the plant is *Arabidopsis thaliana.*

<34> The method described in any one of the above items <1> to <33>, wherein the lipids contain a long-chain fatty acid or an ester compound thereof, preferably a fatty acid having 18 or more carbon atoms or an ester compound thereof, more preferably a fatty acid having 18 to 22 carbon atoms or an ester compound thereof, more preferably a fatty acid having 18 to 20 carbon atoms or an ester compound thereof, more preferably a fatty acid having 18 or 20 carbon atoms or an ester compound thereof, more preferably an unsaturated fatty acid having 18 or 20 carbon atoms or an ester compound thereof, more preferably a C18:1, C18:2, C18:3, C20:4 or C20:5 fatty acid or an ester compound thereof, more preferably a PUFA having 18 or 20 carbon atoms or an ester compound thereof, more preferably a PUFA having 20 carbon atoms or an ester compound thereof, more preferably a C20:4 or C20:5 fatty acid or an ester compound thereof, furthermore preferably an EPA or an ester compound thereof.

<35> The method described in any one of the above items <1> to <34>, wherein the long-chain fatty acid is a long-chain polyunsaturated fatty acid <36> The protein (A) or (B) specified in any one of the above items <1> to <35>.

<37> A gene encoding the protein described in the above item <36>

<38> A gene consisting of the DNA (a) or (b) specified in any one of the above items <1> to <35>.

<39> A recombinant vector, containing the gene described in the above item <37> or <38>.

<40> A transformant, wherein the expression of the gene described in the above item <37> or <38> is enhanced.

<41> The transformant described in the above item <40>, wherein the productivity of long-chain fatty acids or lipids containing these fatty acids as components is improved, in comparison with that in a host.

<42> A transformant, which is obtained by introducing the gene described in the above item <37> or <38> or the recombinant vector described in the above item <39> into a host.

<43> A method of producing a transformant, containing introducing the gene described in the above item <37> or <38> or the recombinant vector described in the above item <39> into a host.

<44> The transformant or the method of producing the same described in any one of the above items <40> to <43>, wherein expression of a gene encoding a TE is enhanced.

<45> The transformant or the method of producing the same described in any one of the above items <40> to <44>, wherein expression of a gene encoding a desaturase is enhanced.

<46> The transformant or the method of producing the same described in any one of the above items <40> to <45>, wherein the gene encoding a desaturase is introduced into a transformant.

<47> The transformant or the method of producing the same described in the above item <45> or <46>, wherein the desaturase is at least one of the desaturase selected from the group consisting of Δ12-DES, Δ6-DES, ω3-DES, Δ5-DES, and Δ9-DES.

<48> The transformant or the method of producing the same described in any one of the above items <45> to <47>, wherein the desaturase or the gene encoding a desaturase is a desaturase or a gene encoding a desaturase specified in any one of the above items <19> to <28>.

<49> The transformant or the method of producing the same described in any one of the above items <40> to <48>, wherein expression of a gene encoding an elongase is enhanced.

<50> The transformant or the method of producing the same described in any one of the above items <40> to <49>, wherein the transformant or the host is a microorganism or a plant.

<51> The transformant or the method of producing the same described in the above item <50>, wherein the microorganism is a microalga, preferably an alga belonging to the genus *Nannochloropsis*, and more preferably *Nannochloropsis oculata.*

<52> The transformant or the method of producing the same described in the above item <50>, wherein the microorganism is *Escherichia coli*.

<53> The transformant or the method of producing the same described in the above item <50>, wherein the plant is *Arabidopsis thaliana*.

<54> Use of the protein, the gene, the recombinant vector, the transformant or a transformant obtained by the method of producing a transformant described in any one of the above items <36> to <53>, for producing lipids.

<55> The use described in the above item <54>, wherein the lipids contain a long-chain fatty acid or an ester compound thereof, preferably a fatty acid having 18 or more carbon atoms or an ester compound thereof, more preferably a fatty acid having 18 to 22 carbon atoms or an ester compound thereof, further preferably a fatty acid having 18 to 20 carbon atoms or an ester compound thereof, furthermore preferably a fatty acid having 18 or 20 carbon atoms or an ester compound thereof, furthermore preferably an unsaturated fatty acid having 18 or 20 carbon atoms or an ester compound thereof, furthermore preferably a C18:1, C18:2, C18:3, C20:4, or C20:5 fatty acid or an ester compound thereof, furthermore preferably a PUFA having 18 or 20 carbon atoms or an ester compound thereof, furthermore preferably a PUFA having 20 carbon atoms or an ester compound thereof, furthermore preferably a C20:4 or C20:5 fatty acid or an ester compound thereof, still furthermore preferably a EPA or an ester compound thereof.

<56> The use described in the above item <55>, wherein the long-chain fatty acid is a long-chain polyunsaturated fatty acid.

EXAMPLES

Hereinafter, the present invention will be described more in detail with reference to Examples, but the present invention is not limited thereto. Herein, the nucleotide sequences of the primers used in Examples are shown in Table 1.

TABLE 1

| Primer No. | Nucleotide sequence (5'→3') | SEQ ID NO: |
|---|---|---|
| 8 | CTTTTTTGTGAAGCAATGGCCAAGTTGACCAGTGCCG | SEQ ID NO: 8 |
| 9 | TTTCCCCCATCCCGATTAGTCCTGCTCCTCGGCCAC | SEQ ID NO: 9 |
| 10 | CGAGCTCGGTACCCGACTGCGCATGGATTGACCGA | SEQ ID NO: 10 |
| 11 | TGCTTCACAAAAAAGACAGCTTCTTGAT | SEQ ID NO: 11 |
| 12 | TCGGGATGGGGGAAAAAAACCTCTG | SEQ ID NO: 12 |
| 13 | ACTCTAGAGGATCCCCTTTCGTAAATAAATCAGCTC | SEQ ID NO: 13 |
| 14 | GGGATCCTCTAGAGTCGACC | SEQ ID NO: 14 |
| 15 | CGGGTACCGAGCTCGAATTC | SEQ ID NO: 15 |
| 16 | CAGCCCGCATCAACAATGATGGAGAAGCTGACCCTC | SEQ ID NO: 16 |
| 17 | CTCTTCCACAGAAGCCTAGGCAACATACTTCTTGAAG | SEQ ID NO: 17 |
| 18 | CGAGCTCGGTACCCGTTCTTCCGCTTGTTGCTGCC | SEQ ID NO: 18 |
| 19 | TGTTGATGCGGGCTGAGATTGGTGG | SEQ ID NO: 19 |
| 20 | GCTTCTGTGGAAGAGCCAGTG | SEQ ID NO: 20 |
| 21 | GGCAAGAAAAGCTGGGGGAAAAGACAGG | SEQ ID NO: 21 |
| 22 | CCAGCTTTTCTTGCCACTGCGCATGGATTGACCGA | SEQ ID NO: 22 |
| 52 | CAGCCCGCATCAACAATGGGACGCGGCGGTGAGAA | SEQ ID NO: 52 |
| 53 | CTCTTCCACAGAAGCCTATGCCCGCTGCTTGTAGA | SEQ ID NO: 53 |
| 54 | CAGCCCGCATCAACAATGGTTGAGCAAACGTTACC | SEQ ID NO: 54 |
| 55 | CTCTTCCACAGAAGCTTACGGAGGGGAGGATGAAC | SEQ ID NO: 55 |
| 57 | CTTTTTTGTGAAGCAATGGTCGAGATTCGAAGCAT | SEQ ID NO: 57 |
| 58 | TTTCCCCCATCCCGATCAGAAGAACTCGTCCAACA | SEQ ID NO: 58 |
| 59 | TGCTTCACAAAAAAGACAGCTTCTTGAT | SEQ ID NO: 59 |
| 60 | TCGGGATGGGGGAAAAAAACCTCTG | SEQ ID NO: 60 |

Example 1 Preparation of a Transformant in which a NoKASII Gene is Introduced into *Nannochloropsis oculata* and Production of Fatty Acids by the Transformant (1) Construction of Plasmid for Zeocin Resistance Gene Expression A zeocin resistance gene (SEQ ID NO: 3), and a tubulin promoter sequence (SEQ ID NO: 4) derived from *Nannochloropsis qaditana* strain CCMP 526 described in a literature (Randor Radakovits, et al., Nature Communications, DOI:10.1038/ncomms1688, 2012) were artificially synthesized.

Using the thus-synthesized DNA fragments as a template, and a pair of the primer Nos. 8 and 9, and a pair of the primer Nos. 10 and 11 shown in Table 1, PCR were carried out, to amplify the zeocin resistance gene and the tubulin promoter sequence, respectively.

Further, using a genome of *Nannochloropsis oculata* strain NIES-2145 as a template, and a pair of the primer Nos. 12 and 13 shown in Table 1, PCR was carried out to amplify the heat shock protein terminator sequence (SEQ ID NO: 5).

Furthermore, using a plasmid vector pUC19 (manufactured by Takara Bio) as a template, and a pair of the primer Nos. 14 and 15 shown in Table 1, PCR was carried out to amplify the plasmid vector pUC19.

These four amplified fragments were treated by restriction enzyme Dpnl (manufactured by TOYOBO) respectively, and were purified using a High Pure PCR Product Purification Kit (manufactured by Roche Applied Science). Then, obtained four fragments were fused using an In-Fusion HD Cloning Kit (manufactured by Clontech) to construct a plasmid for zeocin resistance gene expression.

Herein, the expression plasmid consisted of the pUC19 vector sequence and an insert sequence in which the tubulin promoter sequence, the zeocin resistance gene and the heat shock protein terminator sequence were linked in this order.

(2) Obtaining of NoKASII Gene, and Construction of Plasmid for NoKASII Gene Expression Total RNA of *Nannochloropsis oculata* strain NIES-2145 (obtained from National Institute for Environmental Studies (NIES)) was extracted. The cDNA was obtained by reverse transcription using the total RNA, and SuperScript (trademark) Ill First-Strand Synthesis SuperMix for qRT-PCR (manufactured by invitrogen). PCR using a pair of the primer Nos. 16 and 17 shown in Table 1 and the above cDNA as a template, was carried out to prepare a gene fragment consisting of the nucleotide sequence set forth in SEQ ID NO: 2

Further, using a genome of *Nannochloropsis oculata* strain NIES-2145 as a template, and a pair of the primer Nos. 18 and 19, and a pair of the primer Nos. 20 and 21 shown in Table 1, respectively, PCR were carried out to prepare the LDSP promoter sequence (SEQ ID NO: 6), and the VCP1 (violaxanthin/(chlorophyll a)-binding protein 1) terminator sequence (SEQ ID NO: 7).

Furthermore, using the above-described plasmid for zeocin resistance gene expression as a template, and a pair of the primer Nos. 22 and 15 shown in Table 1, PCR was carried out to amplify a fragment containing the cassette for zeocin resistance gene expression (the tubulin promoter sequence, the zeocin resistance gene, and the heat shock protein terminator sequence) and the pUC19 vector sequence.

These four fragments were fused by a method in a manner similar to described above, to construct plasmids for NoKASII gene expression.

Herein, the expression plasmid consisted of the pUC19 vector sequence and an insert sequence in which the LDSP promoter sequence, the NoKASII gene, the VCP1 terminator sequence, the tubulin promoter sequence, the zeocin resistance gene and the heat shock protein terminator sequence were linked in this order.

(3) Introduction of a Cassette for NoKASII Gene Expression into *Nannochloropsis*

Using the above-described plasmid for the NoKASII gene expression as a template, and a pair of the primer Nos. 13 and 18 shown in Table 1, PCR was carried out to amplify the cassette for NoKASII gene expression (a DNA fragment containing the LDSP promoter sequence, the NoKASII gene, the VCP1 terminator sequence, the tubulin promoter sequence, the zeocin resistance gene, and the heat shock protein terminator sequence).

The amplified DNA fragment was purified using High Pure PCR Product Purification Kit (manufactured by Roche Applied Science). Herein, sterilized water was used for elution upon purification without using an elution buffer included in the kit.

About $1\times10^9$ cells of *Nannochloropsis oculata* strain NIES-2145 (obtained from National Institute for Environmental Studies (NIES)) were washed with 384 mM sorbitol solution to completely remove a salt, and the resultant was used as a host cell for transformation. The cassette for NoKASII gene expression as amplified above was mixed by about 500 ng with the host cell, and electroporation was carried out under the conditions of 50 μF, 500Ω and 2,200 v/2 mm.

After one day recovery cultivation in f/2 liquid medium (75 mg of $NaNO_3$, 6 mg of $NaH_2PO_4.2H_2O$, 0.5 μg of vitamin B12, 0.5 μg of biotin, 100 μg of thiamine, 10 mg of $Na_2SiO_3.9H_2O$, 4.4 mg of $Na_2EDTA.2H_2O$, 3.16 mg of $FeCl_3.6H_2O$, 12 μg of $FeCl_3.6H_2O$, 21 μg of $ZnSO_4.7H_2O$, 180 μg of $MnCl_2.4H_2O$, 7 μg of $CuSO_4.5H_2O$, 7 μg of $Na_2MoO_4.2H_2O$/artificial sea water 1 L), the resultant was inoculated in f/2 agar medium containing 2 μg/mL of zeocin, and cultured for three weeks under 12 h/12 h light-dark conditions at 25° C. under an atmosphere of 0.3% $CO_2$. A transformant of *Nannochloropsis oculata* strain containing the cassette for NoKASII gene expression was selected from the resultant colonies by a PCR method (obtaining two lines independently).

(4) Culturing of the Transformant, Extraction of Lipid from Culture Fluid and Analysis of Fatty Acids Contained Therein The selected strain was inoculated to 20 mL of medium in which a nitrogen concentration in the f/2 medium was reinforced 15 times, and a phosphorus concentration therein was reinforced 5 times (hereinafter, referred to as "N15P5 medium"), and subjected to shaking culture for four weeks under the 12 h/12 h light-dark conditions at 25° C. under the atmosphere of 0.3% $CO_2$, to prepare preculture fluid. Then, 2 mL of the preculture fluid was inoculated to 18 mL of the N15P5 medium, and subjected to shaking culture for three weeks under the 12 h/12 h light-dark conditions at 25° C. under the atmosphere of 0.3% $CO_2$. In addition, as a negative control, an experiment was also conducted on the wild type strain, *Nannochloropsis oculata* strain NIES-2145.

To 1 mL of the culture fluid, 50 μL of 1 mg/mL 7-pentadecanone as an internal standard was added, and then 0.5 mL of chloroform and 1 mL of methanol were further added. The mixture was vigorously stirred and then was left for 10 minutes. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette.

A nitrogen gas was blown onto the resultant chloroform layer to be dried into solid. Then, 1 mL of 14% boron trifluoride-methanol solution (manufactured by Sigma-Aldrich) was added to the sample, and the mixture was kept warm at 80° C. for 30 minutes. Thereafter, 0.5 mL of hexane and 1 mL of saturated saline were added thereto, and the mixture was vigorously stirred and then was left for 10 minutes at room temperature. Then, the hexane layer (upper layer) was collected to obtain fatty acid methyl esters.

Under the measuring conditions as follows, the obtained fatty acid methyl esters were provided for gas chromatographic analysis.

<Gas Chromatography Conditions>

Analysis apparatus: 7890A (manufactured by Agilent Technologies)

Capillary column: DB-WAX (10 m×100 μm×0.10 μm, manufactured by J&W Scientific)

Mobile phase: high purity helium

Oven temperature: maintained for 0.5 minutes at 100° C.→100 to 250° C. (temperature increase at 20° C./minute) →maintained for 3 minutes at 250° C. (post run: 1 minute)

Injection port temperature: 300° C.

Injection method: split injection (split ratio: 50:1)

Amount of injection: 5 μL

Cleaning vial: methanol

Detection method: FID

Detector temperature: 350° C.

Moreover, the fatty acid methyl esters were identified by providing the identical sample for gas chromatography-mass spectrometry analysis under identical conditions described above.

Amounts of the fatty acid methyl esters of each of the fatty acids were quantitatively determined based on the peak areas of waveform data obtained by the above gas chromatographic analysis. The peak area corresponding to each of the fatty acid methyl esters was compared with that of 7-pentadecanone as the internal standard, and carried out corrections between the samples, and then the amount of each of the fatty acids per liter of the culture fluid was calculated. Further, the total amount of the fatty acids was calculated by summing the amounts of each of the fatty acids thus obtained, and ratio of each of the fatty acids in the total amount of the fatty acids was calculated.

Table 2 shows the results (ratio of amounts of each of the fatty acids, and yield of C20:5 fatty acids). Herein, in Table below, "Fatty Acid Composition (% TFA)" presents a ratio of a weight of each fatty acid relative to a weight of the total fatty acid (weight percent).

Further, from the results of yield of C20:5, productivity of EPA was improved in both strains of NoKASII_line 1 and NoKASII_line 2, in comparison with the wild type strain.

(5) Fractionation of TAG and Analysis of Fatty Acids Contained in TAG

To 1 mL of the culture fluid, 0.5 mL of chloroform and 1 mL of methanol were added. The mixture was vigorously stirred and then was left for 10 minutes or more. Further, 0.5 mL of chloroform and 0.5 mL of 1.5% KCl were added thereto. The mixture was stirred and centrifuged for 5 minutes at 3,000 rpm, and then the chloroform layer (lower layer) was collected with Pasteur pipette. A nitrogen gas was blown onto the resultant chloroform layer to be dried into solid, and the resultant material was dissolved into 20 μL of chloroform.

A total amount of the thus obtained lipids extract, and 3 μL of three kinds of standard solutions {trimyristin (manufactured by Wako Pure Chemical Industries, Ltd.), glycerol dioleate (manufactured by Wako Pure Chemical Industries, Ltd.), oleic acid (manufactured by Wako Pure Chemical Industries, Ltd.), and 10 mg/mL chloroform solution} each were spotted onto TLC silica gel $60F_{254}$ (manufactured by Merck), and the resultant material was developed for about 15 minutes by using TLC developing tank DT-150 (manufactured by Mitsubishi Chemical Medience Corporation) with a developing solvent (hexane:diethyl ether:formic acid=42:28:0.3 (volume ratio)). After development, the plate was dried, 0.1% primulin (manufactured by Wako Pure Chemical Industries, Ltd.) dissolved in methanol was sprayed thereon and dried, and then a TAG fraction was detected by handy type UV lamp UVL-21 (manufactured by SOGO LABORATORY GLASS WORKS CO., LTD.).

The TAG fraction was scratched and collected by using a toothpick and 1 mL of 14% boron trifluoride-methanol solution (manufactured by Sigma-Aldrich) was added thereto, and a temperature of the resultant material was kept

TABLE 2

| | Fatty acid composition (% TFA) | | | | | | | | |
|---|---|---|---|---|---|---|---|---|---|
| | C12:0 | C14:0 | C16:0 | C16:1 | C18:0 | C18:1 | C18:2 | C18:3 | C18:4 |
| NIES-2145 | 0.3 | 5.0 | 32.0 | 28.6 | 1.5 | 13.7 | 1.4 | 0.4 | 0.3 |
| NoKASII_line 1 | 0.1 | 0.5 | 19.2 | 19.7 | 1.5 | 19.6 | 4.0 | 1.5 | 0.4 |
| NoKASII_line 2 | 0.1 | 0.5 | 17.8 | 19.9 | 1.5 | 18.3 | 4.5 | 1.7 | 0.4 |

| | Fatty acid composition (% TFA) | | | | | Yield of C20:5 |
|---|---|---|---|---|---|---|
| | C20:0 | C20:1 | C20:3 | C20:4 | C20:5 | (mg/L) |
| NIES-2145 | 0.1 | 0.0 | 0.4 | 2.7 | 13.6 | 123.2 |
| NoKASII_line 1 | 0.2 | 0.5 | 0.7 | 6.9 | 25.2 | 172.0 |
| NoKASII_line 2 | 0.2 | 0.9 | 0.8 | 9.6 | 23.9 | 162.0 |

As is apparent from Table 2, with regard to both of two strains of transformants (NoKASII_line 1 and NoKASII_line 2) prepared by introducing the cassette for NoKASII gene expression to forcibly express the NoKASII gene, the ratios of long-chain fatty acids (C18 fatty acids and C20 fatty acids) to the total amount of the total fatty acids produced significantly increased in comparison with the wild type strain (NIES-2145). In particular, the ratios of C18:1, C18:2, C18:3, C20:4 and C20:5 (EPA) fatty acids were much further increased.

constant at 80° C. for 30 minutes. Then, 0.5 mL of hexane and 1 mL of saturated saline were added thereto, and the resultant mixture was vigorously stirred and left to stand for 10 minutes at room temperature, and then, the hexane layer being an upper layer was collected to obtain fatty acid methyl esters.

The obtained fatty acid methyl esters were provided for gas chromatographic analysis by a method in a manner similar to described above. Table 3 shows the results as fatty acid compositions.

TABLE 3

| | Fatty acid composition (% TFA) | | | | | | | | |
|---|---|---|---|---|---|---|---|---|---|
| | C12:0 | C14:0 | C16:0 | C16:1 | C18:0 | C18:1 | C18:2 | C18:3 | C18:4 |
| NIES-2145 | 0.3 | 3.8 | 36.1 | 30.8 | 2.9 | 18.9 | 1.2 | 0.4 | 0.1 |
| NoKASII_line 1 | 0.2 | 0.3 | 17.9 | 20.1 | 3.0 | 25.5 | 4.0 | 1.4 | 0.3 |
| NoKASII_line 2 | 0.2 | 0.4 | 16.9 | 21.8 | 2.2 | 27.6 | 4.6 | 1.4 | 0.4 |

| | Fatty acid composition (% TFA) | | | | |
|---|---|---|---|---|---|
| | C20:0 | C20:1 | C20:3 | C20:4 | C20:5 |
| NIES-2145 | 0.2 | 0.0 | 0.5 | 0.9 | 3.9 |
| NoKASII_line 1 | 0.2 | 0.6 | 1.0 | 5.8 | 19.5 |
| NoKASII_line 2 | 0.2 | 1.3 | 1.1 | 7.4 | 14.4 |

As is apparent from Table 3, with regard to both of two strains of transformants (NoKASII_line 1 and NoKASII_line 2) prepared by introducing the cassette for NoKASII gene expression to forcibly express the NoKASII gene, the ratios of long-chain fatty acids (C18 fatty acids and C20 fatty acids) in TAG significantly increased in comparison with the wild type strain (NIES-2145). In particular, the ratios of C18:1, C18:2, C18:3, C20:4 and C20:5 (EPA) fatty acids were much further increased. Above all, an increase in the ratios of PUFA of C20:4, C20:5 fatty acids and the like was marked.

Furthermore, in *Nannochloropsis oculata* EPA is produced during a growth period, but not produced during a fats and oils accumulation period. Thus, only about 4% of EPA is known to exist in TAG being accumulated fats. In contrast, a large amount of EPA was incorporated also into TAG in the transformants in which the NoKASII gene was forcibly expressed, and the ratio of EPA reached 19.5% at a maximum.

Example 2 Preparation of a Transformant in which a NoKASII Gene and a Desaturase Gene are Introduced into *Nannochloropsis oculata* and Production of Fatty Acids by the Transformant (1) Obtaining of a Desaturase Gene and Construction of Plasmid for Desaturase Gene Expression (with the Zeocin Resistance Gene)

Using the cDNA of *Nannochloropsis oculata* strain NIES-2145 obtained from Example 1 as a template, and a pair of the primer Nos. 52 and 53, and a pair of the primer Nos. 54 and 55 shown in Table 1, respectively, PCR were carried out to prepare the gene fragments consisting of the nucleotide sequence set forth in SEQ ID NO: 33, and the gene fragments consisting of the nucleotide sequence set forth in SEQ ID NO: 41.

A plasmid for NoΔ12-DES gene expression and a plasmid for Noω3-DES gene expression were constructed, respectively, by fusing the amplified fragments with an LDSP promoter sequence, a VCP1 terminator sequence and a cassette for zeocin resistance gene expression, according to the same method as in Example 1. Herein, these expression plasmids consisted of the pUC19 vector sequence and an insert sequence in which the LDSP promoter sequence, each desaturase gene, the VCP1 terminator sequence, the tubulin promoter sequence, the zeocin resistance gene and the heat shock protein terminator sequence were linked in this order.

(2) Construction of Plasmid for Desaturase Gene Expression (with Paromomycin Resistance Gene)

Paromomycin resistance gene fragment was amplified by carrying out PCR by using the paromomycin resistance gene (SEQ ID NO: 56) artificially synthesized as a template, and a pair of the primer Nos. 57 and 58 shown in Table 1.

Further, PCR using a pair of the primer Nos. 59 and 60 shown in Table 4 was carried out by using the above-described plasmid for NoΔ12-DES gene expression and plasmid for Noω3-DES gene expression as a template, respectively. A plasmid for NoΔ12-DES gene expression (paromomycin resistance) and a plasmid for Noω3-DES gene expression (paromomycin resistance) were constructed, respectively, by fusing the amplified fragments with a paromomycin resistance gene fragments. Herein, these expression plasmids consisted of the pUC19 vector sequence and an insert sequence in which the LDSP promoter sequence, each desaturase genes, the VCP1 terminator sequence, the tubulin promoter sequence, the paromomycin resistance gene and the heat shock protein terminator sequence were linked in this order.

(3) Introduction of Plasmid for Desaturase Gene Expression (Paromomycin Resistance) into NoKASII Transgenic Strain PCR using a pair of the primer Nos. 13 and 18 shown in Table 1 was carried out by using the above-described plasmid for NoΔ12-DES gene expression (paromomycin resistance) and plasmid for Noω3-DES gene expression (paromomycin resistance) as a template, respectively, to amplify a cassette for desaturase gene expression (the DNA fragments containing the LDSP promoter sequence, each desaturase gene, the VCP1 terminator sequence, the tubulin promoter sequence, the paromomycin resistance gene and the heat shock protein terminator sequence).

The amplified DNA fragments were purified, respectively, according to the same method as in Example 1, and the purified DNA fragments were introduced into the transformant NoKASII_line 2 (hereinafter, also referred to as "NoKASII transgenic strain") by electroporation, respectively.

Recovery cultivation was carried out according to the same method as in Example 1, and then the resultant was applied onto an f/2 agar medium containing 2 μg/mL of zeocin and 100 μg/mL of paromomycin, and cultured for two to three weeks under 12 h/12 h light-dark conditions at 25° C. under an atmosphere of 0.3% $CO_2$. *Nannochloropsis oculata* strains containing each cassette for desaturase gene expression were selected from obtained colonies.

(4) Culture of Transformant, Extraction of Lipids and Analysis of Fatty Acids Contained Therein The selected strain was inoculated to 20 mL of the N15P5 medium, and subjected to shaking culture for three to four weeks under the 12 h/12 h light-dark conditions at 25° C. under the atmosphere of 0.3% $CO_2$, to prepare preculture fluid. Then, 2 mL of the preculture fluid was inoculated to 18 mL of medium in which a nitrogen concentration in the f/2 medium was reinforced 5 times, and a phosphorus concentration therein was reinforced 5 times (hereinafter, referred to as "N5P5 medium"), and subjected to shaking culture for ten days under the 12 h/12 h light-dark conditions at 25° C.

under the atmosphere of 0.3% $CO_2$. In addition, as a negative control, the wild type strain and the strain transformed with the NoKASII gene were also subjected to the same experiment.

Extraction of lipids from obtained culture liquids and analysis of fatty acids contained therein were carried out, according to the same method as in Example 1. Table 4 shows the results.

TABLE 4

| | Fatty acid composition (% TFA) | | | | | | | | | | Yield of C20:5 |
|---|---|---|---|---|---|---|---|---|---|---|---|
| | C14:0 | C16:0 | C16:1 | C18:0 | C18:1 | C18:2 | C18:3 | C20:3 | C20:4 | C20:5 | (mg/L) |
| NIES-2145 | 5.1 | 43.0 | 28.2 | 1.5 | 10.3 | 1.1 | 0.0 | 0.0 | 2.0 | 8.8 | 76.9 |
| NoKASII | 2.0 | 38.7 | 26.8 | 1.5 | 13.5 | 1.5 | 0.5 | 0.0 | 2.3 | 13.1 | 82.8 |
| NoKASII + NoΔ12-DES | 1.7 | 36.0 | 22.4 | 2.4 | 7.1 | 6.6 | 1.2 | 1.0 | 5.4 | 16.1 | 90.8 |
| NoKASII + Noω3-DES | 1.1 | 39.4 | 24.2 | 1.8 | 13.8 | 1.9 | 0.5 | 0.0 | 1.2 | 16.1 | 107.4 |

As is apparent from Table 4, in the strains into which the NoKASII gene and the NoΔ12-DES gene (NoKASII+NoΔ12-DES) were introduced, a ratio of C18:1 fatty acid was reduced, and ratios of C18:2, C18:3, C20:3, C20:4 and C20:5 fatty acids were improved in comparison with the wild type strain (NIES-2145). Furthermore, the ratios of C20:4 and C20:5 fatty acids were by further improved by introducing the NoΔ12-DES gene into the NoKASII transgenic strain (NoKASII).

In addition, in the strains into which the NoKASII gene and the Noω3-DES gene (NoKASII+Noω3-DES) were introduced, a ratio of C20:4 fatty acid was reduced, and ratio of C20:5 fatty acid was improved in comparison with the wild type strain (NIES-2145). Furthermore, the ratio of C20:5 fatty acid was by further improved by introducing the Noω3-DES gene into the NoKASII transgenic strain (NoKASII).

From these results, it became apparent that the productivity of PUFA is much further improved by promoting expression of the desaturase gene in addition to the NoKASII gene.

As described above, the transformant in which productivity of the long-chain fatty acids is improved can be prepared by promoting the expression of the KAS gene as specified in the present invention. Further, productivity of the long-chain fatty acids can be improved by culturing this transformant.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-154771 filed in Japan on Aug. 5, 2015, which is entirely herein incorporated by reference.

The invention claimed is:

1. A method comprising the steps of:

culturing a transformant in which the expression of a gene encoding protein (A) or (B) is enhanced, and improving the ratio of the amount of long-chain fatty acids or the amount of ester compound thereof, in the total amount of all fatty acids, or the total amount of fatty acid esters consisting of the ester compounds thereof, wherein:

protein (A) is a protein consisting of the amino acid sequence set forth in SEQ ID NO: 1; and protein (B) is a protein consisting of an amino acid sequence having 92% or more identity with the amino acid sequence of the protein (A), and having β-ketoacyl-ACP synthase activity wherein the transformant is an algal cell.

2. The method according to claim 1, wherein the gene encoding the protein (A) or (B) is introduced into the transformant to enhance the expression of the gene.

3. A method of producing lipids, comprising the steps of:

culturing a transformant into which a gene encoding protein (A) or (B) is introduced, and producing long-chain fatty acids or the lipids containing these fatty acids as components, wherein:

protein (A) is a protein consisting of the amino acid sequence set forth in SEQ ID NO: 1; and protein (B) is a protein consisting of an amino acid sequence having 92% or more identity with the amino acid sequence of the protein (A), and having β-ketoacyl-ACP synthase activity wherein the transformant is an algal cell.

4. The method according to claim 1, wherein the identity of the protein (B) with the amino acid sequence of the protein (A) is 95% or more, and the protein (B) has β-ketoacyl-ACP synthase activity.

5. The method according to claim 1, wherein expression of a gene encoding a desaturase is enhanced in the transformant.

6. The method according to claim 1, wherein the transformant is an alga belonging to the genus *Nannochloropsis*.

7. The method according to claim 1, wherein the lipids contain a long-chain fatty acid having 18 to 22 carbon atoms or an ester compound thereof.

8. The method according to claim 1, wherein the long-chain fatty acid is a long-chain polyunsaturated fatty acid.

9. A transformant, which is obtained by introducing a gene encoding the following protein (A) or (B), or a gene consisting of the following DNA (a) or (b), into a host, wherein:

protein (A) is a protein consisting of the amino acid sequence set forth in SEQ ID NO: 1;

protein (B) is a protein consisting of an amino acid sequence having 92% or more identity with the amino acid sequence of the protein (A), and having β-ketoacyl-ACP synthase activity;

DNA (a) is a DNA consisting of the nucleotide sequence set forth in SEQ ID NO: 2; and DNA (b) is a DNA consisting of a nucleotide sequence having 85% or more identity with the nucleotide sequence of the DNA (a), and encoding the protein (A) or (B) having β-ketoacyl-ACP synthase activity wherein the transformant is an algal cell.

10. The transformant according to claim 9, wherein expression of a gene encoding a desaturase is enhanced.

11. The transformant according to claim 9, wherein the transformant or the host is an alga belonging to the genus *Nannochloropsis*.

12. The method according to claim 3, wherein the identity of the protein (B) with the amino acid sequence of the protein (A) is 95% or more, and the protein (B) has β-ketoacyl-ACP synthase activity.

13. The method according to claim 3, wherein expression of a gene encoding a desaturase is enhanced in the transformant.

14. The method according to claim 3, wherein the transformant is an alga belonging to the genus *Nannochloropsis*.

15. The method according to claim 3, wherein the lipids contain a long-chain fatty acid having 18 to 22 carbon atoms or an ester compound thereof.

16. The method according to claim 3, wherein the long-chain fatty acid is a long-chain polyunsaturated fatty acid.

* * * * *